(12) United States Patent
Liu et al.

(10) Patent No.: US 7,129,073 B2
(45) Date of Patent: Oct. 31, 2006

(54) REGULATION OF NEURONAL FUNCTION THROUGH METABOTROPIC GLUTAMATE RECEPTOR SIGNALING PATHWAYS

(75) Inventors: Feng Liu, Plainsboro, NJ (US); Angus C. Nairn, Guilford, CT (US); Paul Greengard, New York, NY (US)

(73) Assignee: The Rockefeller University, New York, NY (US)

( * ) Notice: Subject to any disclaimer, the term of this patent is extended or adjusted under 35 U.S.C. 154(b) by 652 days.

(21) Appl. No.: 10/175,190

(22) Filed: Jun. 18, 2002

(65) Prior Publication Data

US 2006/0223158 A1 Oct. 5, 2006

Related U.S. Application Data

(60) Provisional application No. 60/298,978, filed on Jun. 18, 2001.

(51) Int. Cl.
*C12N 9/12* (2006.01)

(52) U.S. Cl. ........................ 435/194; 435/184

(58) Field of Classification Search ................ 435/194, 435/184
See application file for complete search history.

(56) References Cited

FOREIGN PATENT DOCUMENTS

WO PCT/US02/19288 6/2002

OTHER PUBLICATIONS

Sharma, P et al. Regulation of cyclin-dependent kinase 5 catalytic activity by phosphorylation. Proc. Natl. Acad. Sci. USA. 1999. 96: 11156-11160.*
Gietzen, KF et al. Identification of inhibitory autophosphorylation sites in casein kinase I e. Journal of Biological Chemistry. 1999. 274(45): 32063-32070.*
Hernandez-Lopez, S et al. D2 dopamine receptors in striatal medium spiny neurons reduce L-type Ca2+ currents and excitability via a novel PLC beta1-IP3-calcineurin-signaling cascade. Journal of Neuroscience. Dec. 2000. 20(24): 8987-8995.*
Nath et al., "Processing of cdk5 Activator p35 to Its Truncated Form (p25) by Calpain in Acutely Injured Neuronal Cells", Jun. 5, 2000, Biochemical and Biophysical Research Communications, pp. 16-21.
Cegielska et al., "Autoinhibition of Casein Kinase I ϵ (CKIϵ) Is Relieved by Protein Phosphatases and Limited Proteolysis", Sep. 3, 1997, The Journal of Biological Chemistry, vol. 273, pp. 1357-1364.
Desdouits et al., "Phosphorylation of DARPP-32, a Dopamine- and cAMP-regulated Phosphoprotein, by Casein Kinase I in Vitro and in Vivo", Oct. 31, 1994, Journal of Biological Chemistry, vol. 270, No. 15 pp. 8772-8778.
Liu et al., "Regulation of cyclin-dependent kinase 5 and casein kinase 1 by metabotropic glutamate receptors", Sep. 25, 2001, PNAS, vol. 98, pp. 11062-11068.
*SIGMA-RBI Handbook of Receptor Classification and Signal Transduction* (4th edition; K.J. Watling, editor; Sigma-RBI, Natick MA, 2001), pp. 194-195.

* cited by examiner

*Primary Examiner*—Leon B. Lankford, Jr.
*Assistant Examiner*—Susan E. Fernandez
(74) *Attorney, Agent, or Firm*—Jones Day

(57) ABSTRACT

The present invention provides methods and compositions for modulating the activities of metabotropic glutamate receptor intracellular signaling molecules. The present invention provides methods and compositions for modulating the activities of casein kinase I and/or cyclin-dependent kinase 5 in cells or tissues. The present invention provides methods of modulating the function of calcium channels in cells or tissues. The present invention provides methods of treating calcium channel dysfunction. The present invention provides methods of identifying agents that modulate the activities of the metabotropic glutamate receptor intracellular signaling molecules casein kinase I and/or cyclin-dependent kinase 5 for use in such treatments.

7 Claims, 14 Drawing Sheets

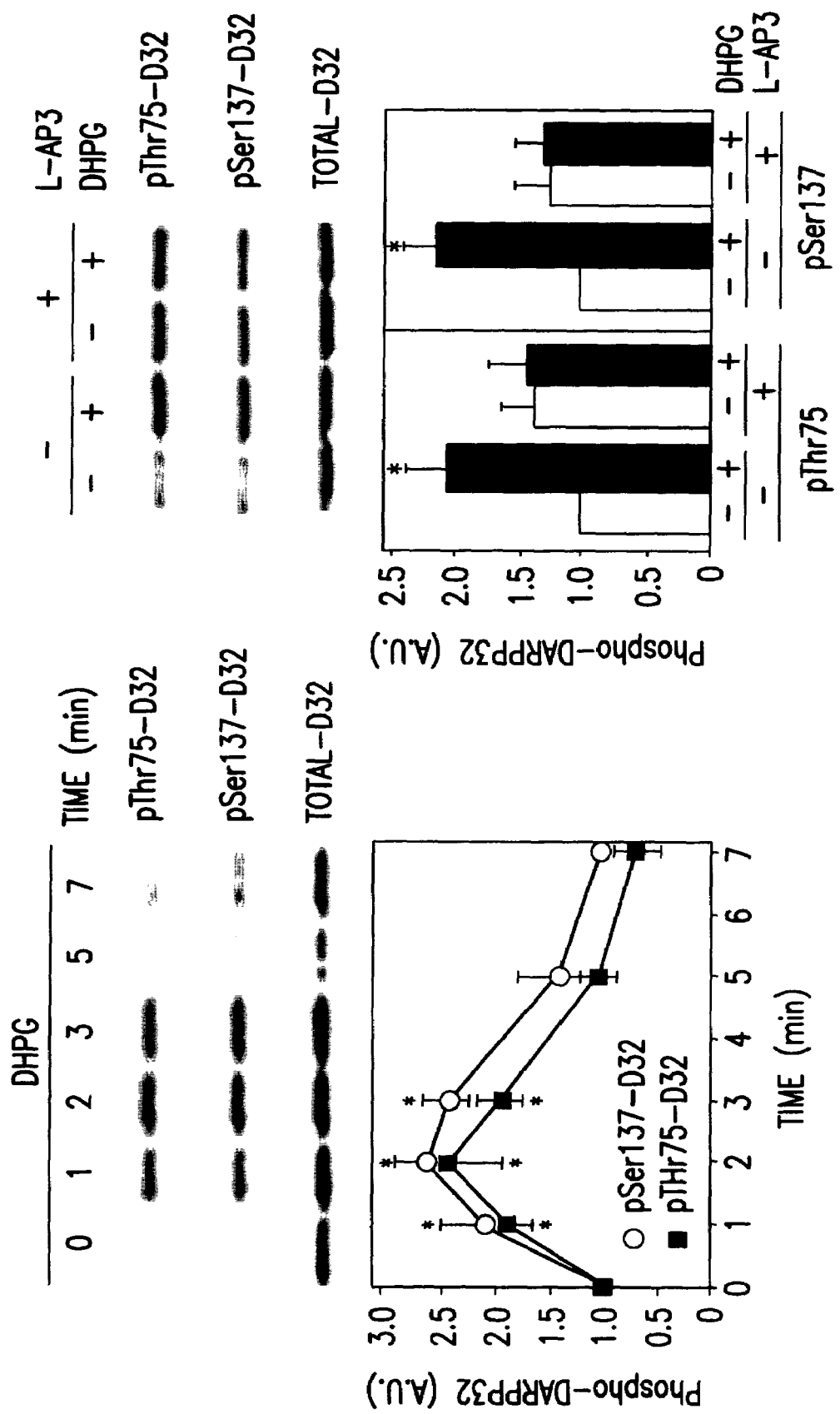

Figure 6A:
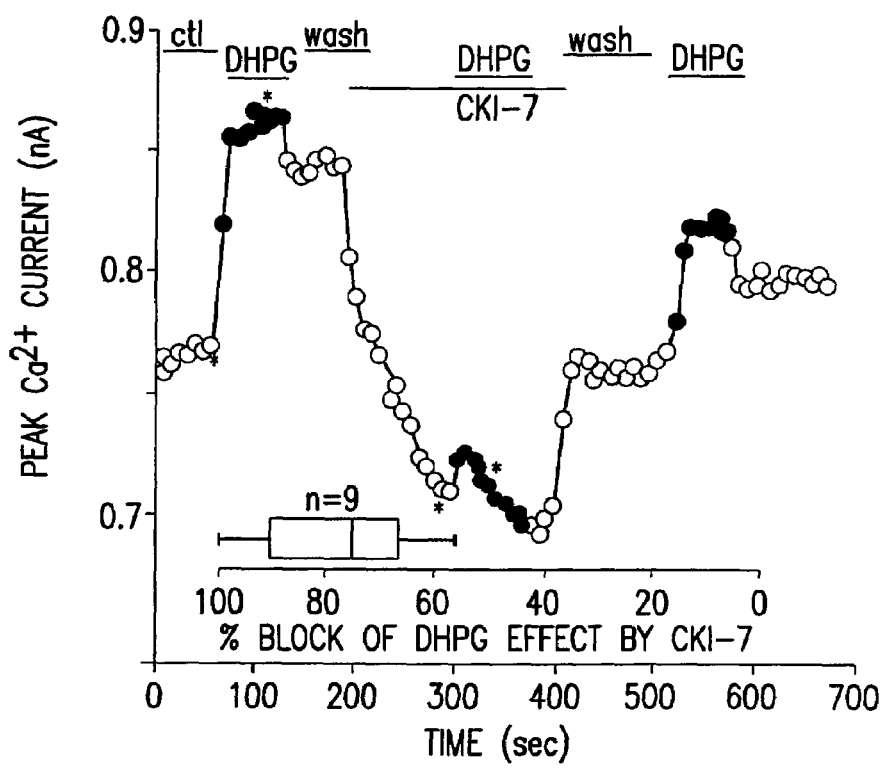

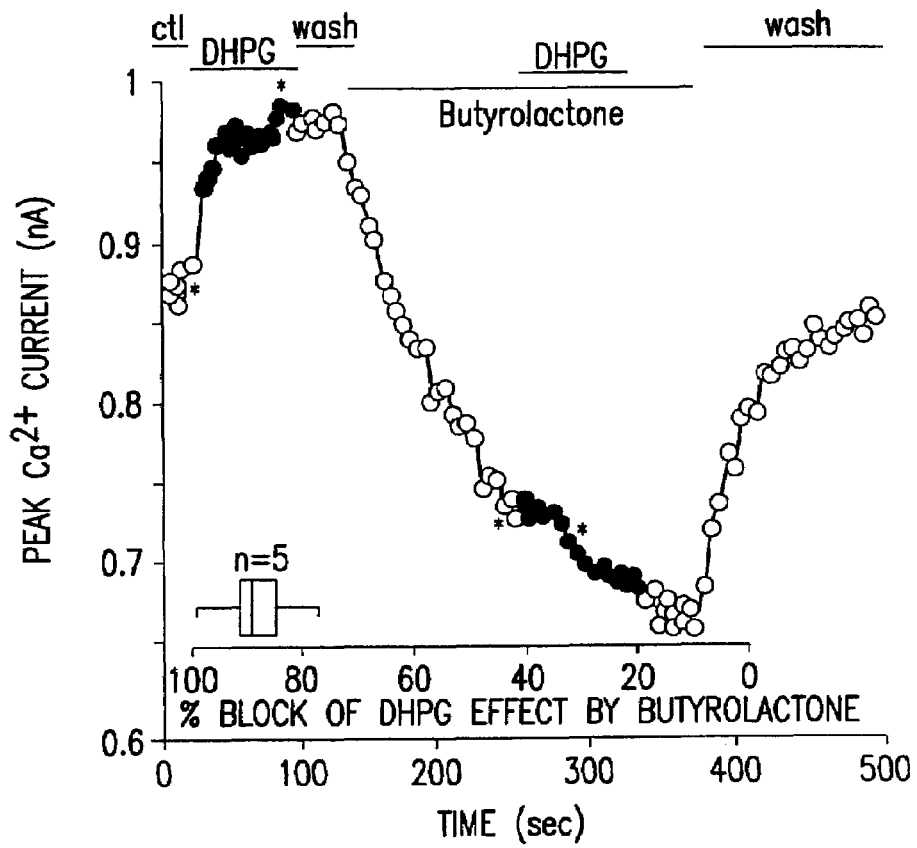
FIG. 6C
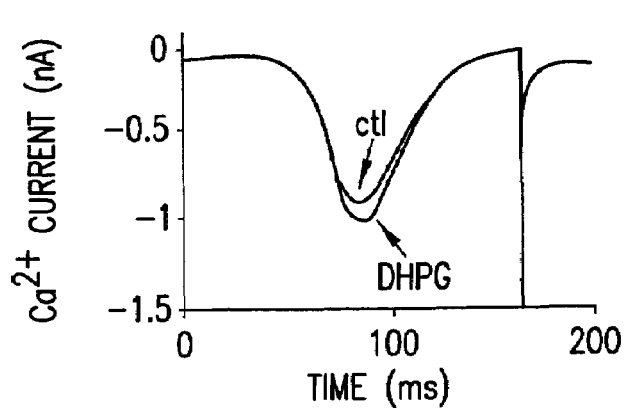
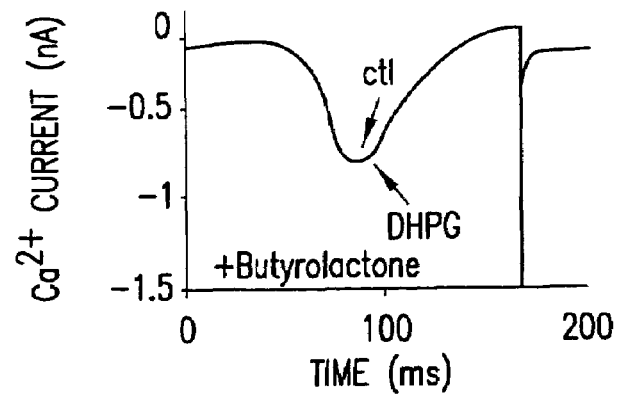
FIG. 6D

SEQUENCE LISTING

```
<160> NUMBER OF SEQ ID NOS: 6

<210> SEQ ID NO 1
<211> LENGTH: 204
<212> TYPE: PRT
<213> ORGANISM: Homo sapiens

<400> SEQUENCE: 1

Met Asp Pro Lys Asp Arg Lys Lys Ile Gln Phe Ser Val Pro Ala Pro
1               5                   10                  15
```

-continued

```
Pro Ser Gln Leu Asp Pro Arg Gln Val Glu Met Ile Arg Arg Arg
            20                  25                  30
Pro Thr Pro Ala Met Leu Phe Arg Leu Ser Glu His Ser Ser Pro Glu
        35                  40                  45
Glu Glu Ala Ser Pro His Gln Arg Ala Ser Gly Glu Gly His His Leu
    50                  55                  60
Lys Ser Lys Arg Pro Asn Pro Cys Ala Tyr Thr Pro Pro Ser Leu Lys
65                  70                  75                  80
Ala Val Gln Arg Ile Ala Glu Ser His Leu Gln Ser Ile Ser Asn Leu
                85                  90                  95
Asn Glu Asn Gln Ala Ser Glu Glu Asp Glu Leu Gly Glu Leu Arg
            100                 105                 110
Glu Leu Gly Tyr Pro Arg Glu Glu Asp Glu Glu Glu Glu Asp Asp
        115                 120                 125
Glu Glu Glu Glu Glu Glu Asp Ser Gln Ala Glu Val Leu Lys Val
    130                 135                 140
Ile Arg Gln Ser Ala Gly Gln Lys Thr Thr Arg Gly Leu Gly Leu Glu
145                 150                 155                 160
Gly Pro Trp Glu Arg Pro Pro Leu Asp Glu Ser Glu Arg Asp Gly
                165                 170                 175
Gly Ser Glu Asp Gln Val Glu Asp Pro Ala Leu Ser Glu Pro Gly Glu
            180                 185                 190
Glu Pro Gln Arg Pro Ser Pro Ser Glu Pro Gly Arg
        195                 200

<210> SEQ ID NO 2
<211> LENGTH: 201
<212> TYPE: PRT
<213> ORGANISM: Mus musculus

<400> SEQUENCE: 2

Met Asp Pro Lys Asp Arg Lys Lys Ile Gln Phe Ser Val Pro Ala Pro
1               5                   10                  15
Pro Ser Gln Leu Asp Pro Arg Gln Val Glu Met Ile Arg Arg Arg
            20                  25                  30
Pro Thr Pro Ala Leu Leu Phe Arg Val Ser Glu His Ser Ser Pro Glu
        35                  40                  45
Glu Glu Glu Glu Glu Ala Ser Pro His Gln Arg Thr Ser Gly Glu Gly
    50                  55                  60
His His Pro Lys Ser Lys Arg Pro Asn Pro Cys Ala Tyr Thr Pro Pro
65                  70                  75                  80
Ser Leu Lys Ala Val Arg Arg Leu Gln Thr Ile Ser Asn Leu Ser Glu
                85                  90                  95
Asn Gln Ala Ser Glu Glu Asp Glu Leu Gly Glu Leu Arg Glu Leu
            100                 105                 110
Gly Tyr Pro Gln Glu Asp Asp Glu Asp Glu Asp Glu Glu Glu Asp
        115                 120                 125
Glu Glu Glu Asp Ser Gln Ala Glu Val Leu Lys Gly Ser Arg Gly Thr
    130                 135                 140
Val Gly Gln Lys Leu Leu Val Ala Gly Val Trp Arg Gly Pro Gly Ser
145                 150                 155                 160
Ala His Leu Leu Trp Met Ser Pro Arg Glu Met Glu Thr Leu Arg Thr
                165                 170                 175
Lys Trp Lys Ala Glu Gln His Glx Val Ser Leu Glu Arg Asn Leu Ser
            180                 185                 190
```

Ile Pro Ala Pro Pro Glu Pro Gly Thr
        195                 200

<210> SEQ ID NO 3
<211> LENGTH: 205
<212> TYPE: PRT
<213> ORGANISM: Rattus sp.

<400> SEQUENCE: 3

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Leu Leu Phe Arg Val Ser Glu His Ser Ser Pro Glu
        35                  40                  45

Glu Glu Ser Ser Pro His Gln Arg Thr Ser Gly Glu Gly His His Pro
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Thr Ile Ser Asn Leu
                85                  90                  95

Ser Glu Asn Gln Ala Ser Glu Glu Asp Glu Leu Gly Glu Leu Arg
            100                 105                 110

Glu Leu Gly Tyr Pro Asn Glu Asp Glu Glu Asp Glu Asp Glu Asp
        115                 120                 125

Glu Glu Glu Asp Glu Glu Asp Ser Gln Ala Glu Val Leu Lys Gly
    130                 135                 140

Ser Arg Gly Thr Ala Gly Asn Lys Leu Thr Ser Gly Gln Gly Leu Glu
145                 150                 155                 160

Gly Pro Trp Glu Arg Pro Pro Leu Asp Glu Pro Gln Arg Asp Gly
                165                 170                 175

Asn Ser Glu Asp Gln Gly Glu Gly Arg Ala Thr Gln Ser Glu Pro Gly
            180                 185                 190

Glu Glu Pro Arg His Pro Thr Pro Pro Glu Ser Gly Thr
        195                 200                 205

<210> SEQ ID NO 4
<211> LENGTH: 203
<212> TYPE: PRT
<213> ORGANISM: bovine

<400> SEQUENCE: 4

Met Asp Pro Lys Asp Arg Lys Lys Ile Gln Phe Ser Val Pro Ala Pro
1               5                   10                  15

Pro Ser Gln Leu Asp Pro Arg Gln Val Glu Met Ile Arg Arg Arg Arg
            20                  25                  30

Pro Thr Pro Ala Met Leu Phe Arg Leu Ser Glu His Ser Ser Pro Glu
        35                  40                  45

Glu Glu Ala Ser Pro His Gln Arg Ala Ser Gly Glu Gly His His Leu
    50                  55                  60

Lys Ser Lys Arg Pro Asn Pro Cys Ala Tyr Thr Pro Pro Ser Leu Lys
65                  70                  75                  80

Ala Val Gln Arg Ile Ala Glu Ser His Leu Gln Ser Ile Ser Asn Leu
                85                  90                  95

Gly Glu Asn Gln Ala Ser Glu Glu Asp Glu Leu Gly Glu Leu Arg
            100                 105                 110

```
                                    -continued

Glu Leu Gly Tyr Pro Arg Glu Glu Glu Glu Glu Glu Glu Asp
        115                 120                 125

Glu Glu Glu Glu Glu Asp Ser Gln Ala Glu Val Leu Lys Gly Ser Arg
    130                 135                 140

Gly Ser Ala Gly Gln Lys Thr Thr Tyr Gly Gln Gly Leu Glu Gly Pro
145                 150                 155                 160

Trp Glu Arg Pro Pro Pro Leu Asp Gly Pro Gln Arg Asp Gly Ser Ser
                165                 170                 175

Glu Asp Gln Val Glu Asp Pro Ala Leu Asn Glu Pro Gly Glu Glu Pro
            180                 185                 190

Gln Arg Met Pro Ala His Pro Glu Pro Gly Thr
            195                 200

<210> SEQ ID NO 5
<211> LENGTH: 16
<212> TYPE: PRT
<213> ORGANISM: Homo sapiens

<400> SEQUENCE: 5

Lys Arg Pro Asn Pro Cys Ala Tyr Thr Pro Pro Ser Leu Lys Ala Val
1               5                   10                  15

<210> SEQ ID NO 6
<211> LENGTH: 11
<212> TYPE: PRT
<213> ORGANISM: Homo sapiens

<400> SEQUENCE: 6

Glu Glu Glu Asp Ser Gln Ala Glu Val Leu Lys
1               5                   10
```

REGULATION OF NEURONAL FUNCTION THROUGH METABOTROPIC GLUTAMATE RECEPTOR SIGNALING PATHWAYS

RELATED APPLICATIONS

This application claims benefit, under 35 U.S.C. § 119(e), of U.S. provisional application No. 60/298,978, filed on Jun. 18, 2001, which is incorporated herein by reference in its entirety.

This invention was made with Government support under grant numbers MH40899, DA10044 and AG09464, awarded by the National Institutes of Health. The United States Government has certain rights in the invention.

1. TECHNICAL FIELD

The present invention relates to methods and compositions for modulating the activities of metabotropic glutamate receptor intracellular signaling molecules. The present invention relates to methods and compositions for modulating the activities of casein kinase I and/or cyclin-dependent kinase 5 in cells or tissues. The present invention relates to methods of modulating the function of calcium channels in cells or tissues. The present invention relates to methods of treating calcium channel dysfunction. The present invention relates to methods of identifying agents that modulate the activities of metabotropic glutamate receptor intracellular signaling molecules, casein kinase I and/or cyclin-dependent kinase 5, for use in such treatments.

2. BACKGROUND OF THE INVENTION

Casein Kinase I ("CKI" or "CK1") was one of the first serine/threonine protein kinases to be isolated and characterized (Gross, S. D. and R. A. Anderson. 1998. *Cell Signal* 10:699–671). It is a ubiquitous enzyme that can be found in the nucleus and the cytosol of cells and bound to the cytoskeleton or to cell membranes. The CKI (CK1) family is a family of multiple isoforms encoded by at least seven distinct genes (CKIα, β, γi, γ2, γ3, δ, E; Desdouits, F. et al. 1995. *J. Biol. Chem.* 270:8772–8778). These isoforms exhibit more than 50% amino acid identity within the catalytic domains, but contain divergent carboxy-termini (Graves, P. R. and P. J. Roach. 1995. *J. Biol. Chem.* 270:21689–21694; Cegielska, A. et al. 1998. *J. Biol. Chem.* 273:1357–1364; Gietzen, K. F. and D. M. Virshup. 1999. *J. Biol. Chem.* 274:32063–32070). It has been reported that at least two CKI isoforms, CKIδ and CKIε, are regulated by auto-phosphorylation at their COOH-termini. These studies suggest that the phosphorylated COOH-terminus may act as a pseudo-substrate that inhibits enzyme activity. Elimination of autophosphorylation by either truncation of the COOH-terminus or by dephosphorylation has been found to result in increased kinase activity (Graves, P. R. and P. J. Roach. 1995. *J. Biol. Chem.* 270:21689–21694; Cegielska, A. et al. 1998. *J. Biol. Chem.* 273:1357–1364).

In the central nervous system (CNS), CKI appears to play a role in regulation of circadian rhythm (Camacho, F. et al. 2001. *FEBS Lett.* 489:159–165) and intracellular trafficking (Murakami, A. et al. 1999. *J. Biol. Chem.* 274:3804–3810; Panek, H. R. et al. 1997. *EMBO J.* 16:4194–4204; Wang, X. et al. 1996. *Mol. Cell. Biol.* 16:5375–5385). In the neostriatum, CKI has been found to phosphorylate DARPP-32 (Dopamine and cAMP-Regulated Phosphoprotein, molecular mass 32 kDa; also known as "DARPP-32") at Ser137 (Desdouits, F. et al. 1995. *J. Biol. Chem.* 270:8772–8778). Phosphorylation at Thr34 by cAMP-dependent protein kinase (PKA) converts DARPP-32 into an inhibitor of protein phosphatase-1 (PP1), a process that is critical for the actions of dopamine in the neostriatum (Greengard, P. et al. 1998. *Brain Res. Rev.* 26:274–284; Greengard, P. et al. 1999. *Neuron* 23:435–437). Phospho-Thr34 is dephosphorylated by PP2B (also named calcineurin or $Ca^{2+}$/calmodulin-dependent phosphatase) and the phosphorylation of Ser137 influences the ability of phospho-Thr34 to be dephosphorylated by PP2B (Desdouits, F. et al. 1995. *Proc. Natl. Acad. Sci. USA* 92:2682–2685; Desdouits, F. et al. 1998. *Biochem. J.* 330:211–216). Cyclin-dependent kinase 5 ("cdk5," "Cdk5" or "CDK5") was originally identified as a homologue of $p34^{cdc2}$ protein kinase. Subsequent studies have shown that unlike Cdc2, Cdk5 kinase activity is not detected in dividing cells. Instead, the active form of Cdk5 is present only in differentiated neurons, where it associates with a neuron-specific 35 kDa regulatory subunit, termed p35. Cdk5/p35 plays a variety of roles in the developing and adult nervous system.

Studies of mice in which the gene encoding either Cdk5 or p35 has been disrupted have indicated that both mutants exhibit abnormalities in the laminar structure of the cerebral cortex (Chae, T. et al. 1997. *Neuron* 18:29–42; Ohshima, T. et al. 1996. *Proc. Natl. Acad. Sci. USA* 93:11173–11178). Cdk5/p35 is localized at the leading edge of axonal growth cones, and inactivation of Cdk5 in cultured neurons inhibits neurite outgrowth. Recent studies have linked mis-regulation of Cdk5 to Alzheimer's disease (Kusakawa, G. et al. 2000. *J. Biol. Chem.* 275:17166–17172; Lee, M. S. et al. 2000. *Nature* 405:360–364; Nath, R. et al. 2000. *Biochem. Biophys. Res. Commun.* 274:16–21; Patrick, G. N. et al. 1999. *Nature* 402:615–622). In these studies, conversion of p35 to p25 by the action of calpain causes prolonged activation and altered localization of Cdk5. In turn, Cdk5/p25 can hyperphosphorylate tau, disrupt cytoskeletal structure and promote apoptosis of primary neurons. Recent studies have shown that Cdk5 also phosphorylates DARPP-32 at Thr75 (Nishi, A. et al. 2000. *Proc. Natl. Acad. Sci. USA* 97:12840–12845; Bibb, J. A. et al. 1999. *Nature* 402: 669–671). Phosphorylation of DARPP-32 at Thr75 by Cdk5 influences phosphorylation of Thr34 in DARPP-32 by PKA and plays an important modulatory role in the DARPP-32/ PP1 cascade (Bibb, J. A. et al. 1999. *Nature* 402:669–671). Finally, recent studies have suggested that glutamate antagonists are anti-carcinogenic, an effect that was calcium dependent (Cavalheiro, E. A. et al. 2001. *Proc. Natl. Acad. Sci. USA* 98:5947–5948; Rzeski, W. et al. 2001. *Proc. Natl. Acad. Sci. USA* 98:6372–6377).

Hence, despite the knowledge about the actions of CKI and Cdk5 in the CNS, as discussed hereinabove, surprisingly little is known about the regulation of these two kinases by first messengers. Therefore, there is a need in the art to provide new methods of screening that can be used to develop novel compositions or drugs that can be used to treat diseases or disorders related to the regulation of CKI and Cdk5. Furthermore, there is a need to develop treatments for such diseases or disorders that are due, at least in part, to an aberration or dysregulation of an intracellular signaling pathway regulated by CKI and/or Cdk5. The present invention provides such methods and compositions.

Citation or identification of any reference in Section 2, or in any other section of this application, shall not be considered an admission that such reference is available as prior art to the present invention.

3. SUMMARY OF THE INVENTION

The present invention provides a method for modulating casein kinase I ("CKI" or "CK1") and/or cyclin-dependent kinase 5 ("Cdk5," "cdk5" or "CDK5") activity in a cell or tissue of interest, comprising contacting the cell or tissue of interest with an effective amount of a compound that alters the activity of a metabotropic glutamate receptor (mGluR) intracellular signaling molecule, wherein contact of the cell or tissue with the compound results in a modulation of the activity of casein kinase I or cyclin-dependent kinase 5.

The present invention provides a method for regulating activity of calcium channels comprising administering (for example, to an individual, patient or animal) an effective amount of a compound of the invention, for example, a compound identified by the methods of the invention, wherein the compound modulates the activity of casein kinase I (CKI) and/or cyclin-dependent kinase 5 (Cdk5), and wherein modulation of CKI or Cdk5 activity results in an alteration in the activity of calcium channels in the neuron. In a specific embodiment, the calcium channels are in an excitable cell, e.g., a neuron. In another embodiment, the method involves administration of a mGluR agonist in order to increase activity of CKI and Cdk5 and thereby alter activity of calcium channels.

The present invention provides, in vivo, in situ, and in vitro, methods of identifying an agent, drug or compound for modulating the activity of casein kinase I (CKI) and/or cyclin-dependent kinase 5 (Cdk5) in a cell or tissue of interest. Such methods can be used alone or in conjunction with each other. In one embodiment, the method comprises determining a first level of casein kinase I and/or cyclin-dependent kinase 5 activity in a cell or tissue of interest; contacting the cell or tissue with a test compound; and determining a second level of casein kinase I and/or cyclin-dependent kinase 5 activity in the cell or tissue, wherein a difference in the first level and the second level of casein kinase I and/or cyclin-dependent kinase 5 activity is indicative of the ability of the test compound to modulate casein kinase I and/or cyclin-dependent kinase 5 activity.

In another embodiment, the method comprises determining a first level of casein kinase I and/or cyclin-dependent kinase 5 activity in a cell or tissue of interest; determining a first level of calcium channel activity in the cell or tissue; contacting the cell or tissue with a test compound; determining a second level of casein kinase I and/or cyclin-dependent kinase 5 activity in the cell or tissue; and determining a second level of calcium channel activity in the cell or tissue, wherein a difference in the first level and the second level of casein kinase I and/or cyclin-dependent kinase 5 activity and a difference in the first level and the second level of calcium channel activity are indicative of the ability of the test compound to modulate the activity of calcium channels.

The present invention also provides in vivo methods of identifying agents that can modulate the activity of CKI or Cdk5. Such methods can be employed alone or in conjunction with in vitro and in situ methods as disclosed herein. One such method comprises administering the agent to a non-human mammal. The amount (and/or rate) of activation of CKI and/or Cdk5 is then determined. An agent is identified as capable of modulating the activity of CKI and/or Cdk5 when the amount (and/or rate) of activation is increased or decreased in the presence of the agent relative to in the absence of the agent. In preferred embodiments, the non-human mammal is a rodent. In a more preferred embodiment, the rodent is a mouse.

The invention also provides methods of screening potential agents (or drugs or compounds) in order to select an agent that can potentially ameliorate and/or be used in treatment of mGluR-related, CKI-related, Cdk5-related and/or calcium channel-related disorders.

The present invention also provides methods of identifying agents (or drugs or compounds), e.g., drug screening assays, which drugs may be used in therapeutic methods for the treatment of mGluR-related, CKI-related, Cdk5-related and/or calcium channel-related disorders.

The present invention also provides compositions for modulating the activity of casein kinase I (CKI) and/or cyclin-dependent kinase 5 (Cdk5). The invention also provides compositions for modulating the activity of calcium channels via modulation of the activity of casein kinase I (CKI) and/or cyclin-dependent kinase 5 (Cdk5).

The present invention further provides methods for performing rational drug design to develop drugs that can modulate activity of CKI and/or Cdk5 and thereby ameliorate mGluR-related, CKI-relate, Cdk5-related and/or calcium channel-related disorders.

In one embodiment, the invention provides methods of identifying a compound that modulates the activity of cyclin-dependent kinase 5 in a cell or tissue of interest comprising: (a) determining a first level of cyclin-dependent kinase 5 activity in said cell or tissue; (b) contacting said cell or tissue with a test compound; and (c) determining a second level of cyclin-dependent kinase 5 activity in said cell or tissue, wherein a difference in said first level and said second level of cyclin-dependent kinase 5 activity is indicative of the ability of said test compound to modulate cyclin-dependent kinase 5 activity, and wherein modulation of cyclin-dependent kinase 5 activity is regulated by modulation of the activity of metabotropic glutamate receptors.

The present invention also provides diagnostic and therapeutic methods for the treatment of a mGluR-related, CKI-related, Cdk5-related or calcium channel-related disorder, including, but not limited the use of compositions or compounds of the invention in the treatment of a mGluR-related, CKI-related, Cdk5-related or calcium channel-related disorder.

In one aspect, the invention provides a method for treating a neuronal condition characterized by an increase or a decrease in calcium channel activity (e.g. calcium channel currents) comprising administering to a subject in need of such treatment an effective amount of a compound of the present invention to modulate CKI and/or Cdk5 activity, and thus increase or decrease calcium channel activity via modulation of a mGluR signaling pathway. In one embodiment, the mGluR signaling pathway comprises: activation of mGluR1 receptors that stimulate G proteins that are coupled to PLCβ, activation of the $Ca^{2+}$/calmodulin-dependent phosphatase, calcineurin (PP2B), by $Ca^{2+}$ released from IP3-sensitive stores, dephosphorylation of the inhibitory autophosphorylation sites on CK1ε by calcineurin, resulting in an increase in kinase activity.

The present invention provides methods for treating a mGluR-related, CKI-related, Cdk5-related or calcium channel-related disorder in an individual (e.g., a patient) or an animal subject by administering an effective amount of a compound of the invention to modulate CKI and/or Cdk5 activity. In one embodiment, the agent promotes or increases the activity of CKI and/or Cdk5. In another embodiment, the agent inhibits or decreases the activity of CKI and/or Cdk5.

The invention provides methods of administering an agent (or drug or compound) of the invention that can ameliorate a symptom of a mGluR-related, CKI-relate, Cdk5-related and/or calcium channel-related disorder, disease and/or condition in a patient or subject exhibiting the symptom. In certain embodiments, the invention provides methods of administering an agent identified by the methods disclosed herein, that can ameliorate a symptom of a mGluR-related, CKI-related, Cdk5-related or calcium channel-related disorder in a patient or subject exhibiting the symptom. In other embodiments, an agonist of mGluR activity can be used to for treating a mGluR-related, CKI-related, Cdk5-related or calcium channel-related disorder. In yet other embodiments, an antagonist of mGluR activity can be used to for treating a mGluR-related, CKI-related, Cdk5-related or calcium channel-related disorder.

The present invention also provides compositions for modulating the activity of casein kinase I (CKI) and/or cyclin-dependent kinase 5 (Cdk5). The invention also provides compositions for modulating the activity of calcium channels via modulation of the activity of casein kinase I (CKI) and/or cyclin-dependent kinase 5 (Cdk5).

The present invention also provides pharmaceutical compositions of the agents (or drugs or compounds) of the invention disclosed herein. The invention encompasses pharmaceutical compositions for regulating CKI and/or Cdk5 activity, and for diagnosing or treating a mGluR-related, CKI-related, Cdk5-related or calcium channel-related disorder. Because a loss of normal function results in the development of a phenotype of the above-listed diseases or disorders, activation of the metabotropic glutamate receptor (mGluR) signaling pathway, or an increase in CKI and/or Cdk5 activity (e.g., downstream activation) facilitates amelioration of a symptom in individuals exhibiting a symptom of such a disorder.

3.1. DEFINITIONS

As used herein, the term "modulate" or "modulation" shall have its usual meaning, and encompasses the meanings of the words "enhance," "inhibit," and "mimic." "Modulation" of activity may be either an increase or a decrease in activity depending on whether an agonist or antagonist is administered.

As used herein, an "agonist" is any compound that acts directly or indirectly through or upon a receptor to produce a pharmacological effect, while an "antagonist" is any compound that blocks the stimulation of a receptor and its resulting pharmacological effect.

As used herein, an "effective amount" of a modulatory compound is an amount that can be determined by one of skill in the art based on data from studies using methods of analysis such as those disclosed herein. Such data may include, but not be limited to, results from $IC_{50}$ determinations, as discussed below in Section 5.6.

As used herein, the term "DARPP-32" is used interchangeably with "Dopamine- and cyclic AMP (cAMP)-Regulated PhosphoProtein" and "DARPP32" and is a 32 kilodalton cytosolic protein that is selectively enriched in medium-sized spiny neurons in neostriatum. The human, mouse, rat and bovine DARPP-32 amino acid sequences are disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties (see SEQ ID NOS:1–4, respectively).

As used herein, the term "Thr75 DARPP-32" is used interchangeably with "Thr75 DARPP32," "thr$^{75}$DARPP-32", "Threonine-75 DARPP-32" and "threonine-75 DARPP-32" along with analogous abbreviations, and denotes the seventy-fifth amino acid residue in the amino sequence of DARPP-32 as disclosed by Brene et al. (J. Neurosci. 14:985–998 (1994)) having the GenBank Accession of AAB30129.1, which is a threonine residue that, as disclosed herein, can be phosphorylated by Cdk5.

As used herein, the term "phospho-Thr75 DARPP-32," or analogous abbreviations as disclosed above, denotes the phosphorylated form of Thr75 DARPP-32.

As used herein, the term "Thr34 DARPP-32" is used interchangeably with "Thr34 DARPP32," "thr$^{34}$ DARPP-32" "Threonine-34 DARPP-32" and "threonine-34 DARPP-32" along with analogous abbreviations and denotes the thirty-fourth amino acid residue of the amino sequence of DARPP-32 as disclosed by Brene et al. (J. Neurosci. 14:985–998 (1994)) having the GenBank Accession No. of AAB30129.1, which is a threonine residue that can be phosphorylated by the cyclic AMP dependent protein kinase (PKA).

As used herein, the term "phospho-Thr34 DARPP-32," or analogous abbreviations as disclosed above, denotes the phosphorylated form of Thr34 DARPP-32.

As used herein, the terms "CKI," "casein kinase 1" or "CK1," are used interchangeably with "casein kinase I." CKI is a member of the serine/threonine protein kinases. CKI includes, but is not limited to members of the CKI (CK1) family, which consist of multiple isoforms encoded by at least seven distinct genes (CKIα, β, γ1, γ2, γ3, δ, ε; Desdouits, F. et al. 1995. *J. Biol. Chem.* 270:8772–8778; Gross et al., 1998, *Cell Signal* 10(10): 699–711; Vielhaber et al., 2001, *IUBMB Life* 51(2), 73–8).

As used herein, "an analog of CKI" is used interchangeably with "a homolog of CKI" and is a protein kinase that, like CKI, phosphorylates DARPP-32 on Ser137.

As used herein, the term "CKI phosphorylatable fragment of DARPP-32" is a protein fragment of DARPP-32 that contains a serine residue that, when in the dephosphorylated form, can be phosphorylated by CKI. For human DARPP-32 having the amino acid sequence of SEQ ID NO:1, the serine residue is preferably Ser137 DARPP-32. Such fragments can be between about 5 and 100 residues, or more preferably between about 10 and 50 residues. For example, in a particular embodiment, the peptide fragment comprises 5 consecutive amino acids from SEQ ID NO:1 including Ser 37. In another embodiment of this type, the peptide fragment comprises 7 consecutive amino acids from SEQ ID NO:1 including Ser 37. In an alternative embodiment the peptide fragment comprises between 10 and 25 consecutive amino acids from SEQ ID NO:1 including Ser137. All of the peptide fragments can be part of fusion peptides or proteins. A CKI phosphorylatable fragment of DARPP-32 can be prepared by phosphorylating the dephosphorylated fragment or by cleaving (such as with a protease) the phosphorylated fragment from a larger fragment of phospho-Ser137 DARPP-32 protein or from the full-length phospho-Ser137 DARPP-32 protein. Thus the fragments can be synthesized by either standard peptide synthesis disclosed below, or generated through recombinant DNA technology or by classical proteolysis.

As used herein, the terms "CDK5", "Cdk5" or "cdk5" are used interchangeably with "cyclin-dependent kinase 5," which is also known as neuronal cyclin-dependent-like protein (Nclk) and tau protein kinase II (TPKII). Cdk5 is a member of the cyclin dependent kinases but atypically Cdk5 employs a non-cyclin cofactor called neuronal cyclin-dependent-like kinase 5 associated protein (Nck5a) rather than a cyclin. When the term "Cdk5" is used in descriptions of kinase reactions it should be understood that the active form, i.e., the "Cdk5/Nck5a complex" (disclosed hereinbelow) may be the actual catalytic factor and/or a fragment of Cdk5 that retains at least 10% of the catalytic activity of Cdk5.

As used herein, "an analog of Cdk5" is used interchangeably with "a homolog of Cdk5" and is a protein kinase that, like Cdk5, phosphorylates DARPP-32 on Threonine-75 but not on Threonine-34. One such analog is cdk1.

As used herein, "Nck5" a is used interchangeably with "neuronal cyclin-dependent-like kinase 5 associated protein" and is a non-cyclin cofactor for Cdk5. There are at least two isoforms of Nck5a in the brain (p35 and p39), which may also exist as proteolytic fragments (i.e., p25 and p29, respectively).

As used herein, the term "Cdk5/Nck5a complex" denotes the complex formed between Cdk5 and Nck5a, which is an active form of the Cdk5 kinase.

As used herein, the term "Cdk5 phosphorylatable fragment of DARPP-32" is a protein fragment of DARPP-32 that contains a threonine residue that when in the dephosphorylated form can be phosphorylated by Cdk5. For human DARPP-32 having the amino acid sequence of SEQ ID NO:1, the threonine residue is preferably Thr75 DARPP-32. Such fragments can be between about 5 and 100 residues, or more preferably between about 10 and 50 residues. For example, in a particular embodiment, the peptide fragment comprises 5 consecutive amino acids from SEQ ID NO:1 including Thr75. In another embodiment of this type, the peptide fragment comprises 7 consecutive amino acids from SEQ ID NO:1 including Thr75. In an alternative embodiment the peptide fragment comprises between 10 and 25 consecutive amino acids from SEQ ID NO:1 including Thr75. All of the peptide fragments can be part of fusion peptides or proteins. A Cdk5 phosphorylatable fragment of DARPP-32 can be prepared by phosphorylating the dephosphorylated fragment or by cleaving (such as with a protease) the phosphorylated fragment from a larger fragment of phospho-Thr75 DARPP-32 protein or from the full-length phospho-Thr75 DARPP-32 protein. Thus the fragments can be synthesized by either standard peptide synthesis disclosed below, or generated through recombinant DNA technology or by classical proteolysis.

As used herein, the amount and/or rate of phosphorylation of DARPP-32 or the Cdk5 phosphorylatable fragment of DARPP-32 in a kinase reaction is "significantly changed" when the amount and/or rate of phosphorylation of DARPP-32 or the Cdk5 phosphorylatable fragment of DARPP-32 is increased or decreased by at least about 10–25%, relative to the control reaction. Preferably, a significant change in rate of the phosphorylation of DARPP-32 by Cdk5 for example, observed in the presence of a potential modulator is at some point correlated with the Michaelis constants (e.g., the Vmax or Kin) of the reaction. For example, in the case of an inhibitor a KI can be determined. Thus, in certain embodiments, it may be preferable to study various concentrations of a modulator in a reaction mixture to allow the identification of the potential modulator as a modulator.

As used herein, the term "mGluR-related disorder" is used interchangeably with the terms "mGluR disorder," "mGluR condition," "mGluR dysfunction," "mGluR-related dysfunction," "mGluR-related disease," "mGluR-related condition," "dysregulation of a mGluR signaling pathway" or "mGluR signaling pathway dysregulation." A mGluR-related disorder includes, but is not limited to, Alzheimer's disease, Huntington's Disease, Parkinson's disease, Tourette's syndrome, stroke, epilepsy, sleep or circadian rhythm disorder (e.g., insomnia), schizophrenia, depression, attention deficit disorder (ADD), attention deficit hyperactivity disorder (ADHD), drug abuse, pain, and cancer. A mGluR-related disorder also includes, but is not be limited to, a disease (e.g., Parkinson's disease) or a condition (e.g., addiction to cocaine) that involves an aberration or dysregulation of a signal transmission pathway, including, but not limited to, neurotransmission mediated by metabotropic glutamate receptors in excitable cells, tissues or organs (e.g., neurons, brain, central nervous system, etc.). A mGluR-related disorder also includes, but is not limited to, a symptom of a mGluR-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435–447 (1999); Bibb et al., Proc. Natl. Acad. Sci. 97:6809–68 14 (2000); and U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "calcium channel-related disorder" is used interchangeably with the terms "dysregulation of a signaling pathway for calcium channel regulation," "calcium channel dysregulation," "calcium channel disorder," "calcium channel condition," "calcium channel dysfunction," "calcium channel-related dysfunction," "calcium channel-related disease," or "calcium channel-related condition." A calcium channel-related disorder includes, but is not limited to, Alzheimer's disease, Huntington's Disease, Parkinson's disease, Tourette's syndrome, stroke, epilepsy, sleep or circadian rhythm disorder (e.g., insomnia), schizophrenia, depression, attention deficit disorder (ADD), attention deficit hyperactivity disorder (ADHD), drug abuse, pain, and cancer. A calcium channel-related disorder also includes, but is not limited to, a disease (e.g., Parkinson's disease) or a condition (e.g., addiction to cocaine) that involves an aberration or dysregulation of a signal transmission pathway, including, but not limited to, neurotransmission mediated by metabotropic glutamate receptors in excitable cells, tissues or organs (e.g., neurons, brain, central nervous system, etc.). A calcium channel-related disorder also includes, but is not limited to, a symptom of a calcium channel-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435–447 (1999); Bibb et al., Proc. Nat'l Acad. Sci. USA 97:6809–68 14 (2000); and U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "CKI-related disorder" is used interchangeably with the terms "CKI disorder," "CKI condition," "CKI dysfunction," "CKI-related dysfunction," "CKI-related disease," "CKI-related condition," "dysregulation of CKI function" or "CKI function dysregulation." A CKI-related disorder includes, but is not limited to, Alzheimer's disease, Huntington's Disease, Parkinson's disease, Tourette's syndrome, stroke, epilepsy, sleep or circadian rhythm disorder (e.g., insomnia), schizophrenia, depression, attention deficit disorder (ADD), attention deficit hyperactivity disorder (ADHD), drug abuse, pain, and cancer. A CKI-related disorder also includes, but is not limited to, a disease (e.g., Parkinson's disease) or a condition (e.g., addiction to cocaine) that involves an aberration or dysregulation of a signal transmission pathway, including, but not limited to, neurotransmission mediated by metabotropic glutamate receptors in excitable cells, tissues or organs (e.g., neurons, brain, central nervous system, etc.). A CKI-related disorder also includes, but is not limited to, a symptom of a CKI-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine or serine residues of DARPP-32 (see, e.g., Greengard et al., Neuron 23:435–447 (1999); Bibb et al., Proc. Nat'l Acad. Sci. USA 97:6809–68 14 (2000); and U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, the term "Cdk5-related disorder" is used interchangeably with the terms "Cdk5 disorder," "Cdk5 condition," "Cdk5 dysfunction," "Cdk5-related dysfunction," "Cdk5-related disease," "Cdk5-related condition," "dysregulation of Cdk5 function" or "Cdk5 function dysregulation." A Cdk5-related disorder includes, but is not limited to, Alzheimer's disease, Huntington's Disease, Parkinson's disease, Tourette's syndrome, stroke, epilepsy, sleep or circadian rhythm disorder (e.g., insomnia), schizophrenia, depression, attention deficit disorder (ADD), attention deficit hyperactivity disorder (ADHD), drug abuse, pain, and cancer. A Cdk5-related disorder also includes, but is not limited to, a disease (e.g., Parkinson's disease) or a condition (e.g., addiction to cocaine) that involves an aberration or dysregulation of a signal transmission pathway, including but not limited to neurotransmission mediated by metabotropic glutamate receptors in excitable cells, tissues or organs (e.g., neurons, brain, central nervous system, etc.). A Cdk5-related disorder also includes, but is not limited to, a symptom of a Cdk5-related disorder. In certain embodiments, the pathway affected includes the phosphorylation and/or dephosphorylation of DARPP-32, with the corresponding treatment of the dysregulation involving the stimulation and/or inhibition of the phosphorylation and/or dephosphorylation of one or more specific threonine and/or serine residues of DARPP-32 (see, e.g., Greengard et al., Neuron 23:435–447 (1999); Bibb et al., Proc. Nat'l Acad. Sci. USA 97:6809–68 14 (2000); and U.S. patent application Ser. Nos. 09/419,379, by Bibb et al., entitled "Methods of Identifying Agents That Regulate Phosphorylation/Dephos-phorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety).

As used herein, a "small organic molecule" is an organic compound (or organic compound complexed with an inorganic compound (e.g., metal)) that has a molecular weight of less than 3 kilodaltons, preferably less than 1.5 kilodaltons. Preferably, the small organic molecule can cross the blood-brain barrier.

As used herein, the term "about" means within 10 to 15%, preferably within 5 to 10%. For example an amino acid sequence that contains about 60 amino acid residues can contain between 51 to 69 amino acid residues, more preferably 57 to 63 amino acid residues.

4. DESCRIPTION OF THE FIGURES

FIG. 1. Activation by (S)-3,5-Dihydroxyphenylglycine (DHPG) of group I mGluR receptors increases phosphorylation of Thr75 and Ser137 on DARPP-32. Mouse neostriatal slices were treated with DHPG for various periods of time as indicated. Slice homogenates were analyzed by SDS-PAGE and immunoblotting with phospho-Thr75, phospho-Ser137 and total DARPP-32 antibodies. (a) Time course of treatment with DHPG (100 µM). (b) Slices were pre-incubated without or with the group I mGluR antagonist L-AP3 (100 µM) for 20 min prior to treatment with DHPG for 2 min. Cumulative data (means±SEM) obtained from 5 experiments are shown in the lower panels in (a) and (b). Data were normalized to values for untreated slices. *p<0.05, Student's t-test, compared with untreated slices. See Section 6 for details.

Figure 2:
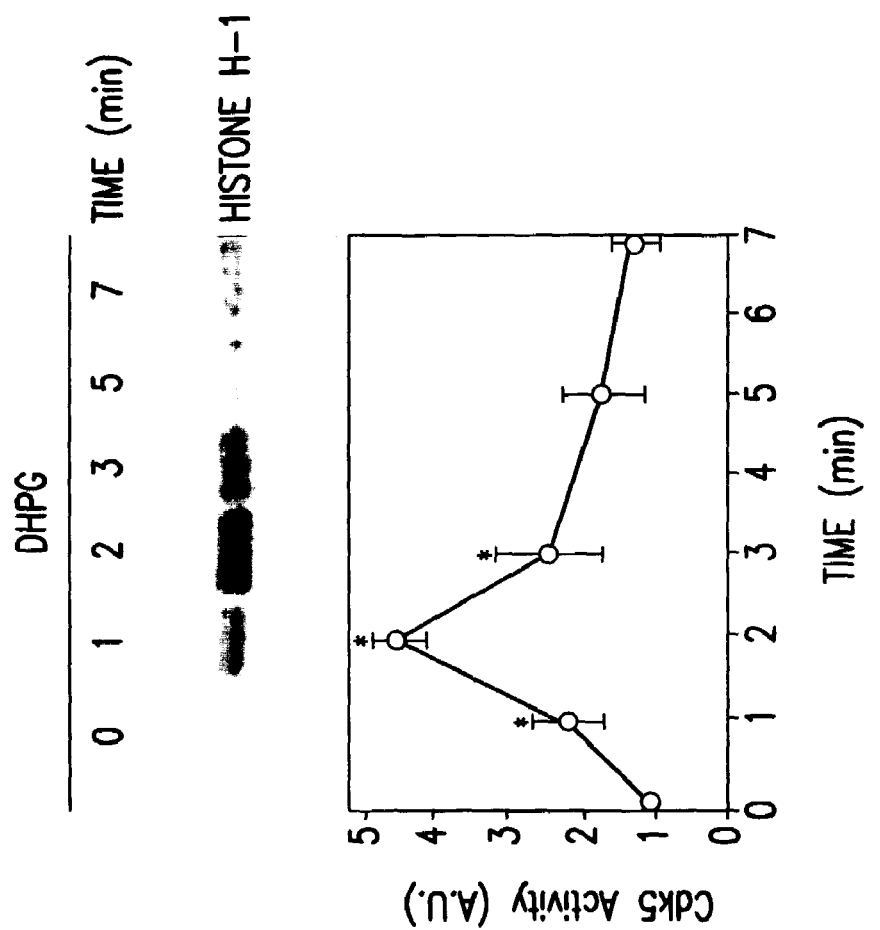

FIG. 2. Activation of mGluR1 receptors transiently increases Cdk5 activity. Mouse neostriatal slices were treated with DHPG for various period of time as indicated. Slices were homogenized and Cdk5 was immunoprecipitated using anti-Cdk5 (C-8) antibody. Cdk5 activity was assayed using Histone H-1 as substrate and samples were analyzed by SDS-PAGE and autoradiography. The upper panel shows an autoradiogram of histone H-1 phosphorylation and the lower panel shows cumulative data. The autoradiograms were analyzed using a Phospholmager. Data for three experiments (means±SEM) were normalized to the values obtained at 0 min. *p<0.05, Student's t-test, compared with 0 min. See Section 6 for details.

Figure 3:
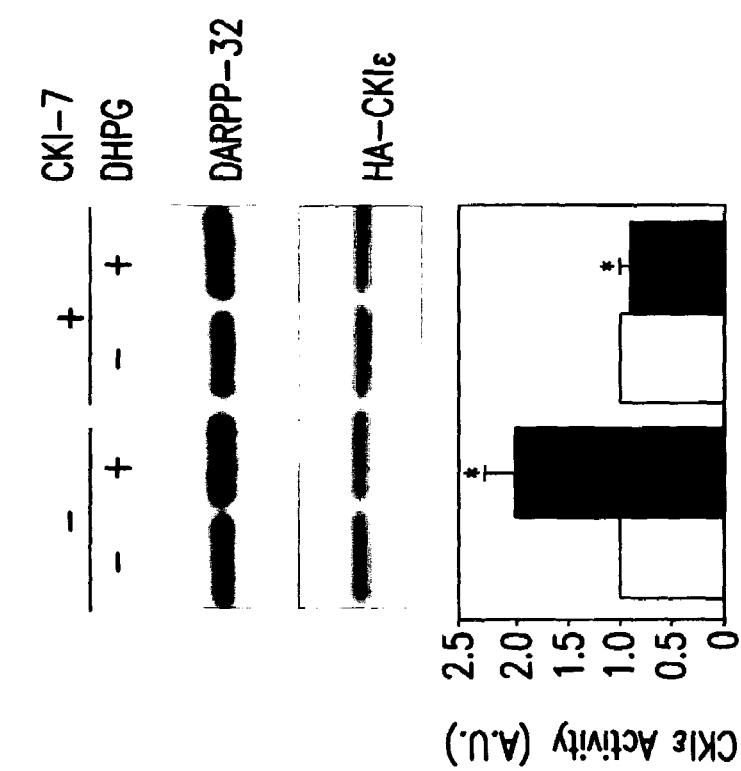

FIG. 3. Activation of mGluR1 receptors stimulates CK1ε activity. N2a cells were transiently transfected with HA-tagged CK1ε. Cells were pre-incubated without or with the CK1 inhibitor CK1-7 (100 µM) for 30 min prior to treatment with DHPG (100 µM) for a further 2 min. HA-CK1ε was immunoprecipitated and CK1 was assayed using DARPP-32 as a substrate. Samples were analyzed by SDS-PAGE and autoradiography. Upper panel: autoradiogram of DARPP-32 phosphorylation; Middle panel: immunoblot of the level of expression of HA-CK1ε; lower panel: cumulative data of kinase activity obtained from five experiments (means±SEM). Data were normalized to values obtained for untreated cells. *p<0.05, Student's t-test, compared with untreated cells. See Section 6 for details.

Figure 4:
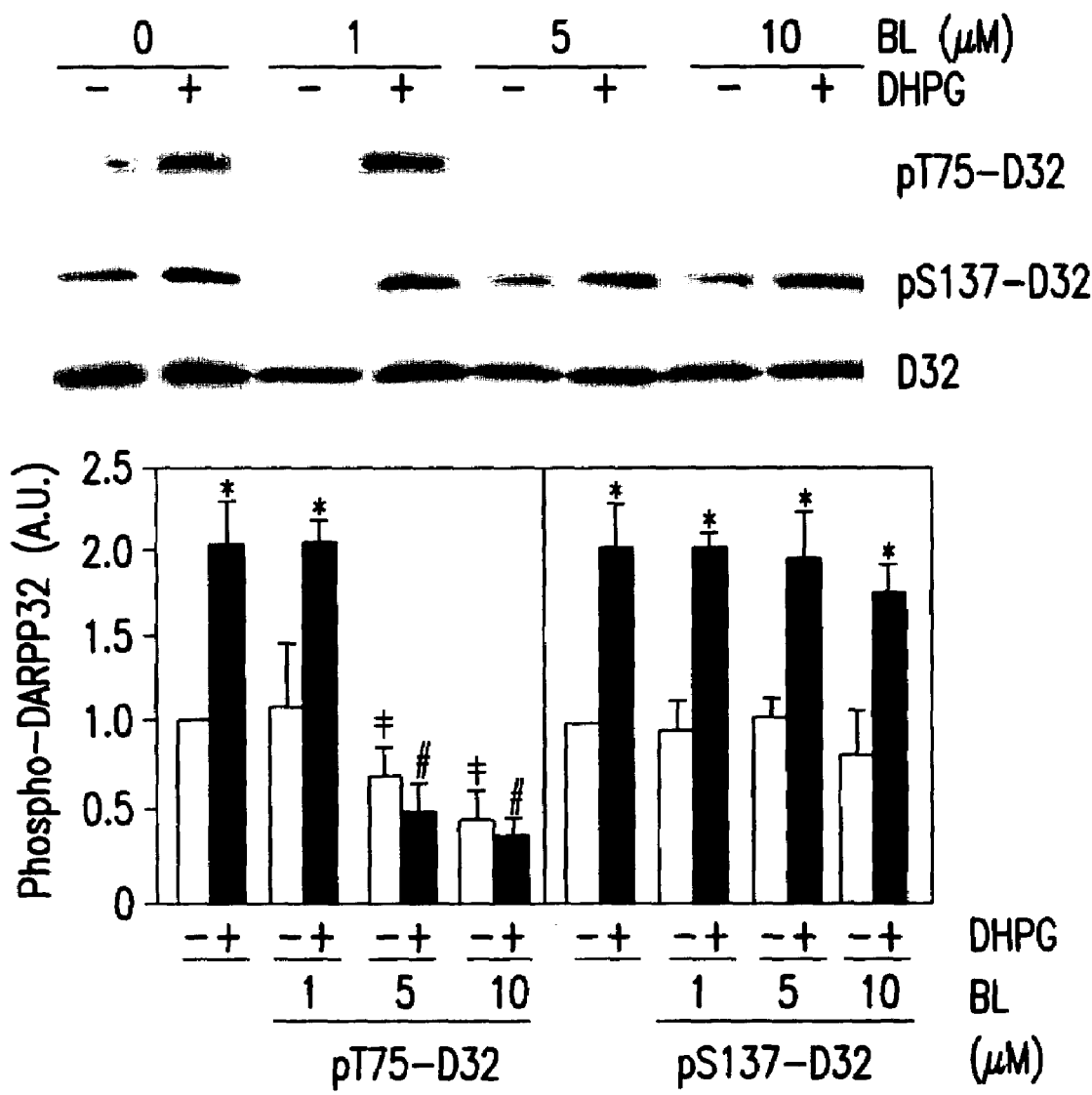

FIG. 4. A Cdk5 inhibitor, butyrolactone, blocks the effect of DHPG on phosphorylation of DARPP-32 on Thr75 (Cdk5 site) but not on Ser137 (CK1 site). Mouse neostriatal slices were pre-incubated with 0, 1, 5 or 10 µM butyrolactone (BL) for 30 min, and then DHPG (100 µM) was added for a further 2 min. Slice homogenates were analyzed by SDS-PAGE and immunoblotting with phospho-Thr75, phospho-Ser137 and total DARPP-32 antibodies. Immunoblots are shown in the upper panel, and cumulative data (means±SEM) obtained from three experiments are shown in the lower panel. Data were normalized to values obtained for untreated slices. *$p<0.05$, Student's t-test, compared with slices in the absence of DHPG; t$p<0.05$, student's t-test, compared with untreated slices; #$p<0.05$, Student's t-test, compared with slices treated with DHPG alone. See Section 6 for details.

Figure 5:
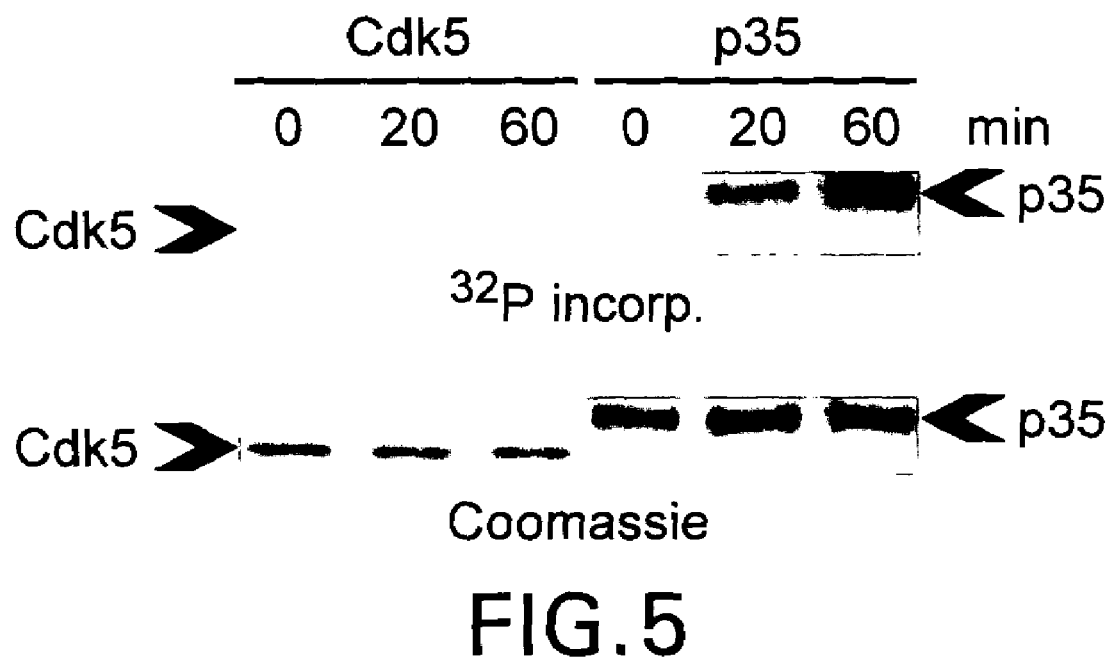

FIG. 5. CK1 phosphorylates p35 in vitro. Cdk5 (left) or p35 (right) was incubated in vitro with CK1 and $^{32}$P-ATP for various times as indicated. Samples were analyzed by SDS-PAGE and autoradiography. $^{32}$P incorporation is shown in the autoradiogram (upper panel). Total amounts of Cdk5 and p35 are shown in the Coomassie stained gel (lower panel). See Section 6 for details.

Figure 6B:
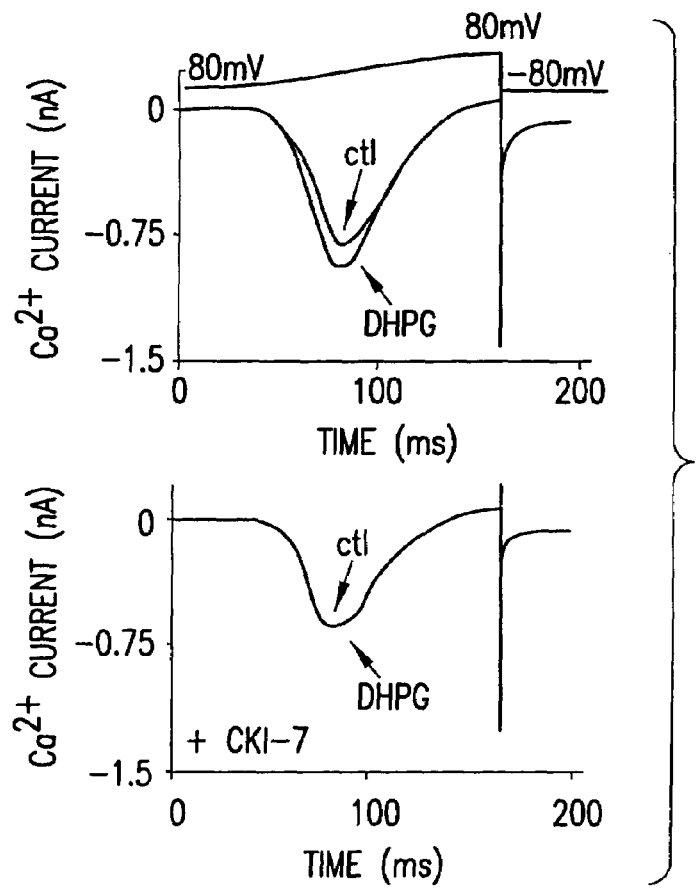

FIG. 6. Activation by DHPG of group I mGluR receptors enhances $Ca^{2+}$ current and this enhancement is blocked by inhibiting CK1 or Cdk5, and is absent in DARPP-32 KO mice. (a) and (c) Peak $Ca^{2+}$ current evoked by a voltage ramp protocol as a function of time and drug application. (a) DHPG (100 μM) increased $Ca^{2+}$ current. In the presence of CK1–7 (100 μM), basal $Ca^{2+}$ currents were reduced and the DHPG effect was attenuated. Washing out CK1–7 led to recovery of the DHPG effect. (c) DHPG (100 μM) increased $Ca^{2+}$ current. In the presence of butyrolactone (25 μM), basal $Ca^{2+}$ currents were reduced and the DHPG effect was eliminated. (b) and (d) Representative current traces showing the modulation by DHPG before and after the application of (b) CK1–7 or (d) butyrolactone (at time points denoted by *). Insets: Box plot summaries showing the percentage block of the DHPG effect on $Ca^{2+}$ currents by (a) CK1–7 and (c) butyrolactone. (e) Plot of peak $Ca^{2+}$ current as a function of time and agonist application in a representative neostriatal neuron from a DARPP-32 KO mouse. DHPG (100 μM) had no effect on $Ca^{2+}$ current in neurons from DARPP-32$^{-/-}$ mice (n=9). See Section 6 for details.

Figure 7:
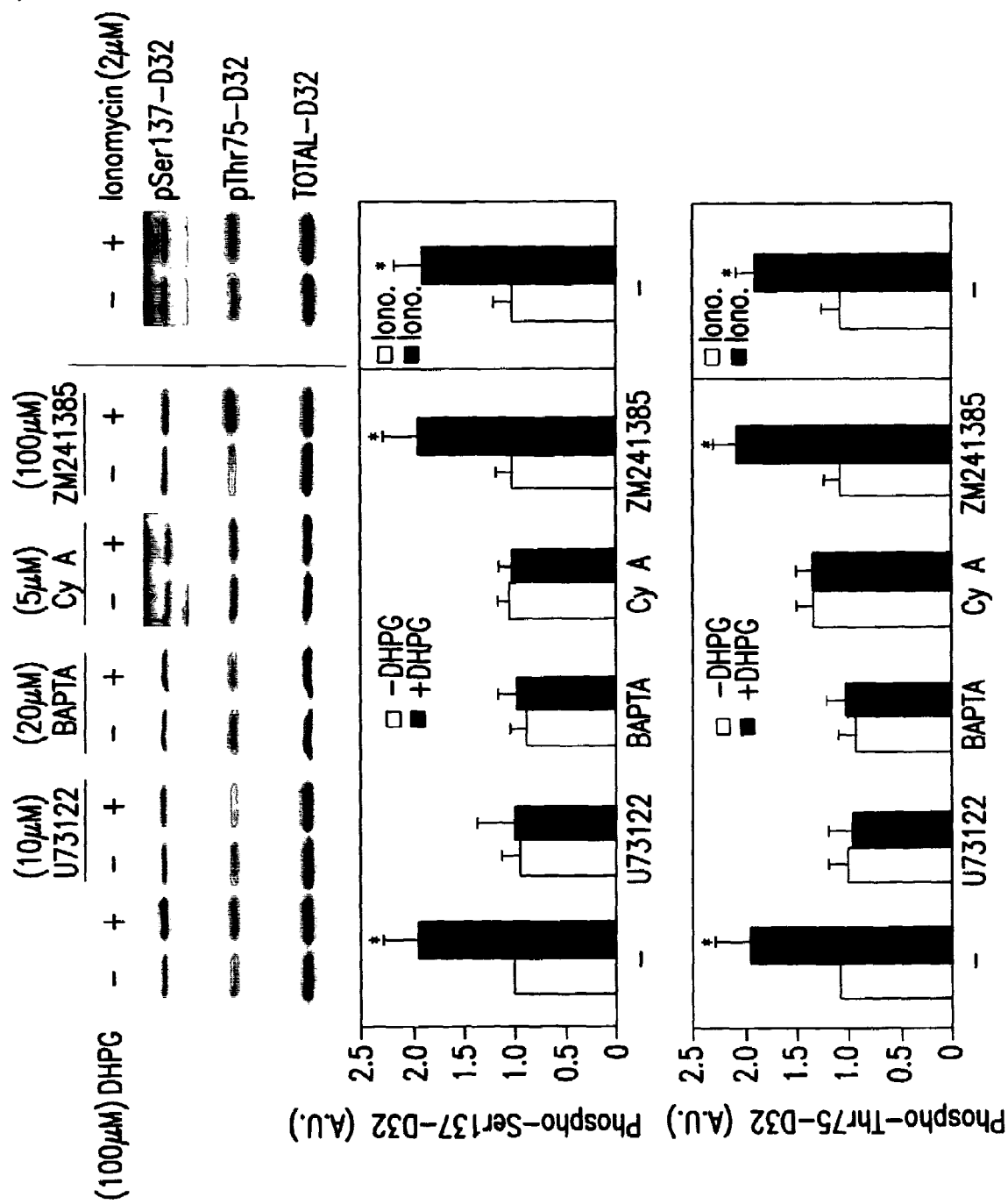

FIG. 7. The effect of (S)-3,5-Dihydroxyphenylglycine (DHPG) on DARPP-32 Ser-137 and Thr-75 phosphorylation is blocked by the PLCβ inhibitor U73122, the $Ca^{2+}$ chelator BAPTA/AM and the calcineurin inhibitor cyclosporin A. The effect of the mGluR group I agonist, DHPG, on phosphorylation of DARPP-32 at Ser-137 (CK1 site) and Thr-75 (Cdk5 site) was examined in mouse neostriatal slices using phosphorylation state-specific antibodies. Slices were treated with DHPG (100 μM) or ionomycin (Iono, 2 μM) for 2 min following pre-incubation with vehicle (left two lanes), U73122 (12.5 μM for 20 min), BAPTA/AM (BAPTA, 20 μM for 20 min), cyclosporin A (Cy A, 5 μM for 60 min), or the adenosine A2a receptor antagonist ZM241385 (10 μM for 20 min), as indicated. Slices were homogenized and analyzed by SDS-PAGE and immunoblotting using phospho-Ser137, phospho-Thr75 and total DARPP-32 antibodies. Immunoblots are shown in the upper panels, and combined data (means±SEM) obtained from 3 experiments are shown in the lower panels. Data were normalized to values obtained for untreated slices. *$p<0.05$, Student's t-test, compared with untreated slices. See Section 7 for details.

Figure 8:
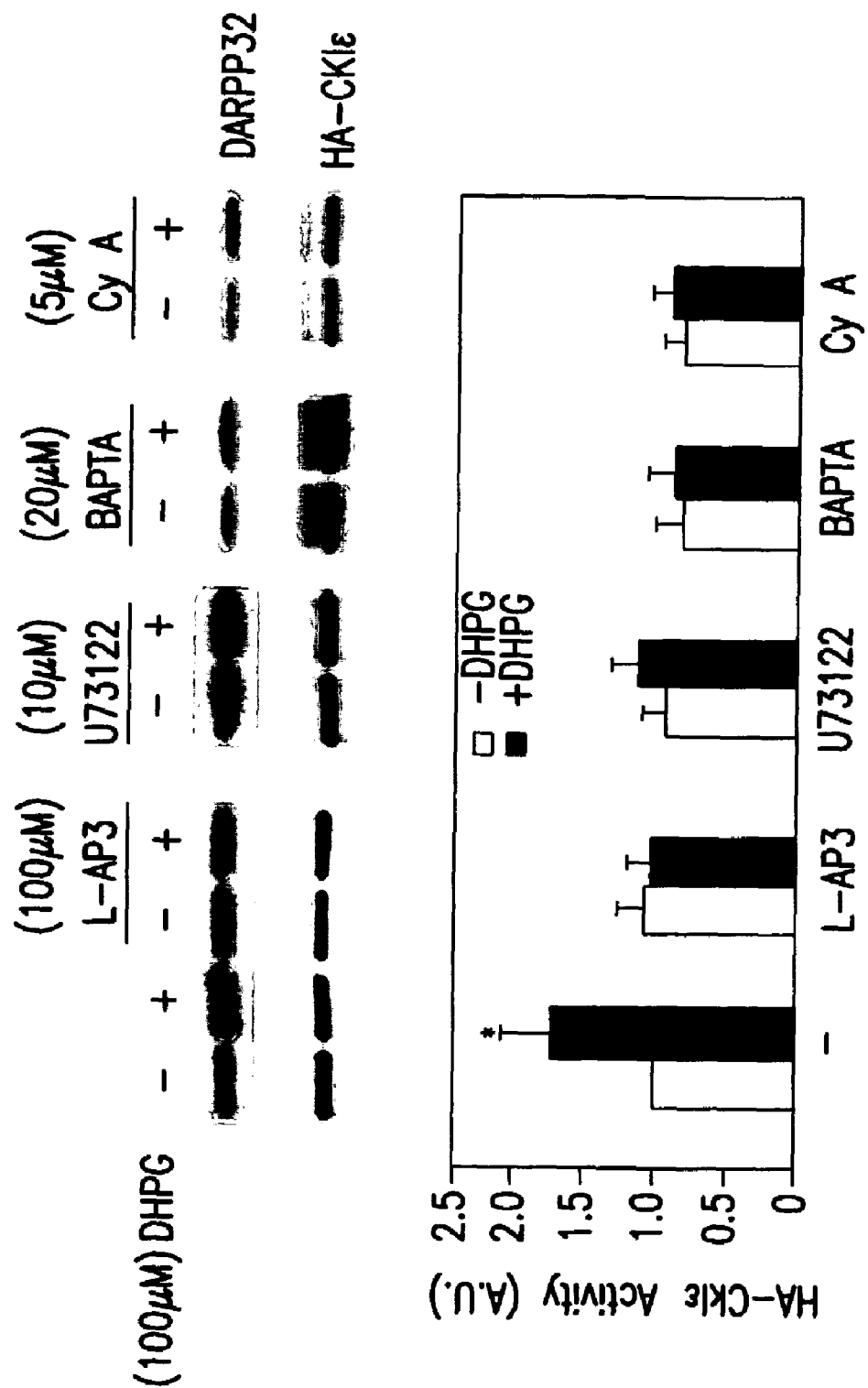

FIG. 8. The effect of DHPG on CK1ε activity is blocked by U73122, BAPTA/AM and cyclosporin A. N2a cells were transiently transfected with HA-tagged CK1ε. Cells were preincubated for 30 min without or with the group I mGluR antagonist L-AP3 (100 μM), U73122 (12.5 μM), BAPTA/AM (BAPTA, 20 μM), or cyclosporin A (Cy A, 1 μM) prior to treatment without or with DHPG (100 μM for 2 min). HA-CK1ε was immunoprecipitated and CK1 was assayed using DARPP-32 as substrate. Samples were analyzed by SDS-PAGE and autoradiography. Upper panel: autoradiogram of DARPP-32 phosphorylation; middle panel: immunoblot using HA antibody; lower panel: combined data obtained from 5 experiments (means±SEM). Data were normalized to values for untreated cells. *$p<0.05$, Student's t-test, compared with untreated cells. See Section 7 for details.

Figure 9:
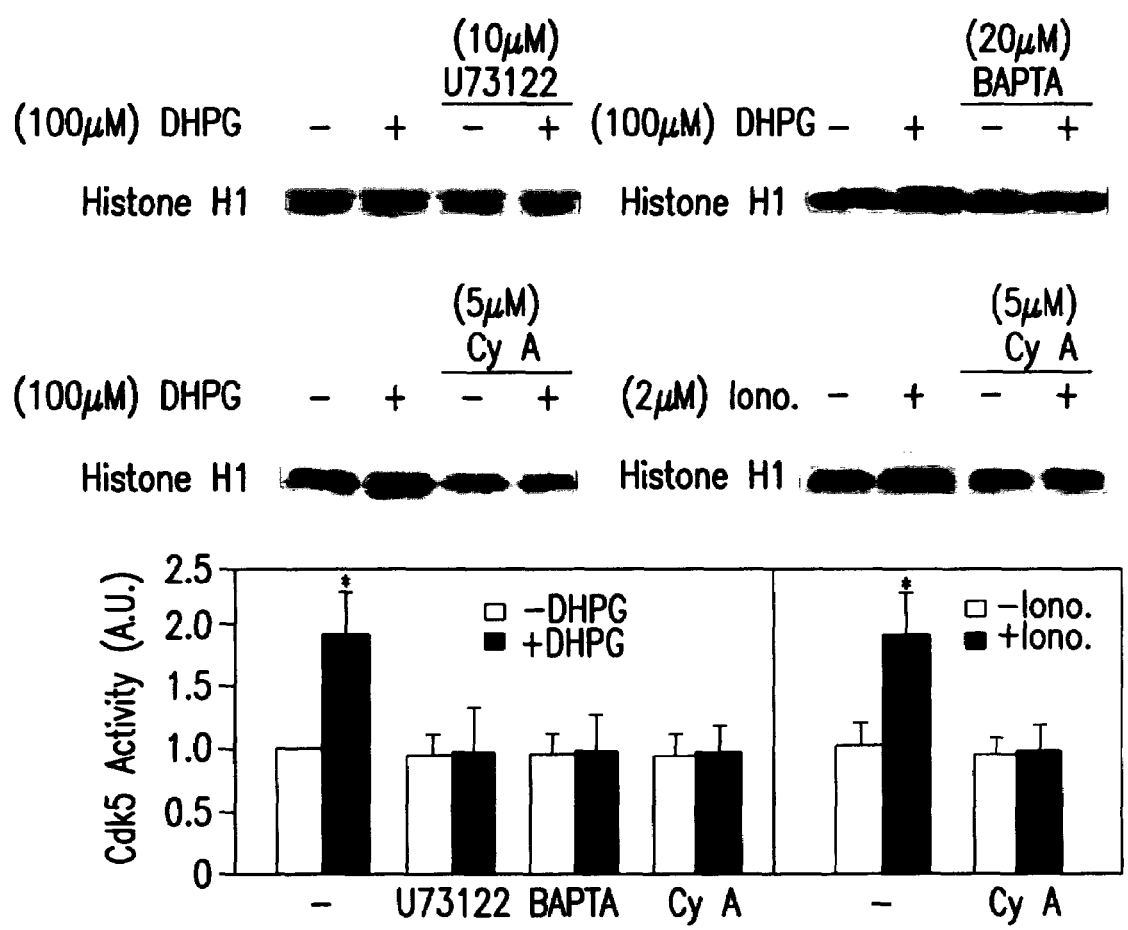

FIG. 9. The effect of DHPG on Cdk5 activity is blocked by U73122, BAPTA/AM and cyclosporin A. Mouse neostriatal slices were preincubated with U73122 (12.5 μM for 20 min), BAPTA/AM (BAPTA, 20 μM for 20 min) or cyclosporin A (Cy A, 5 μM for 60 min), and then without or with DHPG (100 μM for 2 min) or ionomycin (Iono, 2 μM for 2 min). Slices were homogenized and Cdk5 was immunoprecipitated with anti-Cdk5 (C-8) antibody. Cdk5 activity was assayed using histone H-1 as substrate, and samples were analyzed by SDS-PAGE and autoradiography. The upper and middle panels show autoradiograms indicating histone H-1 phosphorylation. The lower panel shows combined data (means±SEM) from 3 experiments. The autoradiograms were analyzed using a PhosphorImager, and the data were normalized to values obtained for untreated slices. *$p<0.05$ Student's t-test, compared with untreated slices. See Section 7 for details.

FIG. 10. CK1ε is transiently dephosphorylated upon DHPG treatment. N2a cells were transiently transfected with HA-CK1ε. Cells were incubated with 200 μCi/ml $H_3{}^{32}PO_4$ in phosphate-free medium for 2 h. For the last 30 min of labeling, cells were treated without or with cyclosporin A (Cy A, 1 μM), and then without or with DHPG for various times as indicated. (a) HA-CK1ε was immunoprecipitated and samples were analyzed by SDS-PAGE and autoradiography (upper panel). The lower panel shows an immunoblot using HA antibody. (b) Gel bands containing $^{32}$P-labeled HA-CK1ε were subjected to two-dimensional tryptic phosphopeptide mapping; electrophoresis was in the horizontal direction (positive electrode at left, origin marked by arrow) and chromatography was in the vertical direction. (c) Cells transfected with HA-CK1ε were incubated with cyclosporin A (Cy A) and DHPG for 0 or 4 min, as indicated. Cell extracts were analyzed as in (a) and (b). See Section 7 for details.

FIG. 11. A CK1ε mutant lacking inhibitory autophosphorylation sites is not activated by DHPG. N2a cells were transiently transfected with either wild-type HA-tagged CK1ε or Myc-tagged MM2-CK1ε, a mutant enzyme in which S323, T325, T334, T337, S368, S405, T407 and S408 are mutated to alanine. (a) Cells were labeled with 200 μCi/ml $H_3{}^{32}PO_4$ in phosphate-free medium for 2 h and treated with DHPG for 2 min. HA- or Myc-tagged CK1ε was immunoprecipitated, analyzed by SDS-PAGE and subjected to phosphopeptide mapping as disclosed in the legend to FIG. 10. (b) Cells were pre-treated without or with cyclosporin A (Cy A, 1 μM for 30 min) prior to incubation without or with DHPG (100 μM for 2 min). HA-CK1ε or MM2-CK1ε was immunoprecipitated and CK1ε activity was assayed using DARPP-32 as a substrate. Samples were analyzed by SDS-PAGE and autoradiography. Upper panel: autoradiogram of DARPP-32 phosphorylation; middle panel: immunoblot showing expression of HA- or Myc-tagged CK1ε using an anti-CK1 antibody that recognized both wild-type and MM2-CK1ε; lower panel: combined kinase activity data obtained from 5 experiments (mean+/− SEM). Data were normalized to values obtained for untreated cells. *$p<0.05$, Student's t-test, compared with untreated cells; #p<0.001, Student's t-test, compared with untreated cells that were transfected with wild-type HA-CK1ε. See Section 7 for details.

FIG. 12. Constitutive phosphorylation of CK1ε does not regulate enzyme activity. N2a cells were transfected with HA-CK1ε or MM2-CK1ε. (a) Cells were labeled with $H_3{}^{32}PO_4$ in phosphate-free medium (200 μCi/ml for 2 h) and then treated with DHPG for 2 min. HA-CK1ε or MM2-CK1ε were immunoprecipitated and incubated without or with lambda protein phosphatase for 15 min. $^{32}$P-labeled samples were analyzed by SDS-PAGE and autoradiography (upper panel). Other samples prepared in parallel were analyzed for CK1 activity using DARPP-32 as substrate (lower panel). (b) Combined kinase activity data obtained from 3 experiments (means+/−SEM). See Section 7 for details.

Figure 13:
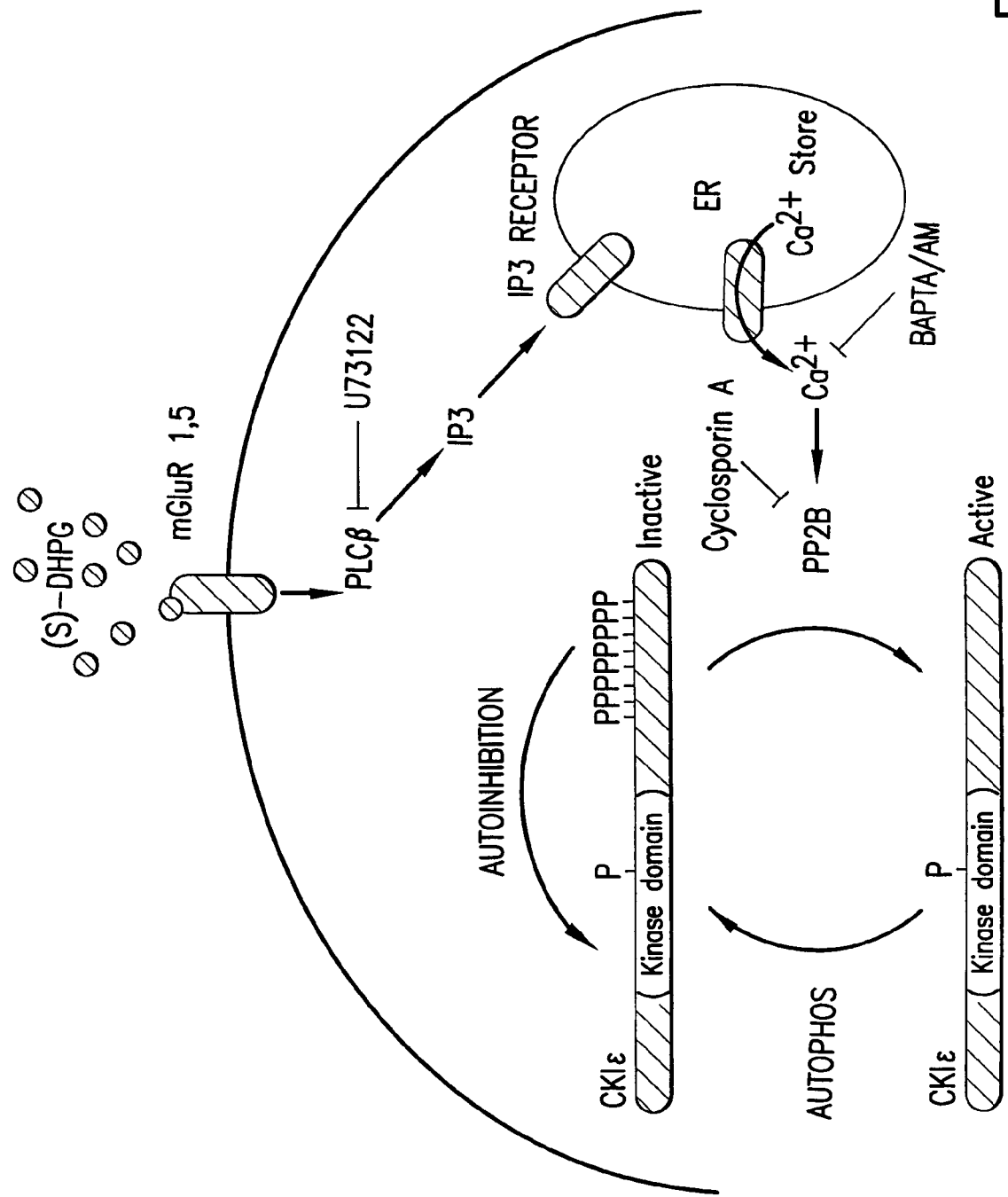

FIG. 13. Model for regulation of CK1 activity by activation of group I mGluRs. DHPG activates group I mGluRs that are coupled to PLCβ via Gq. Activation of PLCβ generates $IP_3$, $IP_3$ binds to $IP_3$ receptors on the endoplasmic reticulum and releases $Ca^{2+}$ into the cytosol. Elevated intracellular $Ca^{2+}$ activates the $Ca^{2+}$-dependent phosphatase calcineurin, which in turn dephosphorylates the eight regulatory autophosphorylation sites on CK1ε. CK1ε is transiently activated but gradual autophosphorylation restores the inhibited level of kinase activity. A site that is basally phosphorylated is likely to be present within the kinase catalytic domain but does not appear to regulate enzyme activity. See Section 7 for details.

5. DETAILED DESCRIPTION OF THE INVENTION

The present invention is based in part on the surprising discovery, on the part of the inventors, that both casein kinase I ("CKI" or "CK1") and cyclin-dependent kinase 5 (Cdk5) are part of the metabotropic glutamate receptor (mGluR) signaling pathway in neuronal tissues.

The present invention provides a method for modulating casein kinase I ("CKI" or "CK1") and/or cyclin-dependent kinase 5 ("Cdk5," "cdk5" or "CDK5") activity in a cell or tissue of interest, comprising contacting the cell or tissue of interest with an effective amount of a compound that alters the activity of a metabotropic glutamate receptor (mGluR) intracellular signaling molecule, wherein contact of the cell or tissue with the compound results in a modulation of the activity of casein kinase I or cyclin-dependent kinase 5.

The present invention provides a method for regulating activity of calcium channels comprising administering (for example, to an individual, patient or animal) an effective amount of a compound of the invention, for example, a compound identified by the methods of the invention, wherein the compound modulates the activity of casein kinase I (CKI) and/or cyclin-dependent kinase 5 (Cdk5), and wherein modulation of CKI or Cdk5 activity results in an alteration in the activity of calcium channels in the neuron. In a specific embodiment, the calcium channels are in an excitable cell, e.g., a neuron. In another embodiment, the method involves administration of a mGluR agonist in order to increase activity of CKI and Cdk5 and thereby alter activity of calcium channels.

The present invention provides, in vivo, in situ, and in vitro, methods of identifying an agent, drug or compound for modulating the activity of casein kinase I (CKI) and/or cyclin-dependent kinase 5 (Cdk5) in a cell or tissue of interest. Such methods can be used alone or in conjunction with each other. In one embodiment, the method comprises determining a first level of casein kinase I and/or cyclin-dependent kinase 5 activity in a cell or tissue of interest; contacting the cell or tissue with a test compound; and determining a second level of casein kinase I and/or cyclin-dependent kinase 5 activity in the cell or tissue, wherein a difference in the first level and the second level of casein kinase I and/or cyclin-dependent kinase 5 activity is indicative of the ability of the test compound to modulate casein kinase I and/or cyclin-dependent kinase 5 activity.

In another embodiment, the method comprises determining a first level of casein kinase I and/or cyclin-dependent kinase 5 activity in a cell or tissue of interest; determining a first level of calcium channel activity in the cell or tissue; contacting the cell or tissue with a test compound; determining a second level of casein kinase I and/or cyclin-dependent kinase 5 activity in the cell or tissue; and determining a second level of calcium channel activity in the cell or tissue, wherein a difference in the first level and the second level of casein kinase I and/or cyclin-dependent kinase 5 activity and a difference in the first level and the second level of calcium channel activity are indicative of the ability of the test compound to modulate the activity of calcium channels.

The present invention also provides in vivo methods of identifying agents that can modulate the activity of CKI or Cdk5. Such methods can be employed alone or in conjunction with in vitro and in situ methods as disclosed herein. One such method comprises administering the agent to a non-human mammal. The amount (and/or rate) of activation of CKI and/or Cdk5 is then determined. An agent is identified as capable of modulating the activity of CKI and/or Cdk5 when the amount (and/or rate) of activation is increased or decreased in the presence of the agent relative to in the absence of the agent. In preferred embodiments, the non-human mammal is a rodent. In a more preferred embodiment, the rodent is a mouse.

The invention also provides methods of screening potential agents (or drugs or compounds) in order to select an agent that can potentially ameliorate and/or be used in treatment of mGluR-related, CKI-related, Cdk5-related and/or calcium channel-related disorders.

The present invention also provides methods of identifying agents (or drugs or compounds), e.g., drug screening assays, which drugs may be used in therapeutic methods for the treatment of mGluR-related, CKI-related, Cdk5-related and/or calcium channel-related disorders.

The present invention also provides compositions for modulating the activity of casein kinase I (CKI) and/or cyclin-dependent kinase 5 (Cdk5). The invention also provides compositions for modulating the activity of calcium channels via modulation of the activity of casein kinase I (CKI) and/or cyclin-dependent kinase 5 (Cdk5).

The present invention further provides methods for performing rational drug design to develop drugs that can modulate activity of CKI and/or Cdk5 and thereby ameliorate mGluR-related, CKI-relate, Cdk5-related and/or calcium channel-related disorders.

In one embodiment, the invention provides methods of identifying a compound that modulates the activity of cyclin-dependent kinase 5 in a cell or tissue of interest comprising: (a) determining a first level of cyclin-dependent kinase 5 activity in said cell or tissue; (b) contacting said cell or tissue with a test compound; and (c) determining a second level of cyclin-dependent kinase 5 activity in said cell or tissue, wherein a difference in said first level and said second level of cyclin-dependent kinase 5 activity is indicative of the ability of said test compound to modulate cyclin-dependent kinase 5 activity, and wherein modulation of cyclin-dependent kinase 5 activity is regulated by modulation of the activity of metabotropic glutamate receptors.

The present invention also provides diagnostic and therapeutic methods for the treatment of a mGluR-related, CKI-related, Cdk5-related or calcium channel-related disorder, including, but not limited the use of compositions or compounds of the invention in the treatment of a mGluR-related, CKI-related, Cdk5-related or calcium channel-related disorder.

In one aspect, the invention provides a method for treating a neuronal condition characterized by an increase or a decrease in calcium channel activity (e.g., calcium channel currents) comprising administering to a subject in need of such treatment an effective amount of a compound of the present invention to modulate CKI and/or Cdk5 activity, and thus increase or decrease calcium channel activity via modulation of a mGluR signaling pathway. In one embodiment, the mGluR signaling pathway comprises: activation of mGluR1 receptors that stimulate G proteins that are coupled to PLCβ, activation of the $Ca^{2+}$/calmodulin-dependent phosphatase, calcineurin (PP2B), by $Ca^{2+}$ released from IP3-sensitive stores, dephosphorylation of the inhibitory autophosphorylation sites on CK1ε by calcineurin, resulting in an increase in kinase activity.

The present invention provides methods for treating a mGluR-related, CKI-related, Cdk5-related or calcium channel-related disorder in an individual (e.g., a patient) or an animal subject by administering an effective amount of a compound of the invention to modulate CKI and/or Cdk5 activity. In one embodiment, the agent promotes or increases the activity of CKI and/or Cdk5. In another embodiment, the agent inhibits or decreases the activity of CKI and/or Cdk5.

The invention provides methods of administering an agent (or drug or compound) of the invention that can ameliorate a symptom of a mGluR-related, CKI-relate, Cdk5-related and/or calcium channel-related disorder, disease and/or condition in a patient or subject exhibiting the symptom. In certain embodiments, the invention provides methods of administering an agent identified by the methods disclosed herein, that can ameliorate a symptom of a mGluR-related, CKI-related, Cdk5-related or calcium channel-related disorder in a patient or subject exhibiting the symptom. In other embodiments, an agonist of mGluR activity can be used to for treating a mGluR-related, CKI-related, Cdk5-related or calcium channel-related disorder. In yet other embodiments, an antagonist of mGluR activity can be used to for treating a mGluR-related, CKI-related, Cdk5-related or calcium channel-related disorder.

The present invention also provides compositions for modulating the activity of casein kinase I (CKI) and/or cyclin-dependent kinase 5 (Cdk5). The invention also provides compositions for modulating the activity of calcium channels via modulation of the activity of casein kinase I (CKI) and/or cyclin-dependent kinase 5 (Cdk5).

The present invention also provides pharmaceutical compositions of the agents (or drugs or compounds) of the invention disclosed herein. The invention encompasses pharmaceutical compositions for regulating CKI and/or Cdk5 activity, and for diagnosing or treating a mGluR-related, CKI-related, Cdk5-related or calcium channel-related disorder. Because a loss of normal function results in the development of a phenotype of the above-listed diseases or disorders, activation of the metabotropic glutamate receptor (mGluR) signaling pathway, or an increase in CKI and/or Cdk5 activity (e.g., downstream activation) facilitates amelioration of a symptom in individuals exhibiting a symptom of such a disorder.

For clarity of disclosure, and not by way of limitation, the detailed description of the invention is divided into the subsections set forth below.

5.1. METHODS FOR MODULATING THE ACTIVITY OF CKI OR CDK5

The present invention provides a method for modulating casein kinase I (CKI) and/or cyclin-dependent kinase 5 (Cdk5) activity in a cell or tissue of interest comprising contacting the cell or tissue of interest with an effective amount of a compound that alters the activity of a metabotropic glutamate receptor (mGluR) intracellular signaling molecule, wherein contact of the cell or tissue with the compound results in a modulation of the activity of casein kinase I and/or cyclin-dependent kinase 5. A cell or tissue may include, but not be limited to: an excitable cell, e.g., a sensory neuron, motorneuron, or interneuron; a glial cell; a primary culture of neuronal or glial cells; cell(s) derived from a neuronal or glial cell line; dissociated cell(s); whole cell(s); permeabilized cell(s); a cellular extract or purified enzyme preparation; and a tissue or organ, e.g., brain, brain slice, spinal cord, spinal cord slice, central nervous system, peripheral nervous system, or nerve. In a specific embodiment, the activity of CKI and/or Cdk5 is increased. In another specific embodiment, the activity of CKI and/or Cdk5 is decreased.

In one embodiment, the invention provides methods of modulating the activity of casein kinase I (CKI) and/or cyclin-dependent kinase 5 (Cdk5) via the modulation of the activity of metabotropic glutamate receptors. In a specific embodiment, the metabotropic glutamate receptor is a group I metabotropic glutamate receptor. In another embodiment, the invention provides methods of modulating the activity of calcium channels via modulation of the activity of casein kinase I (CKI) and/or cyclin-dependent kinase 5 (Cdk5).

In one embodiment, a method is provided for modulating CKI or Cdk5 activity in cells or tissues of interest in vitro. In another embodiment, CKI or Cdk5 activity in cells or tissues of interest is modulated in vivo. The in vitro and in vivo applications may include, but are not limited to modulating activity in whole animals, in tissue slices, in broken cell preparations, in intact cells, and in isolated and purified cell preparations.

According to the present invention, the compounds of the invention may be mGluR agonists or antagonists but also may be compounds that act at levels of the mGluR intracellular signaling pathway other than at the level of the metabotropic glutamate receptor. As a result, the present invention also includes, in certain embodiments, compositions identified by screening for compounds that act at levels of the mGluR intracellular signaling pathway other than at the level of the metabotropic glutamate receptor. One of skill would understand that once identified as capable of modulating CKI and/or Cdk5 activity in the method of the present invention, the compound may be used therapeutically to modulate CKI and Cdk5 activity in neuronal cells in order to treat conditions in which CKI and Cdk5 activity may be involved. Such conditions include, but are not limited to, mGluR-related disorders and calcium-channel related disorders.

The present invention provides a method for regulating activity of calcium channels comprising administering (for example, to an individual, patient or animal) an effective amount of a compound, for example, a compound identified by the methods of the invention, wherein modulation of casein kinase I or cyclin-dependent kinase 5 activity results in an alteration in the activity of calcium channels in the neuron. In one embodiment, the calcium channels are in an excitable cell, e.g., a neuron. In another embodiment, the method involves administration of a mGluR agonist in order to increase activity of CKI and Cdk5 and thereby alter activity of calcium channels.

Without wishing to be bound by any particular theory, in one aspect of the invention, activation of mGluR1 receptors stimulates G proteins that are coupled to PLCβ, $Ca^{2+}$ released from IP3-sensitive stores activates the $Ca^{2+}$/calmodulin-dependent phosphatase, calcineurin (PP2B), and calcineurin then dephosphorylates the inhibitory autophosphorylation sites on CKI. Dephosphorylation of CKI results in an increase in kinase activity. Therefore, in one embodiment of the invention, the invention provides methods of modulating the activity or expression of CKI through the modulation of activity of calcineurin (PP2B).

5.2. METHODS FOR SCREENING FOR COMPOUNDS THAT MODULATE THE ACTIVITY OF CKI OR CDK5

The present invention provides methods of identifying an agent (or drug or compound) that modulates the activity of casein kinase I (CKI) and/or cyclin-dependent kinase 5 (Cdk5) in a cell or tissue of interest. In one embodiment, the invention provides methods of identifying an agent that modulates the activity of casein kinase I (CKI) and/or cyclin-dependent kinase 5 (Cdk5) via the modulation of the activity of metabotropic glutamate receptors. In a specific embodiment, the metabotropic glutamate receptor is a group I metabotropic glutamate receptor. In another embodiment, the invention provides methods of identifying an agent that modulates the activity of calcium channels via modulation of the activity of casein kinase I (CKI) and/or cyclin-dependent kinase 5 (Cdk5). A cell or tissue may include, but not be limited to: an excitable cell, e.g., a sensory neuron, motorneuron, or interneuron; a glial cell; a primary culture of neuronal or glial cells; cell(s) derived from a neuronal or glial cell line; dissociated cell(s); whole cell(s); permeabilized cell(s); a cellular extract or purified enzyme preparation; and a tissue or organ, e.g., brain, brain slice, spinal cord, spinal cord slice, central nervous system, peripheral nervous system, or nerve. In certain embodiments, activity of CKI encompasses expression of CKI and/or activity of Cdk5 encompasses expression of Cdk5.

As would be clearly understood by a person of ordinary skill in the art, any and/or all of the embodiments disclosed herein for identifying an agent, drug or compound that can modulate the activity of CKI or Cdk5, including such procedures that incorporate rational drug design, as disclosed herein, can be combined to form additional drug screens and assays, all of which are contemplated by the present invention.

In one embodiment, the method comprises determining a first level of casein kinase I and/or cyclin-dependent kinase 5 activity in a cell or tissue of interest; contacting the cell or tissue with a test compound; and determining a second level of casein kinase I and/or cyclin-dependent kinase 5 activity in the cell or tissue, wherein a difference in the first level and the second level of casein kinase I and/or cyclin-dependent kinase 5 activity is indicative of the ability of the test compound to modulate casein kinase I and/or cyclin-dependent kinase 5 activity.

In another embodiment, the method comprises determining a first level of casein kinase I and/or cyclin-dependent kinase 5 activity in a cell or tissue of interest; determining a first level of calcium channel activity in the cell or tissue; contacting the cell or tissue with a test compound; determining a second level of casein kinase I and/or cyclin-dependent kinase 5 activity in the cell or tissue; and determining a second level of calcium channel activity in the cell or tissue, wherein a difference in the first level and the second level of casein kinase I and/or cyclin-dependent kinase 5 activity and a difference in the first level and the second level of calcium channel activity are indicative of the ability of the test compound to modulate the activity of calcium channels.

In another embodiment, the invention provides a method of identifying a compound that modulates the activity of cyclin-dependent kinase 5 in a cell or tissue of interest comprising:(a) determining a first level of cyclin-dependent kinase 5 activity in said cell or tissue; (b) contacting said cell or tissue with a test compound; and (c) determining a second level of cyclin-dependent kinase 5 activity in said cell or tissue, wherein a difference in said first level and said second level of cyclin-dependent kinase 5 activity is indicative of the ability of said test compound to modulate cyclin-dependent kinase 5 activity, and wherein modulation of cyclin-dependent kinase 5 activity is regulated by modulation of the activity of metabotropic glutamate receptors.

In another embodiment, the invention provides a method of identifying a compound that modulates the activity of cyclin-dependent kinase 5 in a cell or tissue of interest comprising contacting said cell or tissue with a test compound, determining a level of cyclin-dependent kinase 5 activity in said cell or tissue, wherein a difference in said level and a standard or baseline level of cyclin-dependent kinase 5 activity in a comparable cell or tissue not contacted with the test compound is indicative of the ability of said test compound to modulate cyclin-dependent kinase 5 activity, and wherein modulation of cyclin-dependent kinase 5 activity is regulated by modulation of the activity of metabotropic glutamate receptors.

The invention also provides methods of screening agents (or drugs or compounds) to select an agent that can potentially ameliorate and/or be used in treatment of mGluR-related disorders and/or calcium channel-related disorders.

The present invention also provides methods of identifying agents, e.g., drug screening assays that can be used in therapeutic methods for the treatment of mGluR-related or calcium channel-related disorders.

The present invention also provides in vivo methods of identifying agents that can modulate the activity of CKI or Cdk5. Such methods can be employed alone or in conjunction with in vitro and in situ methods as disclosed herein. One such method comprises administering the agent to a non-human mammal. The amount (and/or rate) of activation of CKI and/or Cdk5 is then determined. An agent is identified as capable of modulating the activity of CKI and/or Cdk5 when the amount (and/or rate) of activation is increased or decreased in the presence of the agent relative to in the absence of the agent. In preferred embodiments, the non-human mammal is a rodent. In a more preferred embodiment, the rodent is a mouse.

In other embodiments, the agent is administered along with a mGluR agonist. The amount (and/or rate) of activation of CKI and/or Cdk5 is then determined. Since the administration of the mGluR agonist in the absence of the agent results in an increase in the CKI and/or Cdk5, an agent is identified as capable of modulating the activity of CKI and/or Cdk5 when the amount (and/or rate) of activation is significantly increased or decreased in the presence of the agent relative to in the absence of the agent. The in vivo method can further comprise administering the agent to a non-human mammal. Such animal models are disclosed in Section 5.5.

In a specific embodiment, the animal model is a homozygous DARPP-32 knockout mouse (see U.S. Pat. No. 5,777,195, by Fienberg et al., issued Jul. 7, 1998; U.S. Pat. No. 6,013,621, by Nishi et al., issued Jan. 11, 2000; and Fienberg et al., 1998, Science 281:838–842; each of which is incorporated herein by reference in its entirety). In one embodiment, the homozygous DARPP-32 knockout mouse may be used, in an additional test or assay to validate or confirm that a candidate agent modulates CKI and/or Cdk5 activity. In a specific embodiment, the validation may be carried out according to the methods described in Nishi et al. (U.S. Pat. No. 6,013,621, issued Jan. 11, 2000). When such an agent is identified that modulates the activity of CKI and/or Cdk5 via DARPP-32 phosphorylation, the presence of or administration of the agent in the DARPP-32 knockout mouse should not significantly increase or decrease the amount (and/or rate) of activation of calcium channels relative to the absence or non-administration of the agent.

In certain embodiments, combinatorial libraries of chemical compounds, based on different structural skeletons (e.g., purines), as well as unrelated naturally occurring compounds, can be tested as drug candidates. In a preferred embodiment of this type, the assay is performed using high throughput technology with automated robotic technology as disclosed herein. Positive results ("hits") represent either the reduced or increased activity of CKI and/or Cdk5, as compared to the control reactions (in which the drug candidate is not included in the assay).

Once a drug candidate is selected, structural variants of the drug candidate can be tested. These compounds can also be scrutinized and modified with parameters such as membrane permeability, specificity of effects, and toxicity. The selected (e.g., the most potent) compounds of this secondary screening can then be evaluated in situ and in animal models (see Section 5.5) to determine whether the selected compounds alter the activity of CKI and/or Cdk5 and/or calcium channels, and/or induce predicted behavioral alterations with minimal to no side-effects. Such behavioral abnormalities may include, but not be limited to, testing locomotor activity, e.g., administration of drugs of abuse to mice result in increased locomotor activity (see, e.g., Kosten et al., J. Pharmacol., Exp. Ther. 269:137–144 (1994); U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety); and/or self-administration of selected drugs or in prepulse inhibition (see, e.g., U.S. Pat. No. 5,777,195 Issued Jul. 7, 1998, incorporated herein by reference in its entirety). These tests can be then be followed by human trials in clinical studies. Alternatively, in certain embodiments, human trials in clinical studies can be performed without animal testing. Compounds affecting targets other than CKI or Cdk5 can also be similarly screened, using alternative targets exemplified below.

Alternatively, modulators of CKI and/or Cdk5 activity (e.g., activators or inhibitors of CKI or Cdk5) can be obtained by screening, e.g., a random peptide library produced by recombinant bacteriophage (see, e.g., Scott and Smith, Science 249:386–390 (1990); Cwirla et al., Proc. Natl. Acad. Sci. USA 87:6378–6382 (1990); Devlin et al., Science 249:404–406 (1990)) or a chemical library. Using the "phage method" very large libraries can be constructed ($10^6$–$10^8$ chemical entities). A second approach may be to use chemical methods, of which the Geysen method (Geysen et al., Molecular Immunology 23:709–715 (1986); Geysen et al. J. Immunologic Method 102:259–274 (1987)) and the method of Fodor et al. (Science 251:767–773 (1991)) are examples. Furka et al. (14*th international Congress of Biochemistry, Volume* 5, Abstract FR:013 (1988); Furka, Int. J. Peptide Protein Res. 37:487–493 (1991)), Houghton (U.S. Pat. No. 4,631,211, issued December 1986) and Rutter et al. (U.S. Pat. No. 5,010,175, issued Apr. 23, 1991) disclose methods to produce a mixture of peptides that can be tested as modulators of CKI and/or Cdk5 activity.

In another aspect, synthetic libraries (Needels et al., Proc. Natl. Acad. Sci. USA 90:10700–4 (1993); Ohlmeyer et al., Proc. Natl. Acad. Sci. USA 90:10922–10926 (1993); Lam et al., International Patent Publication No. WO 92/00252; Kocis et al., International Patent Publication No. WO 94/28028, each of which is incorporated herein by reference in its entirety), and the like can be used to screen for modulators of CKI and/or Cdk5 and/or calcium-channel activation, according to the present invention. Once a potential modulator is identified, chemical analogues can be either selected from a library of chemicals as are commercially available (e.g., from Chembridge Corporation, San Diego, Calif. or Evotec OAI, Abingdon, UK), or alternatively synthesized de novo. The prospective agent (drug) can be placed into any standard assay to test its effect on the activity of CKI and/or Cdk5 and/or calcium-channel activation. A drug is then selected that modulates the activity of CKI and/or Cdk5 and/or calcium-channel activation.

The present invention also contemplates screens for small molecules, analogs thereof, as well as screens for natural modulators of CKI and/or Cdk5, such as those that bind to and inhibit mGluR, CKI or Cdk5 in vivo. Alternatively, natural products libraries can be screened using assays of the invention for molecules that modulate mGluR, CKI and/or Cdk5 activity.

In one particular assay the target e.g., mGluR, CKI or Cdk5 can be attached to a solid support. Methods for placing such targets on the solid support are well known in the art and include such things as linking biotin to the target and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the target can be determined. Alternatively, or in addition, the dissociation constant between the labeled potential modulator and the target, for example, can be determined. Suitable labels for either the target or the potential modulator are disclosed herein.

In another aspect of the present invention, a potential modulator can be assayed for its ability to modulate the phosphorylation of Thr75 DARPP-32 or a fragment of DARPP-32 comprising Threonine-75 by Cdk5 (i.e., the Cdk5-Nck5a complex) either independently, or subsequent to a binding assay as disclose herein. In one such embodiment, the amount and/or rate of phosphorylation of Thr75 DARPP-32, or a fragment of DARPP-32 comprising the threonine-75 residue, is determined. Such assays are disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety.

Thus, a modulator that inhibits, or in the alternative stimulates, phosphorylation of DARPP-32 is then selected. In a particular embodiment, the effect of a potential modulator on the catalytic activity is determined. The potential modulator can then be tested for its effect on the physiological consequence of PKA inhibition by phospho-Thr75 DARPP-32. For this purpose, voltage-gated $Ca^{2+}$ currents, (which are known to be regulated by PKA) can be analyzed using patch-clamp recordings of dissociated striatal neurons. Such methods are disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety.

In another embodiment, a potential modulator can be added to a striatal tissue slice (as disclosed in Sections 6 and 7). Tissue samples can be treated with various concentrations of a potential modulator and the sample can then be analyzed for activity of CKI and/or Cdk5. Potential modulators of the activity of CKI and/or Cdk5 can be tested for example, on intact neurons in situ by treatment of acutely prepared neostriatal slices incubated in Kreb's bicarbonate buffer solution containing the reagent. The effects of these compounds can be tested by empirically defining the optimal concentration and time of incubation.

In another embodiment, an animal model (see Section 5.5) can be used to ascertain the effect of a potential agent on a mGluR-related condition. A potential modulator that ameliorates the mGluR-related condition can then be selected. For example, locomotor behavioral response of the animal can be determined in the presence and absence of the agent.

Methods of testing a potential therapeutic agent (e.g., a candidate drug, potential modulator, etc.) in an animal model are well known in the art. Thus potential therapeutic agents can be used to treat whole animals. The potential modulators can be administered by a variety of ways including topically, orally, subcutaneously, or intraperitoneally (such as by intraperitoneal injection) depending on the proposed use. Optimal dose will be empirically defined. Animals can be sacrificed by focused microwave beam irradiation, for example.

In a specific embodiment, homogenates of striatal tissue are subjected to immunoblot analysis. An alternative approach that can be employed assesses the potential efficacy of these compounds in relieving mGluR-related pathological symptoms in animal models for disease. For example, animals ectopically expressing the human disease causing form of the Huntington's disease (HD) gene exhibit neuropathalogical symptoms similar to those of HD patients. Models such as these can be used to assess the efficacy of any potential therapeutic agents (see Section 5.5). Generally, at least two groups of animals are used in the assay, with at least one group being a control group in which the administration vehicle is administered without the potential modulator.

5.2.1. ENZYMATIC ASSAYS FOR KINASES AND PHOSPHATASES

According to the methods of the invention, inhibitors of CK1 or Cdk5 can be identified by direct assay of isolated enzyme. Activities of kinase (e.g., CK1 or Cdk5) can be monitored by a variety of methods known to those skilled in the art, e.g., the methods disclosed in Parker, Law, et al., 2000, Development of high throughput screening assays using fluorescence polarization: nuclear receptor-ligand-binding and kinase/phosphatase assays, J. Biomolec. Screening 5(2): 77–88; Bader et al. (2001, Journal of Biomolecular Screening 6(4): 255–64); Liu, F., X. H. Ma, et al. (2001). "Regulation of cyclin-dependent kinase 5 and casein kinase 1 by metabotropic glutamate receptors." Proceedings of the National Academy of Sciences of the United States of America 98(20): 11062–8; Evans, D. B., K. B. Rank, et al. (2002). "A scintillation proximity assay for studying inhibitors of human tau protein kinase II/Cdk5 using a 96-well format." Journal of Biochemical & Biophysical Methods 50(2–3): 151–61.

Using such methods, samples containing the kinase of interest are exposed under the appropriate conditions to radioactive ATP and a synthetic peptide substrate of the appropriate composition to provide a site for phosphorylation. The radioactive phosphate newly associated with the peptide is then measured. Addition of a chemical moiety, such as biotin covalently linked to the substrate peptide, allows binding of the substrate peptide by a streptavidin-coated bead. Bead-bound peptide can be isolated and associated radioactivity measured, or, preferably, radioactivity associated with the substrate peptide can be measured directly using a bead suitable for scintillation proximity assays.

Modulators of CK1 or Cdk5 can also be identified by screening for modulators of DARPP-32 phosphorylation, i.e., Ser137 DARPP-32 phosphorylation (CK1) or Thr75 DARPP-32 phosphorylation (Cdk5). Such methods are disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, each of which is incorporated herein by reference in its entirety.

Phosphorylation of a peptide substrate can also be detected via direct binding of phosphospecific antibodies or by measuring displacement of a phosphospecific antibody from a competitor phosphopeptide (see, e.g., Parker, Law et al., 2000, Development of high throughput screening assays using fluorescence polarization: nuclear receptor-ligand-binding and kinase/phosphatase assays, J. Biomolec. Screening 5(2): 77–88). Fluorescence methods such as fluorescence resonance energy transfer (FRET) or fluorescence polarization (FP) can be used to detect the specific phosphopeptide-antibody complexes. These methods have the advantage that they employ "homogeneous" detection that is not dependent on isolation of the bound species, but rather depends on changes in fluorescence that occur owing to specific binding in solution. Methods of producing phosphospecific antibodies are well known in the art.

In one embodiment, the methods disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, (each of which is incorporated herein by reference in its entirety) are used to produce phosphorylation state-specific antibodies having specificity for Thr75-phosphorylated or Ser137-phosphorylated DARPP-32.

Fluorescence resonance energy transfer, or FRET, is widely used for homogeneous assays capable of detecting specific binding of macromolecules. FRET depends on the ability of excited "donor" fluorescent molecules (fluorophores) to transfer their energy to nearby "acceptor" fluorophores rather than emitting light. Thus, when the two fluorophores are brought together in space by binding to a substrate target, fluorescence emitted at the normal donor wavelength is reduced and fluorescence emitted by the acceptor fluorophore increases. Either the decrease in donor fluorescence or the increase in acceptor fluorescence can be used to measure the binding event.

In one embodiment, the methods disclosed in Bader et al. (2001, A cGMP-dependent protein kinase assay for high throughput screening based on time-resolved fluorescence resonance energy transfer, Journal of Biomolecular Screening 6(4): 255–64) are used to determine kinase activity. Bader et al. discloses a cGMP-dependent protein kinase assay for high throughput screening based on time-resolved fluorescence resonance energy transfer ("FRET"). Samples containing the kinase of interest are exposed to ATP and a synthetic peptide substrate with a Cdk5-specific phosphorylation site and an amino-terminal biotin moiety. Phosphorylated peptide is detected using allophycocyanin-labeled streptavidin, a phosphopeptide specific antibody, and a Europium-chelate-labeled secondary antibody. Simultaneous binding of the streptavidin and the phosphospecific antibody to a phosphorylated substrate molecule brings the Europium chelate "donor" on the secondary antibody close enough to the allophycocyanin fluorophore "acceptor" for fluorescence resonance energy transfer to occur, measurable as a decrease in Europium emission at 615 nm and an increase in allophycocyanin emission at 665 nm wavelength. The Europium—allophycocyanin donor—acceptor pair is commonly used in order to take advantage of the long fluorescence lifetime of excited Europium, thus the signal is "time-resolved".

Other pairs of fluorophores, such as coumarin and fluorescein isothiocyanate, can be used. Pairs of such molecules that can engage in fluorescence resonance energy transfer (FRET) are termed FRET pairs. In order for energy transfer to occur, the donor and acceptor molecules must typically be in close proximity (up to 70 to 100 Å (Clegg, 1992, Methods Enzymol. 211:353–388; Selvin, 1995, *Methods Enzymol.* 246: 300–334). The efficiency of energy transfer falls off rapidly with the distance between the donor and acceptor molecules. Molecules that are commonly used in FRET include fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), and 5-(2'-aminoethyl)aminonaphthalene-1-sulfonic acid (EDANS). Whether a fluorophore is a donor or an acceptor is defined by its excitation and emission spectra, and the fluorophore with which it is paired. For example, FAM is most efficiently excited by light with a wavelength of 488 nm, and emits light with a spectrum of 500 to 650 nm, and an emission maximum of 525 nm. FAM is a suitable donor fluorophore for use with JOE, TAMRA, and ROX (all of which have their excitation maximum at 514 nm).

Fluorescence polarization measurements can also be used for measuring the activity of a protein kinase or a phosphatase (see, e.g., Parker, Law et al., 2000, Development of high throughput screening assays using fluorescence polarization: nuclear receptor-ligand-binding and kinase/phosphatase assays, J. Biomolec. Screening 5(2): 77–88; Turek et al., 2001, Anal. Biochem. 299: 45–53). Binding of a large specific antibody to a fluorescent small phosphopeptide slows its tumbling rate and increases the fluorescence polarization signal. Thus fluorescence polarization is proportional to the amount of bound fluorescent phosphopeptide. This assay can be used in a competitive mode, in which a fixed concentration of fluorescent peptide and antibody are added to a biological sample, and the presence of non-fluorescent phosphoprotein or phosphopeptide is recorded as a decrease in signal. It can also be used in a direct binding mode, in which phosphate addition (by kinase) or removal (by phosphatase) modulates antibody binding and thus polarization signal. In a specific embodiment, a fluorescence polarization assay is performed using the methods of Turek et al. (2001, Anal. Biochem. 299: 45–53), in which a product-specific anti-phosphorylated peptide-specific (e.g., anti-phosphoserine) antibody is used.

In certain embodiments of the invention, homogeneous, fluorescent techniques such as fluorescence polarization (FP) are preferred methods for screening many types of drug targets according to the methods of the invention. Fluorescence polarization (FP) has been used to develop high throughput screening (HTS) assays for nuclear receptor-ligand displacement and kinase inhibition. FP is a solution-based, homogeneous technique requiring no immobilization or separation of reaction components. The FP-based estrogen receptor (ER) assay is based on the competition of fluorescein-labeled estradiol and estrogen-like compounds for binding to ER (Parker, Law, et al., 2000, Development of high throughput screening assays using fluorescence polarization: nuclear receptor-ligand-binding and kinase/phosphatase assays, J. Biomolecular Screening 5(2): 77–88). Studies by Parker et al. determined the Kd for this interaction to be 3 nM for ERα and 2 nM for ERβ; $IC_{50}$ values for 17β-estradiol, tamoxifen, 4-OH-tamoxifen, and diethylstilbestrol were determined to be 5.6, 189, 26, and 3.5 nM, respectively. In a screen of 50 lead compounds from a transcriptional activation screen, 21 compounds had $IC_{50}$ values below 10 μM, with one having an almost 100-fold higher affinity for ERβ over ERα. These data show that an FP-based competitive binding assay can be used to screen diverse compounds with a broad range of binding affinities for ERs.

An FP-based protein-tyrosine kinase (PTK) assay may also be used (Parker, Law, et al., 2000, Development of high throughput screening assays using fluorescence polarization: nuclear receptor-ligand-binding and kinase/phosphatase assays, J. Biomolecular Screening 5(2): 77–88). This PTK assay uses fluorescein-labeled phosphopeptides bound to anti-phosphotyrosine antibodies. Phosphopeptides generated by a kinase of interest compete for this binding.

A protein kinase C (PKC) assay may also be used (Parker, Law, et al., 2000, Development of high throughput screening assays using fluorescence polarization: nuclear receptorligand-binding and kinase/phosphatase assays, J. Biomolec. Screening 5(2): 77–88). Like the FP-based PTK assay, the PKC assay utilizes competition. PKC isoforms have different turnover rates for the peptide substrate. The $IC_{50}$ for staurosporine, for example, is less than 10 nM for all PKC isoforms.

A tyrosine phosphatase assay may also be used (Parker, Law, et al., 2000, Development of high throughput screening assays using fluorescence polarization: nuclear receptor-ligand-binding and kinase/phosphatase assays, J. Biomolec. Screening 5(2): 77–88). Tyrosine phosphatase assays use direct binding rather than competition. Increasing concentrations of T-cell protein-tyrosine phosphatase (TC PTP) increase the rate of dephosphorylation. This change in polarization is dependent on TC PTP and is inhibited by 50 µM $Na_3VO_4$. The $IC_{50}$ of $Na_3VO_4$ is 4 nM for TC PTP. These data demonstrate that a FP-based assay can detect kinase and phosphatase activity. In certain embodiments, such homogeneous, fluorescent techniques such as the FP assays disclosed herein are preferred methods for screening many types of drug targets. New high throughput screening (HTS) instrumentation and assay methods like these make FP a technology that is easily incorporated into high throughput screening by those of ordinary skill in the art.

In certain embodiments, modulators (e.g., inhibitors) of Cdk5 can be identified via enzymatic assays using recombinant Cdk5 purified from bacteria after expression using vectors, using cell lysates containing Cdk5, or using brain tissue lysates (see, e.g., Leost et al., 2000, Eur. J. Biochem. 267: 5983–5994). In other embodiments, modulators of Cdk5 can be identified via enzymatic assays using recombinant Cdk5 purified from insect cells (e.g., Sf9 cells) after expression using baculovirus. In such assays, an enzyme or lysate is incubated at 30° C. with peptide substrate biotin-DARPP-32 (amino acid residues 67–82) (approximately 1 µM), in an appropriate buffer (500 µM ATP, 50 mM HEPES, pH7.5/10 mM $MgCl_2$, 1 mM dithiothreitol), in a final reaction volume of 40–60 µl. The reaction is halted by addition of an equal volume of stop buffer (30 mM EDTA, pH 7.0).

For detection of phosphorylated peptide, aliquots of the stopped reaction (20–30 µl) are added in triplicate to a 384-well black multiwell plate, followed by addition of two volumes of antibody mix containing rabbit polyclonal anti-phosphothr75-DARPP-32 antibody (1 nM), europium-labeled anti-rabbit IgG (1 nM), and streptavidin-allophycocyanin conjugate (2 ug/ml), in an appropriate buffer (0.1% BSA in phosphate-buffered saline, pH 7.4). After incubation at 20° C. for 1–24 hr, fluorescence is measured (excitation filter wavelength 340 nM; emission filter wavelength 660 nM) over a 200-µs period starting 50 µs after the excitation using Applied Biosystems Cytofluor. Other antibody combinations, such as a mouse monoclonal anti-phosphothr75 DARPP-32 and europium-labeled anti-mouse IgG, are contemplated according to the invention, and would be expected to give comparable results.

Inhibitors of CK1 can be identified via a similar enzymatic assay using isolated CK1, cell lysates containing CK1, or brain tissue lysates. In this assay, enzyme or lysate is incubated at 30° C. with peptide substrate biotin-DARPP-32 (amino acid residues 132–146) (approximately 1 µM), in an appropriate buffer (500 µM ATP, 50 mM HEPES, pH7.5/10 mM MgCl2, 1 mM dithiothreitol), in a final reaction volume of 40–60 µl. The reaction is halted by addition of an equal volume of stop buffer (30 mM EDTA, pH 7.0).

For detection of phosphorylated peptide, aliquots of the stopped reaction (20–30 µl) are added in triplicate to a 384-well black multiwell plate, followed by addition of two volumes of antibody mix containing anti-phospho ser137-DARPP-32 antibody (1 nM), europium-labeled anti-mouse IgG (1 nM), and streptavidin-allophycocyanin conjugate (2 ug/ml), in an appropriate buffer (0.1% BSA in phosphate-buffered saline, pH 7.4). After incubation at 20° C. for 1–24 hr, fluorescence is measured (excitation filter wavelength 340 nM; emission filter wavelength 660 nM) over a 200-µs period starting 50 µs after the excitation using Applied Biosystems Cytofluor. Other antibody combinations, such as rabbit polyclonal anti-phosphothr75 DARPP-32 and europium-labeled anti-rabbit IgG, are contemplated according to the invention, and would be expected to give comparable results.

In one form of the above-disclosed assay, recombinant enzyme, enzyme isolated from tissue, or tissue or cell lysate is incubated at 30° C. with biotin-peptide substrate providing a proline-directed phosphorylation site. Amino acid residues 67–82 of human DARPP-32, KRPNPCAYT-PPSLKAV (SEQ ID NO: 5), which are identical to phosphorylation sites in rat and mouse DARPP-32, provide such a substrate.

In another form of the above-disclosed assay, recombinant enzyme, enzyme isolated from tissue, or tissue or cell lysate is incubated at 30° C. with biotin-peptide substrate providing a casein kinase phosphorylation site. Amino acid residues 133–143 of human DARPP-32, EEEDSQAEVLK (SEQ ID NO: 6), which are identical to phosphorylation sites in rat and mouse DARPP-32, provide such a substrate.

Modulation of intracellular kinase activity in response to mGluR ligands can be monitored by a variety of means known to those skilled in the art. Cultured cells displaying mGluR on their cell surfaces can be incubated with agonists or antagonists, the intracellular kinases released by detergent lysis, and their activity measured by fluorescent detection of phosphorylation as disclosed above or by radioisotope tracer methods. Radioisotope tracer methods may be used such as those disclosed in, e.g., Liu, F., X. H. Ma, et al. (2001). "Regulation of cyclin-dependent kinase 5 and casein kinase 1 by metabotropic glutamate receptors." Proc. Natl. Acad. Sci. USA 98(20): 11062–8; Evans, D. B., K. B. Rank, et al. (2002). "A scintillation proximity assay for studying inhibitors of human tau protein kinase II/Cdk5 using a 96-well format." J. Biochem. Biophys. Meth. 50(2–3): 151–61; and McDonald et al., 1999, A scintillation proximity assay for Raf/MEK/ERK kinase cascade: High-throughput screening and identification of selective enzyme inhibitors, Anal. Biochem. 268: 318–329.

In another embodiment, a cell-based assay for phosphorylation is used. In a specific embodiment, signal transduction based on protein phosphorylation is visualized in vivo, e.g., in single living cells using fluorescent indicators, using methods such as those disclosed in Sato et al. (2002, Fluorescent indicators for imaging protein phosphorylation in single living cells, Nature Biotechnology 20(3): 287–94). Such sensors consist of two fluorescent protein molecules, separated by a flexible linker. The linker peptide contains a phosphorylation site and a phosphoprotein recognition element. Phosphorylation of the linker causes a conformational change that brings the two fluorescent proteins into close proximity, allowing FRET to occur and changing the fluorescent output of the system.

In other embodiments, a cell-based assay for phosphorylation is used. In a specific embodiment, genetically encoded sensors of protein phosphorylation are used Such sensors consist of two fluorescent protein molecules, separated by a flexible linker. The linker peptide contains a phosphorylation site and a phosphoprotein recognition element. Phosphorylation of the linker causes a conformational change that brings the two fluorescent proteins into close proximity, allowing FRET to occur and changing the fluorescent output of the system.

5.3. COMPOUNDS THAT MODULATE THE ACTIVITY OF CKI AND/OR CDK5 VIA A METABOTROPIC GLUTAMATE RECEPTOR SIGNALING PATHWAY

The present invention also provides compositions for modulating the activity of casein kinase I (CKI) and/or cyclin-dependent kinase 5 (Cdk5) including, but not limited to the following agents, drugs, compounds or small molecules disclosed hereinbelow. The invention also provides compositions for modulating the activity of calcium channels via modulation of the activity of casein kinase I (CKI) and/or cyclin-dependent kinase 5 (Cdk5), including, but not limited to the following agents, drugs, compounds or small molecules disclosed hereinbelow. The invention also provides compositions for use in methods of treatment of mGluR-related, CKI-related, Cdk5-related and/or calcium channel-related disorders, wherein the compositions modulate the activity of casein kinase I (CKI) and/or cyclin-dependent kinase 5 (Cdk5), including, but not limited to the following agents, drugs, compounds or small molecules disclosed hereinbelow. In certain embodiments, the compositions modulate activity via a mGluR signaling pathway. In one embodiment, the mGluR signaling pathway comprises: activation of mGluR1 receptors that stimulate G proteins that are coupled to PLCβ, activation of the $Ca^{2+}$/calmodulin-dependent phosphatase, calcineurin (PP2B), by $Ca^{2+}$ released from IP3-sensitive stores, dephosphorylation of the inhibitory autophosphorylation sites on CK1ε by calcineurin, resulting in an increase in kinase activity.

Without wishing to be bound by any particular theory, in one aspect of the invention, activation of mGluR1 receptors stimulates G proteins that are coupled to PLCβ, $Ca^{2+}$ released from IP3-sensitive stores activates the $Ca^{2+}$/calmodulin-dependent phosphatase, calcineurin (PP2B), and calcineurin then dephosphorylates the inhibitory autophosphorylation sites on CKI. Dephosphorylation of CKI results in an increase in kinase activity. Therefore, in one embodiment of the invention, the invention provides agents that modulate the activity or expression of CKI through the modulation of activity of calcineurin (PP2B).

Suitable mGluR agonists include, but are not limited to: (±)-1-Aminocyclopentane-trans-1,3-dicarboxylic acid, (±)-1-Amino-[4,5-3H]-cyclopentane-trans-1,3-dicarboxylic acid, (1S,3R)-1-Aminocyclopentane-1,3-dicarboxylic acid, trans-Azetidine-2,4-dicarboxylic acid, (RS)-2-Chloro-5-hydroxyphenylglycine, (RS)-3,5-Dihydroxyphenylglycine, (S)-3,5-Dihydroxyphenylglycine, (2S,1'S,2'S)-2-(2'-Carboxy-3',3'-difluorocyclopropyl)glycine, (S)-1-Aminopropane-1,3-dicarboxylic acid, L-Homocysteinesulphinic acid, (RS)-3-Hydroxyphenylglycine, (S)-3-Hydroxyphenylglycine, L-Quisqualic acid, (L)-(+)-α-Amino-3,5-dioxo-1,2,4-oxadiazolidine-2-propanoic acid, S-Sulpho-L-cysteine sodium salt, (2R,4R)-4-Aminopyrrolidine-2,4-dicarboxylate, (2S,3S,4S)-CCG/(2S,1'S,2'S)-2-(Carboxycyclopropyl)glycine, (2S,2'R,3'R)-2-(2',3'-Dicarboxycyclopropyl)glycine, (2S,2'R,3'R)-2-(1'-$^3$H,2',3'-Dicarboxycyclopropyl)glycine, (2S,1'S,2'S)-2-(2'-Carboxy-3',3'-difluorocyclopropyl)glycine, (S)-2-Amino-2-methyl-4-phosphonobutanoic acid, (2S,3S,4S)-2-Methyl-2-(carboxycyclopropyl)glycine, α-NAAG/N-Acetyl-L-aspartyl-L-glutamic acid, (1S,3R,4S)-1-Aminocyclopentane-1,2,4-tricarboxylic acid, (3RS,4RS)-1-Aminocyclopentane-1,3,4-tricarboxylic acid, L(+)-2-Amino-4-phosphonobutyric acid, L(+)-2-Amino-4-phosphono-[2,3-$^3$H)]-butyric acid, UBP1109/(S)-3,4-Dicarboxyphenylglycine (RS)-4-Chloro-3,5-dihydroxyphenylglycine, 2-Amino-4-(3-hydroxy-5-methylisoxazol-4-yl)butyric acid, O-Phospho-L-serine (R,S)-4-Phosphonophenylglycine, (1R,3R,4S)-1-Aminocyclopentane-1,3,4-tricarboxylic acid, L-Cysteinesulphinic acid, (RS)-3,4-Dicarboxyphenylglycine, α-Amino-(3-hydroxy-5-isoxazolyl) acetic acid, and (RS)-α-Methyl-3-carboxymethyl-phenylglycine.

Suitable mGluR antagonists include, but are not limited to: (RS)-1-Aminoindan-1,5-dicarboxylic acid, DL-2-Amino-3-phosphonopropionic acid, (S)-3-Carboxy-4-hydroxyphenylglycine, (S)-4-Carboxy-4-hydroxyphenylglycine, (S)-4-Carboxyphenyl glycine, 7-(Hydroxyimino) cyclopropa[b]chromen-1a-carboxylate ethyl ester, (RS)-α-Ethyl-4-carboxyphenylglycine, (S)-(+)-α-Amino-4-carboxy-2-methylbenzeneacetic acid, (RS)-α-Methyl-4-carboxyphenylglycine, (S)-α-Methyl-4-carboxyphenylglycine 2-Methyl-6-(phenylethynyl)pyridine, 2-Methyl-6-([3,5-3H]phenylethynyl) pyridine, N-Phenyl-7-(hydroxyimino) cyclopropa[b]chromen-1a-carboxamide, 6-Methyl-2-(phenylazo)-3-pyridinol, 2-Methyl-6-(2-phenylethenyl) pyridine, (RS)-1-Amino-5-phosphonoindan-1-carboxylic acid, (2S)-α-Ethylglutamic acid, (2S)-2-Amino-2-[(1S,2S)-2-carboxycycloprop-1-yl]-3-(xanth-9-yl) propanoic acid, (2S)-2-Amino-2-[(1S,2S)-2-carboxycycloprop-1-yl]-3-[2,7-$^3$H]xanth-9-yl) propanoic acid, α-Methyl-L-CCG I/(2S,3S,4S)-2-Methyl-2-(carboxycyclopropyl) glycine, (RS)-α-Methylserine-O-phosphate monophenyl ester, (RS)-α-Methyl-4-sulphonophenylglycine, (RS)-α-Methyl-4-phosphonophenylglycine, (RS)-α-Methylserine-O-phosphate, (RS)-α-Methyl-4-sulphonophenylglycine, α-Methyl-3-methyl-4-phosphonophenyglycine, L-AP3 and BAY36-7620 (De Vry et al., 2001, Eur. J. Pharmacol. 428: 203–214). In a specific embodiment, the mGluR antagonist is a group I mGluR antagonist, e.g., L-AP3.

Other therapeutic agents include but are not limited to: donepzil hydrochloride, rivastigmine, galantamine Pramipexole, ropinirole, trihexylphenidyl, selegine, benzotropine, pergolide, entacapone, selegiline, levodopa, pramipexole, bromocriptine, m selegiline, carbidopa, amantidine, tolcapone, Dextroamphetamine, methylphenidate, pemoline, risperidone, olanzapine, clozapinehal, operidol, chlorpromazine, quetiapine, fluphenazine, and perphenazine.

Other therapeutic agents include, but are not limited to CKI inhibitors, e.g., CKI-7 (CK1–7) and Cdk5 inhibitors, e.g., butyrolactone.

Other therapeutic agents include, but are not limited to: PLCβ inhibitors (e.g., U73122), $Ca^{2+}$ chelators (e.g., BAPTA/AM).

Other therapeutic agents include, but are not limited to, calcineurin inhibitors, e.g., cyclosporin A, Cypermethrin 3-(2,2-Dichloroethenyl)-2,2-dimethylcyclopropane carboxylic acid cyano (3-phenoxyphenyl)methyl ester, Tacrolimus (FK506, Prograf), Deltamethrin and ISATX247 (Isotechnika).

Other therapeutic agents include, but are not limited to antiepileptic drugs, e.g., phenyloin (Dilantin), which is usually the drug of choice for the treatment of epilepsy, phenobarbital, primidone (Mysoline), carbamazepine (Tegretol) for complex partial tonic-clonic seizures, and ethosuximide (Zarontin) and clonazepam (Klonopin) for absence seizures. Valproic acid (Depakene) is also used in the treatment of absence seizures. The choice of drug and calculation of optimal dosage is very difficult and highly individualized.

Other therapeutic agents include, but are not limited to: bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, and perhexiline.

It will be apparent to one of skill in the art that certain mGluR agonists or antagonists may have both agonist and antagonist properties. The compounds listed hereinabove are not limited by theory of mechanism but are applicable to the present invention independently of their classification.

The present invention also encompasses methods for designing new chemical compounds that have activity as modulators of mGluR intracellular signaling pathways or of calcium channel activation, wherein these new chemical compounds may include, but not be limited to, any compound with the ability to either stimulate or inhibit mGluR intracellular signaling and/or calcium channel activation, and would include, but not be limited to, low molecular weight organic molecules capable of being delivered intracellularly.

The present invention further provides a method of performing rational drug design to develop drugs that can modulate activity of CKI and/or Cdk5 and thereby ameliorate mGluR signaling pathway-related disorders. Such rational drug design can be performed using compounds that have been identified as agonists or antagonists of mGluR as a starting point. In another embodiment, compounds that have been identified as agonists or antagonists of CKI or Cdk5 can be used as a starting point. Thus, the present invention provides screens and assays to allow more specific inhibitors to be identified. Such methods of rational drug design are well-known in the art. In a specific embodiment, the rational drug design methods disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties, are used.

Indeed, potential modulators can be examined through the use of computer modeling using a docking program such as GRAM, DOCK, or AUTODOCK (Dunbrack et al., Folding & Design 2:27–42 (1997)), to identify potential modulators of, e.g., a mGluR signaling pathway. These modulators can then be tested for their effect on CKI or Cdk5 activity. This procedure can include computer fitting of potential modulators to the mGluR or CKI complex to ascertain how well the shape and the chemical structure of the potential modulator will bind to either mGluR or CKI (Bugg et al., 1993, Scientific American (Dec.) 269(6):92–98; West et al., TIPS, 16:67–74 (1995)). Computer programs can also be employed to estimate the attraction, repulsion, and steric hindrance of the subunits with a modulator/inhibitor.

Generally the tighter the fit, the lower the steric hindrances, and the greater the attractive forces, the more potent the potential modulator since these properties are consistent with a tighter binding constant. Furthermore, the more specificity in the design of a potential drug the more likely that the drug will not interact as well with other proteins. This will minimize potential side-effects due to unwanted interactions with other proteins.

Initially, compounds known to bind mGluR (e.g., (S)-3,5-Dihydroxyphenylglycine (DHPG)), can be systematically modified by computer modeling programs until one or more promising potential analogs are identified. In addition systematic modification of selected analogs can then be systematically modified by computer modeling programs until one or more potential analogs are identified. Such analyses are well known to those of skill in the art and have been shown to be effective in the development of, e.g., HIV protease inhibitors (see, e.g., Lam et al., Science 263: 380–384 (1994); Wlodawer et al., Ann. Rev. Biochem. 62:543–585 (1993); Appelt, Perspectives in Drug Discovery and Design 1:23–48 (1993); Erickson, Perspectives in Drug Discovery and Design 1:109–128 (1993)). Alternatively a potential modulator can be obtained by initially screening a random peptide library produced by recombinant bacteriophage, e.g., as disclosed hereinabove. A peptide selected in this manner is then systematically modified by computer modeling programs as disclosed above, and then treated analogously to a structural analog as disclosed above.

Once a potential modulator is identified, it can be either selected from a library of chemicals, as are commercially available (e.g., from Chembridge Corporation, San Diego, Calif. or Evotec OAI, Abingdon, UK). Alternatively, the potential modulator may be synthesized de novo. Potential peptide modulators may be synthesized by protein synthetic techniques, e.g., by use of a peptide synthesizer or other methods of protein/peptide synthesis well known in the art. In one embodiment, the methods of protein/peptide synthesis disclosed in U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, (incorporated herein by reference in their entireties) are used. The de novo synthesis of one or even a relatively small group of specific compounds is reasonable in the art of drug design.

Any of the potential agents, targets for the potential agents (e.g., mGluR, CKI, Cdk5) or DARPP-32 (such as $^{32}$P-Thr75 phosphorylated DARPP-32) can be labeled. Suitable labels include enzymes (e.g., alkaline phosphatase or horseradish peroxidase), fluorophores (e.g., fluorescein isothiocyanate (FITC), phycoerythrin (PE), Texas red (TR), rhodamine, free or chelated lanthanide series salts, especially $Eu^{3+}$, to name a few fluorophores), chromophores, radioisotopes, chelating agents, dyes, colloidal gold, latex particles, ligands (e.g., biotin), chemiluminescent agents, magnetic beads or magnetic resonance imaging labels. When a control marker is employed, the same or different labels may be used for the receptor and control marker.

In embodiments wherein a radioactive label, such as the isotopes $^{3}$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re is used, standard counting procedures known in the art may be utilized.

In embodiments wherein the label is an enzyme, detection may be accomplished by any of the presently utilized colorimetric, spectrophotometric, fluorospectrophotometric, amperometric or gasometric techniques known in the art.

A direct label is an example of a label that can be used according to the methods of the present invention. A direct label is an entity that, in its natural state, is readily visible, either to the naked eye (for example, by visual inspection through a compound or dissecting light microscope), or with the aid of an optical filter and/or applied stimulation, e.g., U.V. light to promote fluorescence. Examples of colored labels that can be used according to the methods of the present invention, include metallic sol particles, for example, gold sol particles such as those disclosed by Leuvering (U.S. Pat. No. 4,313,734); dye sol particles such as disclosed by Gribnau et al. (U.S. Pat. No. 4,373,932) and May et al. (WO 88/08534); dyed latex such as disclosed by May et al. (WO 88/08534), Snyder (EP-A 0280 559 and 0 281 327); or dyes encapsulated in liposomes as disclosed by Campbell et al. (U.S. Pat. No. 4,703,017).

Other direct labels include a radionucleotide, a luminescent moiety, or a fluorescent moiety including, but not limited, to, e.g., a modified/fusion chimera of green fluorescent protein (as disclosed in U.S. Pat. No. 5,625,048, issued Apr. 29, 1997, and WO 97/26333, published Jul. 24, 1997, each of which is incorporated herein by reference in its entirety).

In addition to these direct labeling devices, indirect labels comprising enzymes can also be used according to the present invention. Various types of enzyme-linked immunoassays are well known in the art, for example, enzyme-linked immunoassays using alkaline phosphatase, horseradish peroxidase, lysozyme, glucose-6-phosphate dehydrogenase, lactate dehydrogenase, or urease. These and other similar assays are well known in the art and are disclosed, e.g., in Engvall (1980, "Enzyme Immunoassay ELISA and EMIT," in *Methods in Enzymotogy*, 70: 419–439) and in U.S. Pat. No. 4,857,453.

In certain embodiments, proteins can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions) (see, e.g., U.S. patent application Ser. Nos. 09/419,379, by Bibb et al., entitled "Methods of Identifying Agents That Regulate Phosphorylation/Dephosphorylation in Dopamine Signaling," filed Oct. 15, 1999, and Ser. No. 09/687,959, by Bibb et al., entitled "Methods of Identifying Agents That Regulate Phosphorylation/Dephosphorylation in Dopamine Signaling," filed Oct. 13, 2000, incorporated herein by reference in their entireties).

5.4. DIAGNOSTIC AND THERAPEUTIC METHODS

As disclosed herein, the invention provides agents, drugs, compounds and compositions that modulate the activity or expression of CKI and/or Cdk5.

The present invention also provides diagnostic and therapeutic methods for the treatment of a mGluR-related, CKI-related, Cdk5-related or calcium channel-related disorder, including, but not limited the use of such compositions or compounds in the treatment of a mGluR-related, CKI-related, Cdk5-related or calcium channel-related disorder.

In one aspect, the invention provides a method for treating a neuronal condition characterized by an increase or a decrease in calcium channel activity (e.g., calcium channel currents) comprising administering an effective amount of a compound according to the present invention to modulate CKI and/or Cdk5 activity, and thus increase or decrease calcium channel activity via modulation of a mGluR signaling pathway. In one embodiment, the compound is identified by the methods of the invention disclosed herein.

In addition, the present invention provides methods for treating a mGluR-related, CKI-related, Cdk5-related or calcium channel-related disorder in an individual (e.g., a patient) or in an animal subject, by administering an effective amount of a compound of the invention to modulate CKI and/or Cdk5 activity. In one embodiment, the agent promotes or increases the activity of CKI and/or Cdk5. In another embodiment, the agent inhibits or decreases the activity of CKI and/or Cdk5.

In a particular embodiment, a method of the invention is used to treat a mGluR-related, CKI-related, Cdk5-related or calcium channel-related disorder in an individual that is related to a symptom and/or disease state characteristic of Alzheimer's disease.

In another embodiment, a method of the invention is used to treat a mGluR-related, CKI-related, Cdk5-related or calcium channel-related disorder in an individual that is related to a symptom and/or disease state characteristic of Huntington's Disease.

In another embodiment, a method of the invention is used to treat a mGluR-related, CKI-related, Cdk5-related or calcium channel-related disorder in an individual that is related to a symptom and/or disease state characteristic of Parkinson's disease.

In another embodiment, a method of the invention is used to treat a mGluR-related, CKI-related, Cdk5-related or calcium channel-related disorder in an individual that is related to a symptom and/or disease state characteristic of Tourette's syndrome.

In another embodiment, a method of the invention is used to treat a mGluR-related, CKI-related, Cdk5-related or calcium channel-related disorder in an individual that is related to a symptom and/or condition characteristic of stroke.

In another embodiment, a method of the invention is used to treat a mGluR-related, CKI-related, Cdk5-related or calcium channel-related disorder in an individual that is related to a symptom and/or condition characteristic of epilepsy.

In another embodiment, a method of the invention is used to treat a mGluR-related, CKI-related, Cdk5-related or calcium channel-related disorder in an individual that is related to a symptom and/or disease state characteristic of schizophrenia.

In another embodiment, a method of the invention is used to treat a mGluR-related, CKI-related, Cdk5-related or calcium channel-related disorder in an individual that is related to a symptom and/or disease state characteristic of insomnia.

In another embodiment, a method of the invention is used to treat a mGluR-related, CKI-related, Cdk5-related or calcium channel-related disorder in an individual that is related to a symptom and/or disease state characteristic of depression.

In another embodiment, a method of the invention is used to treat a mGluR-related, CKI-related, Cdk5-related or calcium channel-related disorder in an individual that is related to a symptom and/or condition characteristic of attention deficit disorder (ADD).

In another embodiment, a method of the invention is used to treat a mGluR-related, CKI-related, Cdk5-related or calcium channel-related disorder in an individual that is related to a symptom and/or condition characteristic of attention deficit hyperactivity disorder (ADHD).

In another embodiment, a method of the invention is used to treat a mGluR-related, CKI-related, Cdk5-related or calcium channel-related disorder in an individual that is related to a symptom and/or condition characteristic of drug abuse.

In another embodiment, a method of the invention is used to treat a mGluR-related, CKI-related, Cdk5-related or calcium channel-related disorder in an individual that is related to a symptom and/or condition characteristic of pain.

In another embodiment, a method of the invention is used to treat a mGluR-related, CKI-related, Cdk5-related or calcium channel-related disorder in an individual that is related to a symptom and/or disease state characteristic of cancer.

Preferably the agent, compound or composition administered in the method of treatment can cross through the blood brain barrier in sufficient quantities and at a sufficient rate so as to allow the treatment of the disorder and thereby, the condition or disease. In one such embodiment, the agent is administered intravenously. In another embodiment, the agent is administered orally. More preferably the agent can cross the blood brain carrier without a carrier (for methods and routes of administration, see Section 5.6).

5.5. MODELS FOR DISEASES OR DISORDERS

According to the methods of the invention, an animal model for a disease or disorder related to a metabotropic glutamate receptor signaling pathway, including but not limited to Alzheimer's disease, Huntington's Disease, Parkinson's disease, Tourette's syndrome, stroke, epilepsy, sleep or circadian rhythm disorder (e.g., insomnia), schizophrenia, depression, attention deficit disorder (ADD), attention deficit hyperactivity disorder (ADHD), drug abuse, pain, and cancer, may be used in assays to screen for compounds that modulate the activity of CKI or Cdk5, or for compounds that ameliorate the symptoms of a mGluR-related, CKI-related, Cdk5-related or calcium channel-related disorder. In one embodiment, the mGluR signaling pathway comprises: activation of mGluR1 receptors that stimulate G proteins that are coupled to PLCβ, activation of the $Ca^{2+}$/calmodulin-dependent phosphatase, calcineurin (PP2B), by $Ca^{2+}$ released from IP3-sensitive stores, dephosphorylation of the inhibitory autophosphorylation sites on CK1ε by calcineurin, resulting in an increase in kinase activity.

In one embodiment, an animal model for a mGluR-related, CKI-related, Cdk5-related or calcium channel-related disorder is used in screening assays according to the methods of the invention. Such animals can be mice, rats, hamsters, sheep, pigs, cattle, etc., and are preferably non-human mammals.

In one embodiment, a transgenic mouse is used as an animal model for Alzheimer's disease (see, e.g., Lewis et al. (2000; Aug.), Neurofibrillary tangles, amyotrophy and progressive motor disturbance in mice expressing mutant (P301L) tau protein, Nature Genetics 25(4): 402–5, erratum in 2000, Nat. Genet. 26(1):127; Lewis et al. 2001, Enhanced neurofibrillary degeneration in transgenic mice expressing mutant tau and APP, Science 293(5534):1487–91; Gotz et al., 2001, Formation of neurofibrillary tangles in P3011 tau transgenic mice induced by Abeta 42 fibrils, Science 293 (5534): 1491–5). Lewis et al. (2000, Neurofibrillary tangles, amyotrophy and progressive motor disturbance in mice expressing mutant (P301L) tau protein, Nature Genetics 25(4): 402–5, erratum in 2000, Nat. Genet. 26(1):127) discloses a transgenic mouse expressing human P301L Tau protein. Animals from this strain of mice develop age-dependent Alzheimer's-like neurofibrillary tangles containing hyperphosphorylated tau and progressive motor disturbance. The effect of modulators of mGluR signaling, CK1 activation, or subsequent Cdk5 activation, on the development of neurofibrillary tangles and neuronal dysfunction are studied in this model system. The effect of mGluR signaling pathway modulators on Abeta 42 stimulated formation of neurofibrillary tangles may also be studied in this animal model. In this case, Abeta 42 may be supplied by genetic cross of P3011 Tau-expressing mice with human APP-expressing mice (e.g., Lewis et al. 2001, Enhanced neurofibrillary degeneration in transgenic mice expressing mutant tau and APP, Science 293(5534):1487–91) or by direct injection of Abeta 42 into the brain of P3011 Tau-expressing mice (e.g., Gotz et al., 2001, Formation of neurofibrillary tangles in P3011 tau transgenic mice induced by Abeta 42 fibrils, Science 293(5534):1491–5). Such model animal systems may be used to screen for compounds useful in the treatment of Alzheimer's disease due to their effect on mGluR intracellular signaling pathways.

In another embodiment, a rat model of stroke is used. Brint et al. (1988, J. Cerebr. Blood Flow & Metab. 8:474–485) discloses a rat model of focal brain ischemia. De Vry et al. (2001, Eur. J. Pharmacol. 428: 203–214) discloses a rat acute subdural hematoma model and a rat middle cerebral artery occlusion model that was used to investigate the neuroprotective and behavioral effects of a mGluR antagonist, BAY 36–7620. Bao et al. (2001, Brain Res. 922:173–179) discloses a rat model of focal cerebral ischemia in which group I mGluR receptor agonists and antagonists were tested. Tanaka et al. (2002, Brain Research 924:98–108) disclose a method of measurement of stroke by middle cerebral artery occlusion. Such a model animal system may be used to screen for compounds useful in the treatment of stroke due to their effect on mGluR intracellular signaling pathways.

In another embodiment, a mouse model of schizophrenia is used (Sipes et al., 1995, 8-OH-DPAT disruption of prepulse inhibition in rats: reversal with (+) WAY 100,135 and localization of site of action, Psychopharmacology (Berl) 117(1):41–8; Cao et al., 2002, Brain Research 937: 32–40). Such a model animal system may be used to screen for compounds useful in the treatment of schizophrenia due to their effect on mGluR intracellular signaling pathways.

In other embodiments, a rat model for attention-deficit disorder (ADD) or attention-deficit hyperactivity disorder (ADHD) is used (see, e.g., Hansen et al., 1999, Alcohol responsiveness, hyperreactivity and motor restlessness in an animal model for attention-deficit hyperactivity disorder, Psychopharmacology 146: 1–9; Russell, 2002, Behavioral Brain Res. 130: 191–196). Russell, for example, discloses a spontaneously hypertensive rat model that is a genetic model for ADHD. Such a model animal system may be used to screen for compounds useful in the treatment of ADHD due to their effect on mGluR intracellular signaling pathways.

In another embodiment, a mouse model of pain is used (e.g., O'Callaghan et al., 1975, Quantification of the analgesic activity of narcotic antagonists by a modified hot-plate procedure, J. Pharmacol Exp Ther 192: 497–505; Guarna et al., 2002, J. Neurochem. 80:271–277; Menéndez et al., 2002, Unilateral hot plate test: a simple and sensitive method for detecting central and peripheral hyperalgesia in mice, J. Neurosci. Methods 113:91–97). Guarna et al. discloses a mouse model for acute thermonociception. Menéndez et al. discloses a mouse model for central and peripheral hyperalgesia. Such a model animal system may be used to screen for compounds useful in the treatment of pain due to their effect on mGluR intracellular signaling pathways.

In another embodiment, a rat model of addiction (e.g., cocaine addiction) is used (Caine and Koob, 1995, Pretreatment with the dopamine agonist 7-OH-DPAT shifts the cocaine self-administration dose-effect function to the left under different schedules in the rat, Behav. Pharmacol 6: 333–347; Orsini et al., 2002, Brain Research 925:133–140). Such a model animal system may be used to screen for compounds useful in the treatment of drug abuse or addiction due to their effect on mGluR intracellular signaling pathways.

In another embodiment, a mouse model of Parkinson's disease is used (Uhl et al., 1985, Lancet 1:956–57; Mokry, 1995,Experimental models and behavioral tests used in the study of Parkinson's Disease, Physiol. Res. 44: 143–50.; Du, 2001, Proc. Natl. Acad. Sci. USA 98: 14669–14674). Such a model animal system may be used to screen for compounds useful in the treatment of Parkinson's disease due to their effect on mGluR intracellular signaling pathways.

In another embodiment, an animal or tissue model of epilepsy is used (see, e.g., Paschoa et al., 1997, Seizure patterns in kindling and cortical stimulation models of experimental epilepsy, Brain Res. 770: 221–227; Kokaia, 1995, Exper. Neurol. 133:215–224; Merlin, 1999, J. Neurophysiol. 82: 1078–1081; Merlin, 2001, J. Neurophysiol. 87:621–625). Kokaia (1995, Exper. Neurol. 133:215–224) discloses a mouse model of epilepsy. Merlin (1999, J. Neurophysiol. 82: 1078–1081; 2001, J. Neurophysiol. 87:621–625) discloses a guinea pig hippocampal slice model of epilepsy. Such model animal or tissue systems may be used to screen for compounds useful in the treatment of epilepsy due to their effect on mGluR intracellular signaling pathways.

In another embodiment, cultured HEK 293 cells expressing rat group I mGluRs are used as a model to screen for compounds that activate calcium channels via the mGluR signaling pathway (McCool et al., 1998, Rat group I metabotropic glutamate receptors inhibit neuronal Ca2+ channels via multiple signal transduction pathways in HEK 293 cells, J. Neurophysiol. 79(1):379–91).

In another embodiment, a rodent (e.g., mouse) model of cancer, tumor formation, or carcinogenesis is used. Such rodent models are well known to those of skill in the art (see, e.g., Sato et al., 1997, A metastatic and androgen-sensitive human prostate cancer model using intraprostatic inoculation of LNCaP cells in SCID mice, Cancer Res. 15:1584–1589). For example, in certain embodiments, tumors may be grown subcutaneously in athymic nude mice (see, e.g., Singh et al., 2002, Cancer Res. 62:3063–3069). Such model animal systems may be used to screen for compounds useful in the treatment of cancer or tumors due to their effect on mGluR intracellular signaling pathways.

In a specific embodiment, the animal model is a homozygous DARPP-32 knockout mouse (see U.S. Pat. No. 5,777,195, by Fienberg et al., issued Jul. 7, 1998; U.S. Pat. No. 6,013,621, by Nishi et al., issued Jan. 11, 2000; and Fienberg et al., 1998, Science 281:838–842; each of which is incorporated herein by reference in its entirety). In one embodiment, the homozygous DARPP-32 knockout mouse may be used, in an additional test or assay to validate or confirm that a candidate agent modulates CKI and/or Cdk5 activity. In a specific embodiment, the validation may be carried out according to the methods described in Nishi et al. (U.S. Pat. No. 6,013,621, issued Jan. 11, 2000). When such an agent is identified that modulates the activity of CKI and/or Cdk5 via DARPP-32 phosphorylation, the presence of or administration of the agent in the DARPP-32 knockout mouse should not significantly increase or decrease the amount (and/or rate) of activation of calcium channels relative to the absence or non-administration of the agent.

5.6. Pharmaceutical Compositions

The invention encompasses pharmaceutical compositions for regulating CKI and/or Cdk5 activity, and for diagnosing or treating a mGluR-related, CKI-related, Cdk5-related or calcium channel-related disorder. Because a loss of normal function results in the development of a phenotype of the above-listed diseases or disorders, activation of the metabotropic glutamate receptor (mGluR) signaling pathway, or an increase in CKI and/or Cdk5 activity (e.g., downstream activation) facilitates amelioration of a symptom in individuals exhibiting a symptom of such a disorder.

Alternatively, symptoms of certain mGluR-related, CKI-related, Cdk5-related or calcium channel-related disorders may be ameliorated by decreasing the level of CKI and/or Cdk5 activity, and/or downregulating activity of a metabotropic glutamate receptor signaling pathway (e.g., by targeting downstream signalling events). Different approaches are discussed below.

In certain embodiments, the invention provides methods of administering an agent that can ameliorate a symptom of a mGluR signaling pathway-related disease and/or condition in a patient or subject exhibiting the symptom (see Sections 5.2 and 5.3). In one embodiment, the mGluR signaling pathway comprises: activation of mGluR1 receptors that stimulate G proteins that are coupled to PLCβ, activation of the $Ca^{2+}$/calmodulin-dependent phosphatase, calcineurin (PP2B), by $Ca^{2+}$ released from IP3-sensitive stores, dephosphorylation of the inhibitory autophosphorylation sites on CK1ε by calcineurin, resulting in an increase in kinase activity (see Section 7).

In certain embodiments, the invention provides methods of administrating an agent that can ameliorate a symptom of a mGluR-related, CKI-related, Cdk5-related or calcium channel-related disorder in a patient or subject exhibiting the symptom (see Sections 5.2 and 5.3).

In certain embodiments, an agonist of mGluR activity, as disclosed herein, can be used to for treating a mGluR-related, CKI-related, Cdk5-related and/or calcium channel-related disorder. In other embodiments, an antagonist of mGluR activity, as disclosed herein can be used to for treating a mGluR-related, CKI-related, Cdk5-related and/or calcium channel-related disorder. It is not necessary that the compound demonstrate absolute specificity for the mGluR. For example, compounds that agonize both mGluR and another receptor may be used; such compounds may be administered so that delivery to the nervous system is optimized to achieve amelioration of a mGluR-related, CKI-related, Cdk5-related and/or calcium channel-related disorder.

5.6.1. PHARMACEUTICAL FORMULATIONS

The present invention provides pharmaceutical compositions of the agents, drugs or compounds of the invention disclosed hereinabove. The agent, drug or compound, or their physiologically acceptable salts or solvates, may be formulated for administration for injection, or for oral, topical, nasal, inhalation, insufflation (either through the mouth or the nose) buccal, parenteral, rectal administration or other forms of administration. The invention provides pharmaceutical compositions comprising effective amounts of an agent(s) of the invention together with pharmaceutically acceptable diluents, preservatives, solubilizers, emulsifiers, adjuvants, excipients and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimerosal, benzyl alcohol) and bulking substances (e.g., lactose, mannitol).

The compositions may also be incorporated into particulate preparations of polymeric compounds such as polylactic acid, polyglycolic acid, etc. or liposomes. Hyaluronic acid may also be used. Biocompatible absorbable polymers may be selected from the group consisting of aliphatic polyesters, copolymers and blends, which include, but are not limited to, homopolymers and copolymers of lactide (which include D-, L-, lactic acid and D-, L- and meso lactide), glycolide (including glycolic acid), epsilon-caprolactone, p-dioxanone (1,4-dioxan-2-one, which is disclosed in U.S. Pat. No. 4,052,988), alkyl substituted deriatives of p-dioxanone (i.e., 6,6-dimethyl-1,4-dioxan-2-one which is disclosed in U.S. Pat. No. 5,703,200), triethylene carbonate (1,3-dioxan-2-one), alkyl substituted derivatives of 1,3-dioxanone (which are disclosed in U.S. Pat. No. 5,412,068), delta-valerolactone, beta-butyrolactone, gamma-butyrolactone, epsilon-decala tone, hydroxybutyrate, hydroxyvalerate, 1,4-dioxepan-2-one (disclosed in U.S. Pat. No. 4,052,988 and its dimer 1,5,8,12-tetraoxacyclotetradecane-7,14 dione), 1,5-dioxepan-2-one, and polymer blends thereof.

Such compositions may influence physical state, stability, rate of in vivo release, and rate of in vivo clearance of the present proteins and derivatives. See, e.g., Remington's Pharmaceutical Sciences, 18th ed., (1990, Mack Publishing Co., Easton, Pa. 18042) pages 1435–1712). The compositions may be prepared in liquid form, or be in dried powder, such as lyophilized form.

Contemplated for use herein are oral solid dosage forms, which are disclosed generally in Remington's Pharmaceutical Sciences, 18th Ed. 1990 (Mack Publishing Co. Easton Pa. 18042) at Chapter 89. Solid dosage forms include tablets, capsules, pills, troches or lozenges, cachets or pellets. Also, liposomal or proteinoid encapsulation may be used to formulate the present compositions (as, for example, proteinoid microspheres reported U.S. Pat. No. 4,925,673). Liposomal encapsulation may be used and the lipomes may be derivatized with various polymers (e.g., U.S. Pat. No. 5,013,556). A description of possible solid dosage forms for the therapeutic is given by Marshall, K. In: *Modern Pharmaceutics* Edited by G. S. Banker and C. T. Rhodes Chapter 10, 1979). In general, the formulation will include the agent and inert ingredients (which allow for protection against the stomach environment and release of the biologically active material in the intestine).

To ensure full gastric resistance a coating impermeable to at least pH 5.0 is useful. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings that make the tablet easier to swallow. Capsules may consist of a hard shell (such as gelatin) for delivery of dry therapeutic, i.e., powder; for liquid forms, a soft gelatin shell may be used. The shell material of cachets may be thick starch or other edible paper. For pills, lozenges, molded tablets or tablet triturates, moist massing techniques can be used.

The therapeutic can be included in the formulation as fine multi-particulates in the form of granules or pellets. The formulation of the material for capsule administration can also be as a powder, lightly compressed plugs or even as tablets. The therapeutic can also be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the therapeutic with an inert material or filler. These diluents or fillers can include carbohydrates, especially mannitol, a-lactose, anhydrous lactose, cellulose (e.g., microcrystalline cellulose), sucrose, calcium hydrogen phosphatemodified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include, but are not limited to, starch (e.g., potato starch or the commercial disintegrant based on starch, Explotab). Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch (e.g., pregelatinised maize starch) and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) can both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes, talc and silica. Soluble lubricants may also be used such as sodium lauryl sulfate, magnesium lauryl sulfate, polyethylene glycol of various molecular weights, Carbowax 4000 and 6000.

Glidants that can improve the flow properties of the drug during formulation and to aid rearrangement during compression can be added. The glidants can include starch, talc, pyrogenic silica and hydrated silicoaluminate.

To aid dissolution of the therapeutic into the aqueous environment a surfactant can be added as a wetting agent. Surfactants may include anionic detergents such as sodium lauryl sulfate, dioctyl sodium sulfosuccinate and dioctyl sodium sulfonate. Cationic detergents can be used and can include benzalkonium chloride or benzethomium chloride. The list of potential non-ionic detergents that can be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants can be present in the formulation of the protein or derivative either alone or as a mixture in different ratios.

Additives that potentially enhance uptake of the agent are, for example, the fatty acids oleic acid, linoleic acid and linolenic acid.

Controlled release oral formulation may be desirable. The agent can be incorporated into an inert matrix that permits release by either diffusion or leaching mechanisms, e.g., gums. Slowly degenerating matrices may also be incorporated into the formulation. Some enteric coatings also have a delayed release effect.

Another form of a controlled release of this therapeutic is by a method based on the Oros therapeutic system (Alza Corp.), i.e. the drug is enclosed in a semipermeable membrane, which allows water to enter and to push the drug out through a single small opening due to osmotic effects.

Other coatings may be used for the formulation. These include a variety of sugars that can be applied in a coating pan. The therapeutic agent can also be given in a film coated tablet and the materials used in this instance are divided into two groups. The first are the nonenteric materials and include methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials can be used to provide the optimum film coating. Film coating may be carried out in a pan-coater or in a fluidized bed or by compression coating.

Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Nasal delivery of the agent is also contemplated. Nasal delivery allows the passage of the protein to the blood stream directly after administering the therapeutic product to the nose, without the necessity for deposition of the product in the lung. Formulations for nasal delivery include those with dextran or cyclodextran.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations disclosed previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

5.6.2. DOSAGE DETERMINATIONS

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.6.3. ROUTES OF ADMINISTRATION

The component or components of a therapeutic composition of the invention may be introduced parenterally, topically, or transmucosally, e.g., orally, nasally, or rectally, or transdermally. Preferably, administration is parenteral, e.g., via intravenous injection, and also including, but not limited to, intra-arteriole, intramuscular, intradermal, subcutaneous, intraperitoneal, intraventricular, and intracranial administration. In preferred embodiments, the component or components of a therapeutic composition of the invention is introduced orally or parentally.

In preferred embodiments of the invention, an agent (or drug or compound) can cross and more preferably readily pass through the blood-brain barrier, which permits, e.g., oral, parenteral or intravenous administration. Alternatively, the agent can be modified or otherwise altered so that it can cross or be transported across the blood brain barrier. Many strategies known in the art are available for molecules crossing the blood-brain barrier, including but not limited to, increasing the hydrophobic nature of a molecule; introducing the molecule as a conjugate to a carrier, such as transferring, targeted to a receptor in the blood-brain barrier, or to docosahexaenoic acid etc.

In another embodiment, an agent of the present invention is administered via the standard procedure of drilling a small hole in the skull to administer the agent.

In another embodiment, the molecule can be administered intracranially or, more preferably, intraventricularly. In another embodiment, osmotic disruption of the blood-brain barrier can be used to effect delivery of agent to the brain (Nilayer et al., Proc. Natl. Acad. Sci. USA 92:9829–9833 (1995)). In yet another embodiment, an agent can be administered in a liposome targeted to the blood-brain barrier. Administration of pharmaceutical agents in liposomes is known (see Langer, Science 249:1527–1533 (1990); Treat et al., in *Liposomes in the Therapy of infectious Disease and Cancer*, Lopez-Berestein and Fidler (eds.), Liss, New York, pp. pp. 317–327 and 353–365 (1989). All of such methods are envisioned in the present invention.

Although some predictions have been made concerning the ability of molecules to pass through the blood-brain barrier, these predictions are at best speculative. The rate and extent of entry of a compound into the brain are generally considered to be determined primarily by partition coefficient, ionization constant(s), and molecular size. No single partition solvent system has emerged as a universally applicable model for brain penetration, although the octanol water system has received particular attention, and Hansch and coworkers have suggested that a partition coefficient in this system of about 100 is optimal for entry into the central nervous system (CNS) (Glave and Hansch, J. Pharm. Sci. 61:589 (1972); Hansch et al., J. Pharm. Sci. 76:663 (1987)). In practice, the octanol-water partition system only provides a qualitative indication of the capability of a compound to cross the blood-brain barrier. For example, comparisons between known histamine $H_2$ receptor antagonists suggest that there is no such simple relationship between their brain penetration and octanol water partition coefficients (Young et al., J. Med. Chem. 31:656 (1988)). Other factors, besides the octanol-water partition influence the propensity to cross the blood-brain barrier. Comparison of the ability of histamine $H_2$ receptor antagonists to cross the blood-brain barrier suggests that brain penetration may increase with decreasing over-all hydrogen binding ability of a compound (Young et al., J. Med. Chem. 31:656 (1988)). Begley et al. (J. Neurochem. 55:1221–1230 (1990)) herein incorporated by reference in its entirety, discloses the ability of cyclosporin A to cross the blood-brain barrier. Methodology as used by Begley et al. includes: (1) measuring the brain uptake index (BUI) with the equation for a tritiated agent compound:

BUI=[(brain $^3$H/brain $^{14}$C)/(injectate $^3$H/injectate $^{14}$C)]× 100 where the $^{14}$C reference compound is $^{14}$C butanol or an analogous solvent; (2) Brain perfusion studies; (3) Intravenous bolus injection studies; and (4) Studies with cultured cerebral capillary endothelium.

In another embodiment, the therapeutic compound can be delivered in a vesicle, in particular a liposome (see Langer, Science 249:1527–1533 (1990); Treat et al., in *Liposomes in the Therapy of Infectious Disease and Cancer*, Lopez-Berestein and Fidler (eds.), Liss: New York, pp. 317–327 and 353–365 (1989)). To reduce its systemic side effects, this may be a preferred method for introducing the agent.

In another embodiment, the therapeutic compound can be delivered in a controlled release system. For example, the agent may be administered using intravenous infusion, an implantable osmotic pump, a transdermal patch, liposomes, or other modes of administration. In one embodiment, a pump may be used (see Langer, supra, Sefton, *CRC Crit. Ref Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see *Medical Applications of Controlled Release*, Langer and Wise (eds.), CRC Press: Boca Raton, Fla. (1974); *Controlled Drug Bioavailability, Drug Product Design and Performance*, Smolen and Ball (eds.), Wiley: New York (1984); Ranger and Peppas, *J. Macromol. Sci. Rev. Macromol. Chem.* 23:61 (1983); see also Levy et al., Science 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in *Medical Applications of Controlled Release*, supra, vol. 2, pp. 115–138 (1984)). Other controlled release systems are discussed in the review by Langer (Science 249:1527–1533 (1990)).

The following experimental examples are offered by way of illustration and not by way of limitation.

6. EXAMPLE 1

Regulation of Cyclin-Dependent Kinase 5 and Casein Kinase I by Metabotropic Glutamate Receptors This example demonstrates that the signaling molecules CKI and Cdk5 regulate DARPP-32 phosphorylation, and that metabotropic glutamate receptors (mGluRs) produce their effects on DARPP-32 phosphorylation states through the activity of these signaling molecules. It demonstrates that (S)-3,5-Dihydroxyphenylglycine (DHPG), an agonist for group I metabotropic glutamate receptors, stimulates CKI and Cdk5 activities in neostriatal neurons, leading to enhanced phosphorylation, respectively, of Ser-137 and Thr-75 of DARPP-32.

6.1. INTRODUCTION

Metabotropic glutamate receptors (mGluRs) are a major class of excitatory amino acid receptors found throughout the nervous systems of animals, including humans. There are currently 8 subtypes of mGluR and these receptors belong to a family of G-protein coupled receptors that exert effects by direct modulation of ion channels or formation of second messengers. There are three recognized subgroups of mGluRs, known as group I (mGluR1 and mGluR5), group II (mGluR2 and mGluR3), and group III (mGluR4, mGluR6, mGluR7 and mGluR8), that have been classified based on their pharmacological profile, sequence homology, and coupling to second messenger formation. Activation of group I mGluRs results in stimulation of phosphatidylinositide hydrolysis, whereas activation of group II and III mGluRs results in inhibition of forskolin-induced cyclic adenosine monophosphate (cAMP) formation.

Although research has focused on identifying the location of mGluRs in neuronal tissues, little is known about the signaling pathways linked to mGluR activity. Therefore, experiments were performed to elucidate the pathways involved in mGluR activity in neuronal tissue in order to better understand the role that mGluRs have in modulating neuronal function as well as to identify signaling molecules linked to mGluRs that can be exploited as therapeutic targets. The regulation of casein kinase I (CKI) and cyclin-dependent kinase 5 (Cdk5) by glutamate and mGluRs was examined in neostriatal neurons.

The results indicate that CKI, Cdk5, PP2A, and PKA are all involved in the regulation of DARPP-32 phosphorylation and that mGluRs produce their effects on DARPP-32 phosphorylation states through the activity of these signaling molecules. It was found that agonists of mGluRs stimulate activity of CKI, which in turn stimulates activity of Cdk5, leading to phosphorylation of Thr75 of DARPP-32. In addition, CKI stimulation can lead to direct phosphorylation of Ser137 of DARPP-32.

6.2. MATERIALS AND METHODS

6.2.1. ANTIBODIES, PLASMIDS AND CHEMICALS

A phospho-specific antibody that recognizes phospho-Ser-137 DARPP-32 was developed by immunizing rabbits with a peptide encompassing phospho-Ser-137 of DARPP-32 conjugated with limulus hemocyanin (Sigma). Phospho-Thr-75 DARPP-32 antibody was developed as disclosed (Bibb et al., 1999, Nature (Lond.) 402:669–671). Antibodies were purified by affinity chromatography as disclosed (Czemik et al., 1997, *Regulatory Protein Modification* (Humana, Totowa, N.J.)). The expression plasmid pCEP4HA-CK1ε was obtained from David Virshup (University of Utah, Salt Lake City). Anti-hemagglutinin (HA) was obtained from Roche Molecular Biochemicals. CKI-7 (CKI-7) was obtained from Seikagaku Kogyo, Tokyo. (S)-3,5-Dihydroxyphenylglycine ("DHPG" or "(S)-3,5-DHPG") and L-AP3 were obtained from Tocris Neuramin, Bristol, U.K. Protease inhibitor cocktail tablet was obtained from Roche Molecular Biochemicals.

6.2.2. PREPARATION AND TREATMENT OF STRIATAL SLICES

Neostriatal slices were prepared from male C57/BL6 mice (6–8 weeks old) in accordance with methods known in the art (Nishi, A. et al. 1997, *J. Neurosci.* 17:8147–8155). Slices were treated with a drug. After drug treatment, slices were immediately frozen in liquid nitrogen, and stored at −80° C. until assayed.

6.2.3. IMMUNOBLOTTING

Frozen slices were sonicated in hot homogenization buffer containing 1% SDS and 50 mM NaF, and samples were boiled for 10 minutes. SDS-PAGE sample buffer was then added and samples were boiled for 5 minutes. Samples (approximately 120 µg of total protein) were separated by SDS-PAGE (10% polyacrylamide) and then transferred to nitrocellulose. In most studies, immunoblots were first probed with anti-phospho-Ser137 DARPP-32 antibody. The blots were then stripped and probed with anti-phospho-Thr75 DARPP-32 antibody. Blots were stripped again and probed with anti-total DARPP-32 antibody. Antibody binding was revealed using an enhanced chemiluminescence (ECL) immunoblotting detection system. Chemiluminescence was detected by autoradiography and bands were quantified by analysis of scanned images using NIH IMAGE 1.52 software. Data were statistically analyzed by Student's t test in Microsoft EXCEL™ software as indicated.

6.2.4. Transient Transfection of N2a Cells

Neuroblastoma N2a cells were cultured in DMEM containing 5% fetal bovine serum (FBS) to 50–60% confluency. Four micrograms of the expression plasmid for HA-CK1ε were transfected into N2a cells in 100 mm dishes using FuGENE™ 6. Twenty-four hours after transfection, cells were incubated in phosphate-buffered Krebs-Henseleit solution (Sigma) for 10 minutes at room temperature. Cells were then incubated with or without CKI inhibitor for 30 minutes before treating with the group I mGluR agonist (S)-3,5-DHPG (100 µM) for 2 minutes. Cells were then lysed in one ml of lysis buffer containing 1% Nonidet P-40 (NP-40), 150 mM NaCl, 0.1% SDS, 50 mM Tris (pH 8.0), 5 mM $Na_3VO_4$, 20 mM NaF, 20 mM β-glycerol-phosphate and protease inhibitors. Lysates were centrifuged at 10,000 g and supernatants were used for immunoprecipitation and kinase assay.

6.2.5. IMMUNOPRECIPITATION OF CKI AND CDK5 AND KINASE ASSAYS

For immunoprecipitation of CKI from N2a cells, lysates (1 mg of total protein) were pre-cleared with 5 µl of mouse IgG and 50 µl of protein A agarose for 30 minutes. Five µl of anti-HA antibody were added and samples were incubated for 1 hour at 4° C. Five µl of anti-mouse rabbit IgG and 50 µl of protein A agarose were then added for 45 minutes. Immuno-complexes were washed three times in lysis buffer, two times in kinase buffer (30 mM Hepes (pH 7.5), 7 mM $MgCl_2$, 0.5 mM DTT). CKI assays were performed in a 30 µl assay volume with 2 µg of purified DARPP-32, 500 µM ATP and 5 µCi $\gamma$-$^{32}$P-ATP. Samples were incubated at 30° C. for 20 minutes, reactions were stopped by addition of SDS-sample buffer, and samples were boiled for 5 minutes. Samples were separated by SDS-PAGE (12% polyacrylamide). SDS-PAGE gels were dried and exposed to Kodak film for autoradiography. Bands were quantified by analysis using a Molecular Dynamics PhosphorImager.

For Cdk5 immunoprecipitation, striatal tissue slices (approximately 150 µg total protein) were lysed using a Dounce homogenizer and 1 ml of lysis buffer (150 mM NaCl, 20 mM Tris-HCl (pH 7.4), 1 mM EDTA, 0.5% NP-40, 5 mM NaF, 5 mM $Na_3PO_4$ and protease inhibitors). Lysates were centrifuged at 10,000 g for 10 minutes at 4° C. Supernatants were pre-cleared by adding rabbit IgG-conjugated agarose for 40 minutes at 4° C. Ten µl of Cdk5 antibody conjugated to agarose were added and samples were incubated for 1 hour at 4° C. with mixing. Agarose pellets were collected and washed three times with 1 ml of lysis buffer and two times with kinase assay buffer (50 mM Hepes (pH 7.5), 10 mM $MgCl_2$, 1 mM DTT). Cdk5 kinase assays were performed in a 30-µl reaction mixtures with 2 µg Histone H-1, 500 µM ATP and 5 µCi of $\gamma$-$^{32}$P-ATP. Samples were incubated at 30° C. for 10 minutes, reactions were stopped by addition of SDS-sample buffer, and samples were boiled for 5 minutes. Samples were separated by SDS-PAGE and analyzed as disclosed above for CKI assays. Data were analyzed by Student's t-test in Microsoft Excel software as indicated, with significance defined as $p<0.05$.

6.2.6. In vitro phosphorylation of CDK5 and p35 by CKI

Cdk5 and p35-his$_6$ were purified from insect Sf9 cultures after expression of protein using baculovirus vectors. To examine phosphorylation of Cdk5 or p35 by CK1α (New England Biolabs), 1 µM Cdk5 or 1.5 µM p35 was incubated with 2 units/µl of CK1 in 50 mM Tris-HCl (pH 7.5), 10 mM MgCl$_2$, 0.5 mM DTT, 200 µM ATP, and 0.6 mCi/ml [γ-$^{32}$P] ATP. Samples were analyzed by SDS/PAGE and autoradiography.

6.2.7. WHOLE-CELL RECORDINGS OF VOLTAGE-DEPENDENT Ca$^{2+}$ CHANNELS

Neostriatal neurons from 3- to 4-week-old mice were acutely dissociated by using procedures similar to those disclosed in Eberwine et al. (1995, Prog. Brain Res. 105: 117–126). Whole-cell current recordings used standard voltage-clamp techniques. The internal solution consisted of 180 mM N-methyl-D-glucamine, 40 mM Hepes, 4 mM MgCl$_2$, 0.5 mM 1,2-bis(2-aminophenoxy)ethane-N,N,N',N'-tetraacetate, 12 mM phosphocreatine, 2 mM Na$_2$ATP, 0.2 mM Na$_3$GTP, 0.1 mM leupeptin (pH 7.2–7.3), 265–270 mosm/liter. The external solution consisted of 135 mM NaCl, 20 mM CsCl, 1 mM MgCl$_2$, 10 mM Hepes, 0.001 mM tetrodotoxin, 5 mM BaCl$_2$, 10 mM glucose (pH 7.3), 300–305 mosm/liter. Recordings were obtained with an Axon Instruments 200B patch clamp amplifier that was controlled and monitored with an IBM PC running PCLAMP™ (v. 8) with a DigiData 1320 series interface (Axon Instruments, Foster City, Calif.). Electrode resistances were typically 2–4 MΩ in the bath. After seal rupture, series resistance (4–10 MΩ) was compensated (70–90%) and periodically monitored. Drugs were applied with a gravity-fed "sewer pipe" system. The array of application capillaries was positioned 250 µm from the cell under study. Solution changes were effected by altering the position of the array with a DC drive system controlled by a microprocessor-based controller (Newport-Klinger, Irvine, Calif.). Data analyses were performed with AXOGRAPH™ (Axon Instruments), KALEIDAGRAPH™ (Albeck Software, Reading, Pa.), and STATVIEW™ (Abacus Concepts, Berkeley, Calif.).

6.3. RESULTS

6.3.1. EFFECT OF GROUP I mGluR AGONIST ON PHOSPHORYLATION OF DARPP-32 AT THR75 AND SER137

Neostriatal slices prepared from mouse brain (C57/BL6) were used. Slices were treated with the group I mGluR agonist, (S)-3,5-DHPG and the effect of this agonist on the phosphorylation of DARPP-32 at two sites, Ser137 and Thr75 was assessed using phosphorylation state-specific antibodies. Treatment of slices with (S)-3,5-DHPG (100 µM) resulted in a rapid but transient increase in phosphorylation of both Ser137 and Thr75 in DARPP-32 (FIG. 1A). The level of phosphorylation of Ser137 reached a peak at 2 minutes, and declined quickly to the basal level by 5 minutes. Similar results were observed for the effect of DHPG on phosphorylation of Thr75. Pretreatment of slices with the mGluR antagonist L-AP3 (100 µM) for 20 minutes blocked both effects of the agonist (DHPG) (FIG. 1B). The stoichiometry of Ser137 phosphorylation in mouse neostriatal slices was determined to be 0.4 mol/mol. Previous studies have shown that the stoichiometry of phosphorylation of Thr75 is approximately 0.26 mol/mol. Therefore, the 2–3-fold increase in phosphorylation of both Ser137 and Thr75 in response to group I mGluR activation was considered to be substantial.

6.3.2. EFFECT OF GROUP I mGluR AGONIST on CDK5 and CKI ACTIVITIES

Experiments were then performed to determine if the ability of the group I mGluR agonist to increase phosphorylation of DARPP-32 was related to direct activation of both CKI and Cdk5. Alternatively, one of these kinases may be activated and increase phosphorylation at its target site, but the increase at the other site may be indirect via an enzyme-directed or a substrate-directed effect on the respective protein kinase or protein phosphatase for that other site. In previous studies, it had been found that enzyme-directed and substrate-directed effects of phosphorylation of DARPP-32 had occurred at Thr75, Ser102, and Ser137 (Desdouits et al. 1995, Proc. Natl. Acad. Sci. USA 92:2682–2685; Bibb et al., 1999, Nature 402:669–671; Girault et al., 1989, J. Biol. Chem. 264:21748–21759).

In initial experiments, CKIα, CKIε and CKIδ were found to be highly expressed in the striatum, suggesting that CKIε and/or CKIδ are possibly subject to regulation by mGluR activation. As none of the commercially available CKI antibodies proved useful for immunoprecipitation, a transient transfection system using N2a cells was employed. A screen for different subtypes of group I mGluRs indicated that mGluR1 is expressed in N2a cells. HA-tagged CKIε was transiently transfected into neuroblastoma N2a cells and cells were treated with DHPG for 2 minutes. CKIε was immunoprecipitated using anti-HA antibody and CKI activity was assayed using DARPP-32 as substrate (FIG. 3). Treatment of cells with DHPG resulted in an approximately 2-fold increase in CKI activity compared to the basal level. Addition of CKI-7 (100 µM) blocked the ability of DHPG to increase CKI activity (FIG. 3).

Using an antibody, Cdk5 was immunoprecipitated from homogenates obtained from neostriatal slices and assayed using histone H-1 as substrate. Treatment of slices with DHPG caused a rapid but transient increase in Cdk5 kinase activity. After 2 minutes, Cdk5 activity was increased approximately 4-fold, with activity declining back to the basal level after 5 minutes (FIG. 2). Therefore, Cdk5 and CKI are signaling molecules that can be directly exploited in order to bypass the mGluR in order to modulate DARPP-32 phosphorylation.

6.3.3. EFFECT OF CDK5 AND CKI INHIBITORS ON PHOSPHORYLATION OF DARPP-32 AT THR75 AND SER137

The similar time course of activation of both CKI and Cdk5 kinase by DHPG suggested that the two kinases may be regulated as part of a common signaling pathway. CKI may also regulate Cdk5 kinase activity in response to mGluR receptor activation, or vice versa. To examine these possibilities, experiments were performed with a CKI inhibitor, CKI-7. The crystal structure of the catalytic domain of casein kinase I complexed with CKI-7 provided evidence that CKI-7 achieves its selectivity for CKI by hydrophobic contacts and hydrogen bonding with the isoquinoline ring (Xu, R. M. et al. 1996. Proc. Natl. Acad. Sci. USA 93:6308–6313). In in vitro studies, the inhibitory potency (IC$_{50}$ values) for CKI-7 towards CKI and Cdk5/p25 was determined. The IC$_{50}$ of CKI-7 for CKI was 15 µM and for Cdk5 was 200 μM. These data indicate that CKI-7 can be used to distinguish between CKI and Cdk5 in intact cell studies.

Neostriatal slices were pre-incubated with different concentrations of CKI-7 for 30 minutes before treatment with DHPG for 2 minutes. With 50 μM CKI-7, there was little effect on basal or DHPG-stimulated levels of DARPP-32 phosphorylation at either Ser137 or Thr75. With increasing doses of CKI-7 (100 to 300 μM), there were dose-dependent decreases in both basal and DHPG-stimulated DARPP-32 phosphorylation at Ser137 and Thr75. Then, Cdk5 kinase activity was measured following treatment of slices with the CKI inhibitor, and immunoprecipitation. The effect of DHPG on Cdk5 kinase activity was attenuated by CKI-7 in a dose-dependent manner.

To examine whether Cdk5 may have an effect on CKI, butyrolactone, a specific inhibitor of Cdk5, was used in studies of DARPP-32 phosphorylation. Slices were pre-incubated with different concentrations of butyrolactone for 30 minutes before treatment with DHPG for 2 minutes (FIG. 4). With a 1 μM butyrolactone dose, there was little effect on basal or DHPG-stimulated levels of DARPP-32 phosphorylation at either Ser137 or Thr75. However, at higher doses of butyrolactone (5 μM and 10 μM), both basal and DHPG-stimulated phosphorylation of Thr75 were decreased in a dose-dependent manner. However, basal and DHPG-stimulated phosphorylation of Ser137 were unaffected by butyrolactone. Together, these data indicated that DHPG activates CKI and that CKI then activates Cdk5, but that Cdk5 has no direct effect on CKI. Further, these data provide additional details on the signaling pathways linked to mGluR activity.

6.3.4. IN VITRO, CKI PHOSPHORYLATES P35

Experiments were then performed to investigate the mechanism by which CKI regulates Cdk5. The phosphorylation of the Cdk5 catalytic subunit or its regulatory subunit, p25, by CKI, was examined. Experiments performed in vitro demonstrated that CKI was able to efficiently phosphorylate p25, but phosphorylated Cdk5 catalytic subunit to a much lesser extent (FIG. 5). Incubation of cells with higher concentrations of CKI for longer times resulted in phosphorylation of p25 to approximately 2 mol/mol.

6.3.5. ACTIVATION OF mGluRs REGULATES $Ca^{2+}$ CHANNELS THROUGH A MECHANISM INVOLVING CKI, CDK5, AND DARPP-32

The potential effect of CKI and Cdk5 on $Ca^{2+}$ channels was examined in neostriatal neurons. Treatment with CKI-7 (FIGS. 6A–B) or butyrolactone (FIGS. 6C–D) caused a significant reduction in basal $Ca^{2+}$ currents, suggesting that constitutively active CKI and Cdk5 are involved in maintaining active $Ca^{2+}$ channels under basal conditions. Addition of the group I mGluR agonist, DHPG, enhanced these $Ca^{2+}$ currents within 90 seconds, similar to the time course of enhanced phosphorylation on Ser137 (CKI site) and Thr75 (Cdk5 site) of DARPP-32. Furthermore, the enhancement of $Ca^{2+}$ currents by DHPG was eliminated by the addition of CKI-7 or butyrolactone. Together, these data demonstrate that group I mGluRs up-regulate calcium channel activity via the activation of CKI and Cdk5.

Figure 6E:
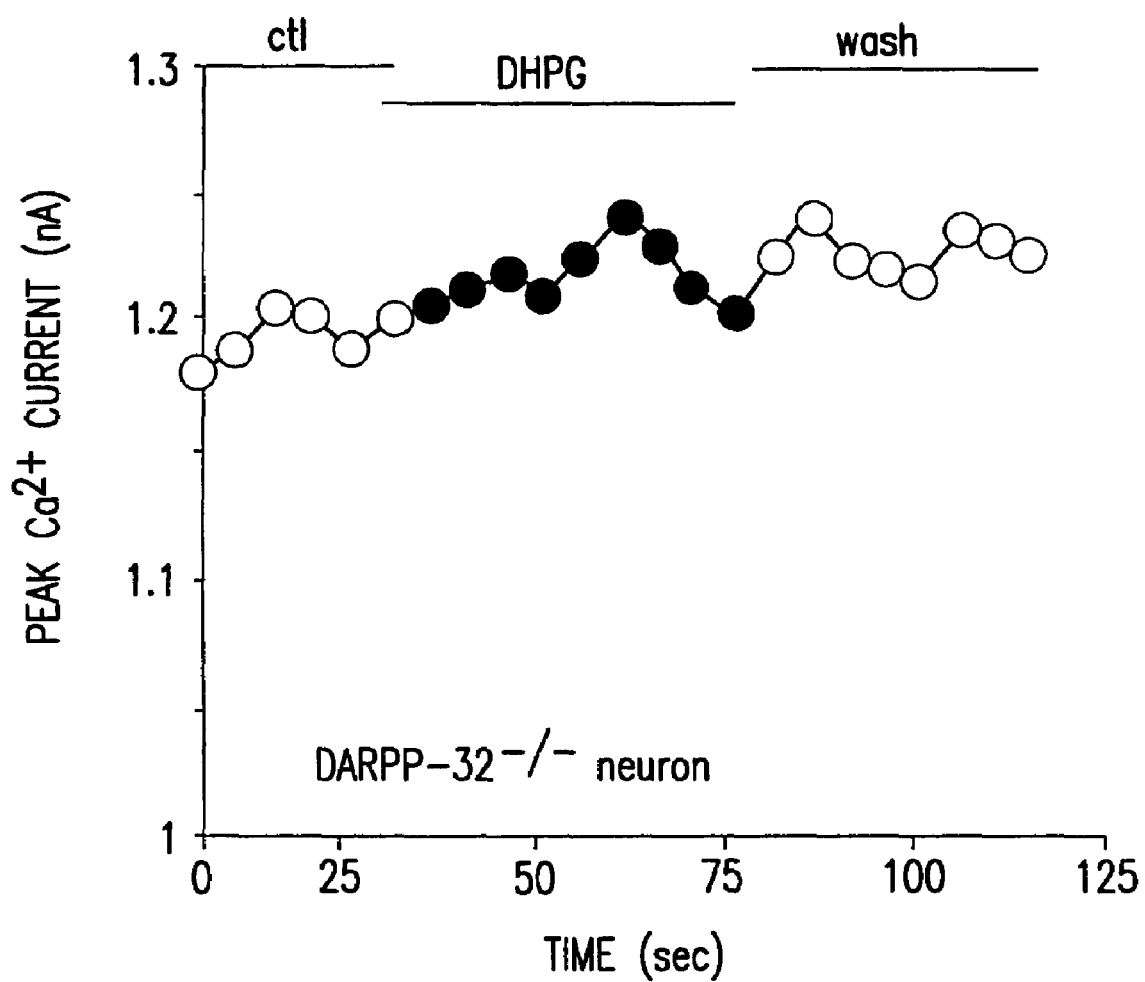

These effects of mGluR agonists on calcium channels were also tested in DARPP-32 knock-out mice. In nine out of ten neurons, the effect of DHPG on $Ca^{2+}$ channels was completely eliminated. A representative experiment is shown in FIG. 6E.

6.4. Discussion

Details of the signaling pathways linked to activation of metabotropic glutamate receptors have now been elucidated, demonstrating that CKI and Cdk5 are key molecules. Further, an endpoint of signaling has been identified, which is regulation of voltage-gated calcium channels. It is also known that CKI and Cdk5 are involved in maintaining basal calcium channel activity while mGluRs can enhance the basal calcium currents through activation of CKI and Cdk5. These data link the activity of CKI and Cdk5 and its regulation by mGluRs with biologically significant processes that regulate neuronal function. Moreover, these data provide information on signaling molecules that may be targeted by therapeutic strategies apart from targeting of mGluRs directly.

The results of these experiments indicate that CKI and Cdk5 are involved in the regulation of DARPP-32 phosphorylation and that mGluRs produce their effects on DARPP-32 phosphorylation states through the activity of these signaling molecules. For example, it has been found that agonists of mGluRs stimulate activity of CKI, which in turn stimulates activity of Cdk5, leading to phosphorylation of Thr75 of DARPP-32. In addition, CKI stimulation can lead to direct phosphorylation of Ser137 of DARPP-32.

Furthermore, PP2A is known to dephosphorylate Thr75 of DARPP-32, mimicking the actions of metabotropic glutamate receptor antagonists. This indicates that inhibition of PP2A mimics a metabotropic glutamate receptor agonist and that activation of PP2A mimics a mGluR antagonist. Finally, it is known that PKA phosphorylates Thr34 of DARPP-32. Therefore, the signaling pathways involved in phosphorylation of DARPP-32 are complex. The signaling molecules that may be targeted for therapeutic purposes as a way to modulate neuronal function therefore include PP2A and PKA, as well as CKI and Cdk5, as demonstrated by this example.

7. EXAMPLE 2

Mechanism of Regulation of Casein Kinase I Activity by Group 1 Metabotropic Glutamate Receptors In this example, the signaling pathway that leads from mGluRs to CK1 activation was investigated. In neostriatal slices, the effect of DHPG on phosphorylation of Ser-137 or Thr-75 of DARPP-32 was blocked by the PLCβ inhibitor U73122, the $Ca^{2+}$ chelator BAPTA/AM and the calcineurin inhibitor, cyclosporin A. In N2a cells, the effect of DHPG on the activity of transfected HA-tagged CK1ε was blocked by BAPTA/AM and cyclosporin A. In neostriatal slices, the effect of DHPG on Cdk5 activity was also abolished by BAPTA/AM and cyclosporin A. Metabolic labeling studies and phosphopeptide mapping revealed that HA-CK1ε was transiently dephosphorylated in N2a cells upon treatment with DHPG and this was blocked by cyclosporin A. A mutant CK1ε with a nonphosphorylatable C-terminal domain was not activated by DHPG. The studies disclosed in this example demonstrate that DHPG activates CK1ε via a signaling cascade involving activation of PLCβ, an increase in intracellular $Ca^{2+}$, $Ca^{2+}$-dependent stimulation of calcineurin and subsequent dephosphorylation of inhibitory C-terminal autophosphorylation sites.

7.1. INTRODUCTION

Casein Kinase 1 (CK1) was one of the first serine/threonine protein kinases to be isolated and characterized. There are at least seven mammalian CK1 isoforms: α, β, γ1, γ2, γ3, δ and ε (1,2), and distinct CK1 family members are likely to have a variety of roles in eukaryotic cells. An increasing number of potential physiologic substrates for CK1 isoforms have been identified. CK1α phosphorylates M1 and M3-muscarinic receptors and rhodopsin in an agonist-dependent manner (3,4). CK1δ and CK1ε phosphorylate N-terminal residues of p53 in vitro and in vivo, and DNA damaging drugs enhance this activity (4–6). CK1 is an important regulator of β-catenin in the Wnt pathway: CK1ε mimicked Wnt in inducing a secondary axis in Xenopus, stabilizing β-catenin, and stimulating β-catenin-dependent gene transcription (7–10), whereas recent studies showed that depletion of CK1α, but not CK1ε, prevents β-catenin phosphorylation and degradation, suggesting that CK1α plays a negative role in Wnt signaling (11,12). In Drosophila, the double-time gene product, a CK1ε homolog, has been found to interact with dPER and regulate circadian cycle length (13). CK1δ and CK1ε have also both been implicated in the regulation of the circadian clock in mammals (14–16).

CK1 family members contain a highly related, central kinase domain that is flanked by N- and C-terminal extensions of variable length. The amino acid sequences of the C-terminal extensions are in general not highly related. However, the 124-amino acid C-terminal domain of mammalian CK1ε is 50% identical to that of CK1δ. Notably, several in vitro studies have shown that the activities of CK1δ and CK1ε are regulated by autophosphorylation of their respective C-terminal domains (17,18). Autophosphorylation of at least 8 sites leads to inhibition of kinase activity. Moreover, it has been shown in vitro that treatment of CK1ε with any of several different serine/threonine phosphatases including PP1, PP2A and PP2B (calcineurin) causes a marked increase in kinase activity (14,18,19). Dephosphorylation of CK1δ and CK1γ isoforms by the catalytic subunit of PP1 has also been found in vitro to result in enzyme activation (17).

The previous example demonstrated that both CK1 and Cdk5 are regulated by activation of metabotropic glutamate receptors (mGluRs) in neostriatal neurons (see also, 20). DHPG, an agonist for group I mGluRs, increased CK1 and Cdk5 activities in neostriatal slices, leading to enhanced phosphorylation of Ser-137 and Thr-75 of DARPP-32, respectively. The effects of DHPG on both Ser-137 and Thr-75 were blocked by CK1–7, a specific inhibitor of CK1, demonstrating that activation of Cdk5 by mGluRs required activation of CK1. The DHPG-induced increase in Cdk5 activity, subsequently measured in extracts of neostriatal slices, was abolished by treatment of slices with CK1–7. Finally, treatment of acutely dissociated neurons with DHPG enhanced voltage-dependent $Ca^{2+}$ currents. This enhancement was eliminated by either CK1–7 or butyrolactone (an inhibitor of Cdk5), indicating that CK1 and Cdk5 may be involved in the regulation by mGluR agonists of $Ca^{2+}$ channels.

In this example, the pathway and mechanism underlying CK1 activation in response to group I mGluR agonists was investigated. The results obtained demonstrated a signal transduction pathway in which group I mGluRs increase intracellular $Ca^{2+}$ and stimulate calcineurin to dephosphorylate autoinhibitory phosphorylation sites in CK1ε. Transient dephosphorylation and subsequent autophosphorylation of CK1ε leads to transient activation and inactivation, respectively, of the enzyme.

7.2. MATERIALS AND METHODS

7.2.1. ANTIBODIES, PLASMIDS AND CHEMICALS

Phospho-specific antibodies that recognize either phospho-Ser137 DARPP-32 or phospho-Thr75 DARPP-32 antibody were developed as disclosed (20, 21). The expression plasmids pCEP4HA-CK1ε and pCS-Myc-MM2-CK1ε were prepared as disclosed (19). Anti-HA (12CA5) was obtained from Boehringer Mannheim and anti-Myc (9E10) was obtained from Upstate Biotechnology. Anti-Cdk5 (C-8) and anti-CK1ε were obtained from Santa Cruz. U73122, BAPTA/AM and cyclosporin A were obtained from Calbiochem; (S)-3,5-DHPG, ZM241385 and L-AP3 were obtained from Tocris. Protease inhibitor cocktail tablets were obtained from Boehringer Mannheim. Lambda protein phosphatase was obtained from Upstate Biotechnology.

7.2.2. PREPARATION AND TREATMENT OF STRIATAL SLICES

Neostriatal slices were prepared from male C57/BL6 mice (6–8 weeks old) as disclosed (22). Slices were treated with drugs as specified in the text and figure legends. After drug treatment, slices were immediately frozen in liquid nitrogen, and stored at −80° C. until assayed.

7.2.3. IMMUNOBLOTTING

Frozen slices were sonicated in hot homogenization buffer containing 1% SDS and 50 mM NaF, and samples were boiled for 10 min. SDS-PAGE sample buffer was then added and samples were boiled for 5 min. Samples (approximately 120 μg protein) were separated by SDS-PAGE (10% polyacrylamide) and transferred to nitrocellulose. Immunoblots were first probed with antiphospho-Ser-137 DARPP-32 antibody. The blots were stripped and probed with anti-phosphoThr-75 DARPP-32 antibody. Blots were stripped again and probed with anti-total DARPP-32 antibody. Antibody binding was detected by enhanced chemiluminescence (ECL) using X-ray film, and images were analyzed by laser scanning densitometry using NIH Image 1.52 software. Data were statistically analyzed by Student's t-test using Microsoft EXCEL™ software as indicated.

7.2.4. TRANSFECTION, IMMUNOPRECIPITATION AND KINASE ASSAYS

Neuroblastoma N2a cells were cultured to 50–60% confluence in DMEM containing 5% fetal bovine serum. Four μg of the expression plasmid for HA-CK1ε or myc-MM2-CK1ε was transfected into N2a cells in 100 mm dishes using FuGENE6™. Twenty-four hours after transfection, cells were incubated at room temperature in phosphate-buffered Kreb's-Henseleit solution (Sigma) for 10 min and then with or without inhibitors for 30 min before treating with (S)-3, 5-DHPG, for 2 min. Cells were then lysed in 1 ml of radio-immunoprecipitation (RIPA) buffer containing 1% NP-40, 150 mM NaCl, 0.1% SDS, 50 mM Tris, pH 8.0, 5 mM $Na_3VO_4$, 20 mM NaF, 20 mM β-glycerol-phosphate and protease inhibitors. Lysates were centrifuged at 10,000 g, and supernatants were used for immunoprecipitation and kinase assay.

For immunoprecipitation of CK1ε from N2a cells, lysates (1 mg of total protein) were precleared with 5 μl of mouse IgG (ICN) and 50 μl of protein A agarose for 30 min. Five μl (approximately 2 μg) of anti-HA or anti-myc antibody was added and samples were incubated for 1 h at 4° C. Five μl of anti-mouse rabbit IgG and 50 μl of protein A agarose were then added for 45 min. Immuno-complexes were washed 3 times in lysis buffer and 2 times in kinase buffer (30 mM Hepes, pH 7.5, 7 mM $MgCl_2$, 0.5 mM DTT).

CK1 assays were performed in a 30 μl assay volume with 2 μg of purified DARPP-32, 500 μM ATP and 5 μCi $\gamma$-$^{32}$P-ATP. Reactions were started by addition of the ATP. Samples were incubated at 30° C. for 10 min and reactions were stopped by addition of SDS-sample buffer and boiled for 5 min. Samples were separated by SDS-PAGE (12% polyacrylamide). SDS-PAGE gels were dried and exposed to Kodak film for autoradiography. Results were quantified using a Molecular Dynamics PHOSPHORIMAGER™. Immunoprecipitation and assay of Cdk5 were performed as disclosed (20).

For experiments in which the effect of protein phosphatase on CK1ε activity was measured, immunoprecipitated CK1ε, from N2a cells treated with DHPG, was added to a mixture consisting of 50 mM Tris-HCl, 0.1 mM $Na_2EDTA$, 5 mM DTT, 2 mM $MnCl_2$, and 200 units lambda phosphatase (Upstate Biotechnology #14-405). Control reactions without lambda protein phosphatase were also carried out. Dephosphorylation reactions were carried out at 37° C. for 15 min. To stop the reactions, beads with CK1ε were washed 3 times with RIPA buffer, and two times with kinase buffer (30 mM Hepes, pH 7.5, 7 mM $MgCl_2$, 0.5 mM DPI). Kinase activity was measured as disclosed above.

7.2.5. METABOLIC LABELING AND TWO-DIMENSIONAL PHOSPHOPEPTIDE MAPPING

Twenty-four hours after transfecting N2a cells with CK1ε expression plasmids, cells were incubated in 200 μCi/ml (NEN) $^{32}$P-inorganic phosphate and phosphate-free serum-free DMEM for 2 h. Cyclosporin A was added to the transiently transfected cultures at a final concentration of 1 μM during the last 30 min of metabolic labeling. Cells were treated with DHPG for various periods of time as indicated, harvested by lysis in RIPA buffer and clarified by centrifugation at 14,000×g for 10 min. Soluble extracts containing HA- or Myc-tagged proteins were immunoprecipitated with 12CA5 or 9E10 monoclonal antibody and protein A-agarose. The immunoprecipitates were eluted from the protein A-agarose and separated by SDS-PAGE on 10% gel. Proteins were stained briefly with Coomassie Brilliant Blue, the gels were dried, and the labeled proteins were visualized by autoradiography.

Radiolabeled protein bands were excised, rehydrated, de-stained and dried in a speedvac. The gel slices were minced and rehydrated in 75 μg/ml TPCK/trypsin in 50 mM $NH_4CO_3H$ (1 ml final volume) for 24 h at 37° C. The supernatant was removed from the gel slices and then lyophilized to dryness. Recovery of tryptic phosphopeptides was determined by Cerenkov counting. The two-dimensional peptide mapping method was used to separate phosphopeptides (23). Lyophilized tryptic peptides were suspended in 10 μl of electrophoresis buffer (10% acetic acid and 1% pyridine, pH 3.5) and spotted onto thin-layer cellulose plates (20×20 cm, Analtech). Electrophoresis was carried out at 400 V for 1.5 h. Following electrophoresis, cellulose plates were dried and then subjected to ascending chromatography in buffer containing 25% 1-butanol, 7.5% acetic acid and 37.5% pyridine. Phosphopeptides were visualized using a PHOSPHORIMAGER™ (Molecular Dynamics).

7.3. RESULTS

7.3.1. THE EFFECT OF DHPG ON SER-137 AND THR-75 PHOSPHORYLATION OF DARPP-32 IS BLOCKED BY U73122, BAPTA AND CYCLOSPORIN A

The previous example (Section 6) demonstrated that DHPG, an agonist for group I mGluRs, increased CK1 and Cdk5 activities in neostriatal slices, leading to enhanced phosphorylation of Ser-137 and Thr-75 of DARPP-32, respectively. Activation of group I mGluRs results in the stimulation of phosphoinositide hydrolysis (24). Therefore, DHPG-dependent activation of CK1 may involve activation of PLCβ. However, it has also been reported that DHPG can potentiate the response of adenosine A2a receptors to agonist (25,26), raising the possibility of an involvement of other signal transduction pathways. The effect of the specific PLCβ inhibitor, U73122, was tested in neostriatal slices. Preincubation with 10 μM U73122 for 30 min did not change the basal phosphorylation of Ser-137 or Thr-75 but the effect of DHPG was abolished (FIG. 7). In contrast, the adenosine A2a receptor antagonist, ZM241385 (100 μM), did not affect the ability of DHPG to stimulate phosphorylation of Ser-137 or Thr-75. These results supported a role for a signal transduction pathway involving PLCβ.

Activation of PLCβ, leads to production of inositol 1,4,5-triphosphate ($IP_3$) and release of $Ca^{2+}$ from the endoplasmic reticulum. To examine the role of $Ca^{2+}$, we used the $Ca^{2+}$ chelator, BAPTA/AM, in studies in slices. Pre-incubation with 20 μM BAPTA/AM did not change the basal phosphorylation of DARPP-32 but the effect of DHPG was abolished (FIG. 7). Moreover, treatment of slices with the $Ca^{2+}$ ionophore, ionomycin (2 μM), resulted in increased phosphorylation of both Ser-137 and Thr-75 of DARPP-32 (FIG. 7). We hypothesized that the increased intracellular $Ca^{2+}$ activates the $Ca^{2+}$-dependent protein phosphatase, calcineurin (PP2B), to dephosphorylate inhibitory autophosphorylation sites on CK1ε. Calcineurin is expressed at a high level in striatum (27). Treatment of slices with cyclosporin A (5 μM), a specific calcineurin inhibitor, for 1 h attenuated the effect of DHPG on phosphorylation of Ser-137 and Thr-75 of DARPP-32 (FIG. 7).

7.3.2. THE EFFECT OF DHPG ON CK1ε ACTIVITY IS BLOCKED BY U73122, BAPTA AND CYCLOSPORIN A

To further characterize the effect of DHPG on CK1ε activity, we used a transfection system. An expression plasmid containing HA-tagged CK1ε was transiently transfected into N2a cells and cells were treated with DHPG for 2 min. CK1ε was immunoprecipitated using anti-HA antibody and CK1ε activity was assayed using DARPP-32 as substrate (FIG. 8). An initial screen for different subtypes of group I mGluRs indicated that mGluR1 and mGluR5 are both expressed in N2a cells. Treatment of cells with DHPG resulted in an increase in CK1ε activity and this effect was blocked by the group I mGluR antagonist L-AP3 (FIG. 8).

Pre-incubation of cells with U73122 (10 μM), BAPTA/AM (20 μM) or cyclosporin A (1 μM) abolished the effect of DHPG on CK1ε activity, consistent with a role for $Ca^{2+}$-dependent activation of calcineurin in the regulation of CK1ε.

7.3.3. DHPG REGULATES CDK5 KINASE ACTIVITY THROUGH A PLCB/$Ca^{2+}$/CALCINEURIN PATHWAY

It was previously demonstrated by using specific CK1 inhibitors that group I mGluRs activate Cdk5 kinase activity via a pathway that involves CK1. To further examine whether Cdk5 activation by DHPG is through a PLCβ/$Ca^{2+}$/calcineurin pathway, Cdk5 kinase activity following its immunoprecipitation from mouse neostriatal slices was analyzed. DHPG increased Cdk5 activity and preincubation of mouse neostriatal slices with U73122 (10 μM), BAPTA/AM (20 μM) or cyclosporin A (5 μM) abolished this effect (FIG. 9). Treatment of slices with ionomycin (2 μM) for 2 min also resulted in an increase in Cdk5 kinase activity by 2-fold, and the effect of ionomycin was blocked by cyclosporin A (5 μM).

7.3.4. DHPG TREATMENT INDUCES TRANSIENT DEPHOSPHORYLATION OF CK1ε

Figure 10A:
Figure 10B:
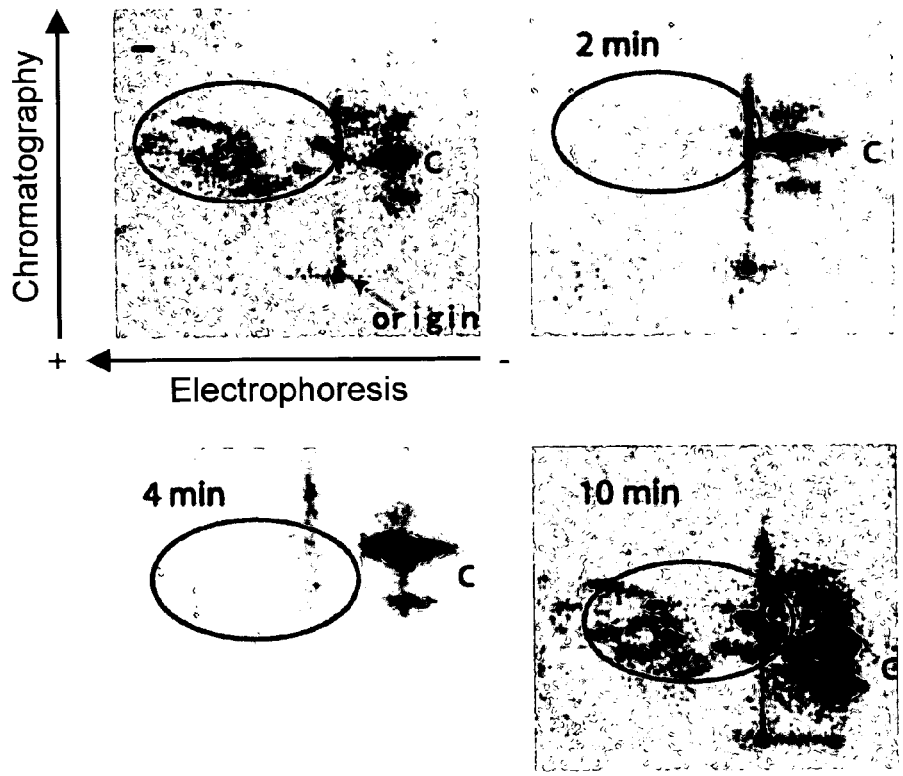
Figure 10C:
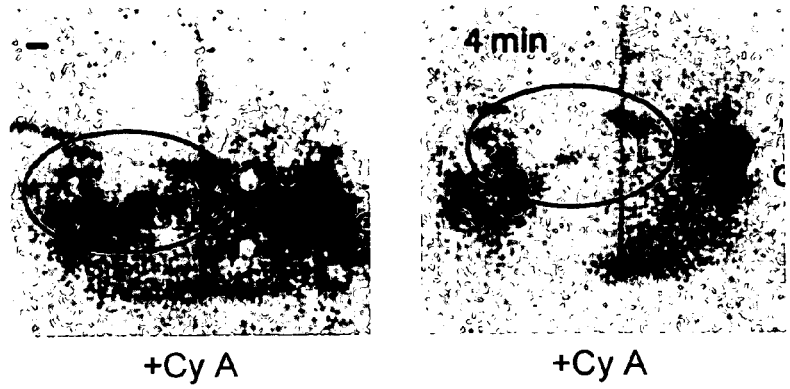

The ability of cyclosporin A to block the effect of DHPG on CK1ε indicates that the regulation by DHPG involves direct dephosphorylation of CK1ε by calcineurin. To examine the phosphorylation state of CK1ε in response to DHPG, N2a cells that expressed HA-CK1ε were metabolically labeled with $^{32}P$ and then treated with DHPG for various periods of time. HA-CK1ε was immunoprecipitated, separated by SDS-PAGE (FIG. 10A), and then subjected to two-dimensional phosphopeptide mapping (FIG. 10B). There was little apparent change in the total level of phosphorylation of CK1ε after incubation of cells with DHPG (FIG. 10A). However, peptide mapping revealed that DHPG treatment resulted in rapid and transient dephosphorylation of a subset of phosphopeptides (FIG. 10B). At 0 time, wild-type CK1ε was found to be highly phosphorylated at one site (basic peptide labeled "C" in FIG. 10B, panel 1). In addition, 7–10 less prominent peptides were phosphorylated (acidic sites circled in FIG. 10B, panel 1). Treatment with DHPG for 2 or 4 min resulted in the dephosphorylation of the acidic peptides, while there was no significant dephosphorylation of the control (basic) peptide. Ten min after DHPG treatment, the phosphorylation level of the acidic peptides returned to the same level as observed in the "0 min" sample. Pre-incubation of cells with cyclosporin A (1 μM) for 30 min before addition of DHPG prevented the transient dephosphorylation of the acidic peptides in CK1ε (FIG. 10C, measured at the 4 min time point). Together these results indicate that DHPG stimulates calcineurin and results in transient dephosphorylation of a subset of autophosphorylation sites in CK1ε.

7.3.5. C-TERMINAL AUTOPHOSPHORYLATION OF CK1ε IS INVOLVED IN REGULATION OF ITS ACTIVITY BY DHPG

Figure 11A:
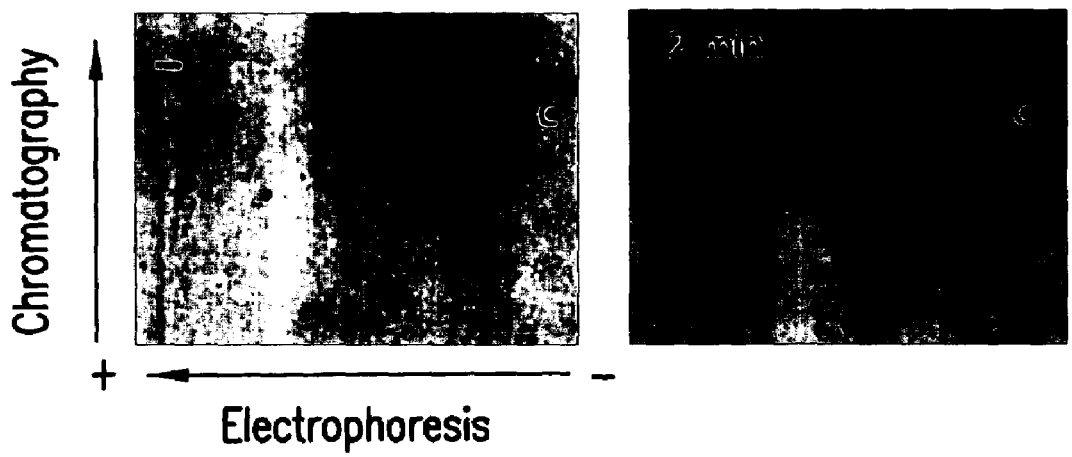
Figure 11B:
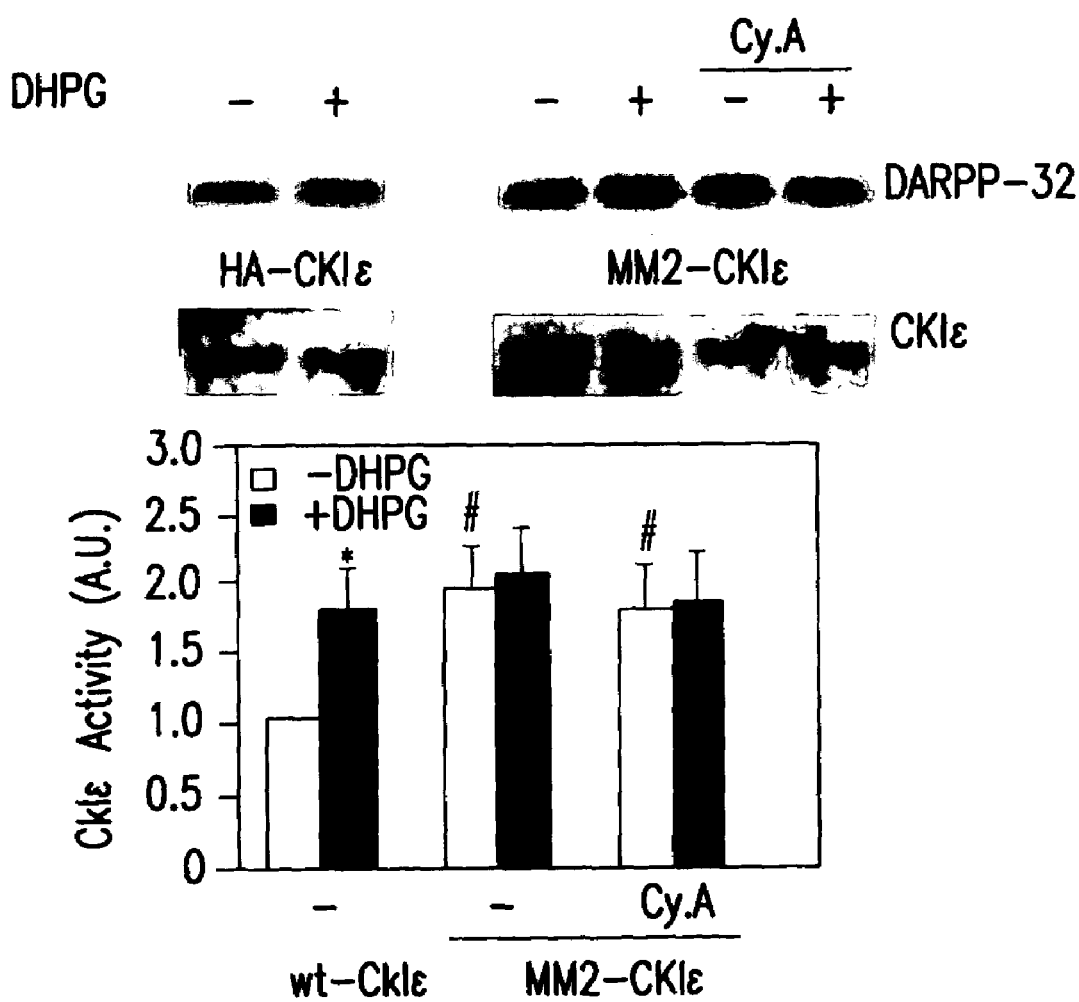

Eight phosphorylation sites in the C-terminal domain of CK1ε were identified as probable in vivo autophosphorylation sites (19). To further examine the nature of CK1ε activation, a mutant of CK1ε, MM2, was tested that lacked the 8 sites (S323A/T325A/T334A/T337A/S368A/S405A/T407A/S408A). Myc-MM2-CK1ε was transiently transfected into N2a cells, immunoprecipitated and subjected to phosphopeptide mapping and kinase activity assay. Phosphopeptide mapping revealed that MM2-CK1ε was autophosphorylated only at the control (basic) peptide, and treatment with DHPG had no effect on phosphorylation (FIG. 11A). Treatment with DHPG had no effect on MM2-CK1ε activity assayed using DARPP-32 as substrate, in the absence or presence of cyclosporin A (FIG. 11B). The expression level of myc-tagged MM2-CK1ε in N2a cells was about the same as the HA-tagged wild-type CK1ε, but the immunoprecipitated MM2-CK1ε was approximately 2-fold more active than HA-CK1ε in the absence of DHPG (FIG. 11B).

Inhibitory autophosphorylation site(s) within the catalytic domain may also contribute to autoinhibition of CK1ε (18). The phosphopeptide maps revealed that the control (basic) phosphopeptide was present in both wild-type and MM2-CK1ε, and remained phosphorylated despite treatment with DHPG (FIGS. 10 and 11). The identity of the control site phosphorylated under basal conditions is not known. Comparison of the phosphopeptide maps with those obtained in a previous study of wild-type CK1ε and a kinase-dead mutant suggest that this site is not autophosphorylated by an intramolecular mechanism (c.f. peptide f in FIG. 11B of Gietzen et al., 1999, J. Biol. Chem. 274(45), 32063–70) and may be phosphorylated by another protein kinase in intact cells.

Figure 12A:
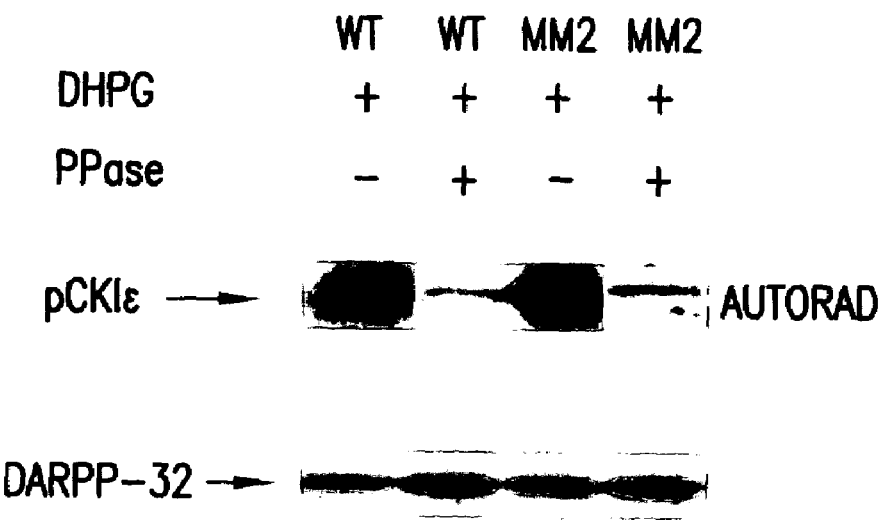
Figure 12B:
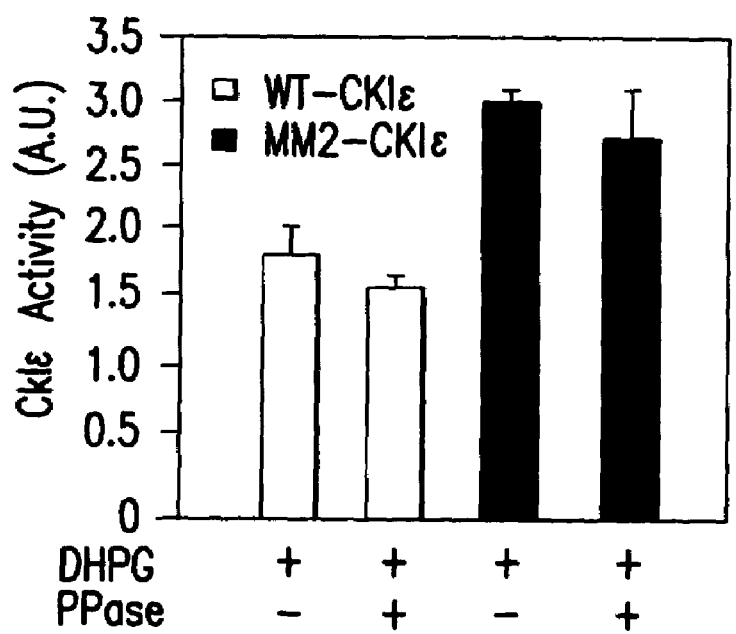

To examine whether phosphorylation of this site has any influence on CK1ε activity, tagged-CK1ε was immunoprecipitated from N2a cell lysates and incubated with on-specific lambda protein phosphatase. The incubation with lambda phosphatase substantially reduced phosphorylation of either wild-type or MM2-CK1ε, as revealed by studies in which cells were pre-labeled with $^{32}P$ (and treated with DHPG) (FIG. 12A, upper panel). Other samples were prepared in parallel from unlabeled N2a cells, treated with lambda phosphatase, and CK1 activity was assayed using DARPP-32 as substrate. Phosphatase treatment did not apparently affect the activity of wild-type or MM2-CK1ε (all cells were preincubated with DHPG) (FIG. 12A, lower panel, and FIG. 12B), suggesting that phosphorylation of the control site in intact cells did not regulate CK1ε. In contrast, protein phosphatase treatment increased the activity of wild-type CK1ε isolated from cells incubated in the absence of DHPG.

7.4. DISCUSSION

In the present example, we have examined the signal transduction pathway that links stimulation of group I mGluRs to CK1ε activation. The results obtained are consistent with the mechanism illustrated in FIG. 13. Activation of mGluR1 receptors stimulates G proteins that are coupled to PLCβ, $Ca^{2+}$ released from IP3-sensitive stores activates the $Ca^{2+}$/calmodulin-dependent phosphatase, calcineurin (PP2B), and calcineurin then dephosphorylates the inhibitory autophosphorylation sites on CK1ε. Dephosphorylation of CK1ε, results in an increase in kinase activity. However, this increase is transient due to the subsequent autophosphorylation and autoinhibition of the kinase.

The previous example (Section 6) has shown that in neostriatal slices, DHPG, an agonist for group I mGluRs, increased CK1 activity, leading to enhanced phosphorylation of Ser-137 of DARPP-32. In the present example, we found that the phosphorylation of Ser-137 of DARPP-32 in neostriatal neurons was sensitive to U73122, BAPTA and cyclosporin A. The phosphorylation of Thr-75 was also sensitive to these inhibitors, supporting the conclusion reached in the previous example (Section 6) that activation of CK1 leads to activation of Cdk5. The present results, carried out largely using transfected cell lines, support the likelihood that CK1ε is a target for regulation by type I mGluRs in neostriatal neurons. Other CK1 isoforms may be activated through a pathway similar to that shown in FIG. 13. The C-terminal 125 amino acids of CK1δ are approximately 50% identical to the corresponding domain of CK1ε. In addition, several in vitro studies have found that the activity of CK1δ, like CK1ε, is regulated by autophosphorylation (17,28). Prior in vitro studies have also indicated that all three CK1γ isoforms can be autophosphorylated (17). Thus, these isoforms may be regulated in a similar fashion. CK1α, δ and ε isoforms have all been found to be expressed in brain, and are likely to be widely distributed in neurons (29–31). In addition, the results indicate that CK1α, δ and ε isoforms are expressed in neostriatum. Thus, activation of calcineurin leads to transient activation of several CK1 isoforms in neostriatal slices (see also below).

Autophosphorylation of multiple C-terminal sites in CK1δ and CK1ε appears to be required for inhibition, although the precise relationship between individual sites and enzyme activity remains to be clarified (17–19). Autophosphorylation is associated with inhibition of enzyme activity towards protein substrates but does not affect phosphorylation of some short synthetic peptides. This latter observation indicates that autophosphorylation serves to negatively influence protein substrate binding by a process that does not block access to the active site of the kinase. Ser-137, the site phosphorylated in DARPP-32 by CK1, is situated at the C-terminal end of a highly acidic region of the protein (23 out of 30 residues are either glutamate or aspartate) (32). The phosphorylated C-terminal domain of CK1ε (or other isoforms) may act to block binding of longer polypeptide substrates containing acidic domains but not shorter synthetic peptides. Dephosphorylation of the C-terminal domain then leads to a loss of this inhibitory constraint. Alternatively, an unphosphorylated C-terminal domain (which, in CK1ε, contains a significant excess of basic amino acids) may serve a positive role in binding to polypeptide substrates that contain acidic domains.

The present study establishes that dephosphorylation of the autophosphorylation sites of CK1ε is a regulated physiological event in intact cells. The results provide insight into the molecular events involved in regulation of CK1ε activity in intact cells. Previous studies of CK1ε have indicated that at least 8 sites are autophosphorylated in vitro. However, in intact cells autophosphorylation of many of these sites is apparent only in the presence of okadaic acid or calyculin A, inhibitors of PP1 and PP2A (19,28). Moreover, autophosphorylation of these sites in the presence of PP1/PP2A inhibitors is associated with decreases in electrophoretic mobility detected using SDS-PAGE.

In the present example, a significant level of autophosphorylation of CK1ε was observed in intact cells under basal conditions. Moreover, treatment with DHPG or cyclosporin A had no effect on the electrophoretic mobility of the protein, despite the dephosphorylation of a subset of the sites phosphorylated. The results indicate that there are a least two subsets of autophosphorylation sites. One set is subject to dephosphorylation by calcineurin, is not associated with any alteration of electrophoretic mobility, and is phosphorylated under basal conditions in intact cells, as long as calcineurin is inactive. The second set is subject to dephosphorylation by PP1 or PP2A, is associated with a decrease in electrophoretic mobility, and is maintained in a dephosphorylated state in intact cells by active PP1 or PP2A. Additional mutagenesis can be used to identify the site(s) in CK1ε that are specifically dephosphorylated by either calcineurin or PP1/PP2A in intact cells.

The results from the present example indicate that one or more of the sites phosphorylated under basal conditions, and dephosphorylated by activated calcineurin, is associated with regulation of CK1ε is activity. It also demonstrates that autophosphorylation of one or more of the sites dephosphorylated in intact cells by PP1/PP2A is associated with regulation of CK1ε activity. While the sites that are sensitive to PP1/PP2A are maintained in a dephosphorylated state in cells in culture (and apparently in neostriatal neurons under basal conditions), physiological inhibition of PP1 or PP2A results in additional inhibition of CK1ε. For example, in neostriatal neurons, stimulation of phosphorylation of DARPP-32 by D1 dopamine receptors may lead to inhibition of PP1 and may influence CK1ε activity. Autophosphorylation of these different sets of sites may result in independent modes of regulation of CK1ε, and/or there may be a sort of interdependence between autophosphorylation of the different sites and regulation of CK1. Autophosphorylation of different sites may have additive or synergistic effects, may occlude one another, or may modulate the ability of CK1 to interact with distinct substrates. Interestingly, three sites in CK1ε (T325, S368 and S405) appear to be conserved in CK1δ. These conserved sites may also confer regulation of CK1δ by calcineurin in intact cells. Alternatively, different autophosphorylation sites may be used to confer differential physiological regulation of CK1 isoforms by protein phosphatases.

Previous observations have indicated that CK1 may phosphorylate Ser-137 of DARPP-32 (see also 33,34). Phosphorylation of Ser-137 impairs the ability of Thr-34 of DARPP-32 to be dephosphorylated by calcineurin, thereby modulating the DARPP-32/PP1 cascade. The previous example (Section 6) demonstrates that activation of CK1 by group I mGluRs results in phosphorylation of Ser-137 and of Thr-75 of DARPP-32 in neostriatal neurons and that this leads to regulation of voltage-dependent $Ca^{2+}$ channels. A variety of other studies have provided strong support for a role of CK1 isoforms, particularly CK1 δ and CK1ε, in diverse cellular processes such as regulation of Wnt signaling and of the circadian clock (7–10,12,14–16). CK1δ and CK1ε have also been implicated in the pathophysiology of Alzheimer s disease (30,35,36).

The results disclosed in the present example demonstrate that regulation of CK1ε (and possibly CK1δ) by autophosphorylation and transient dephosphorylation by calcineurin plays an important role in the regulation of these other processes that involve the enzyme. Alteration of calcineurin activity may result from regulation of mGluRs or via an alternative Pathway that also increases the concentration of intracellular $Ca^{2+}$ in mammalian cells.

7.5. REFERENCES

1. Gross, S. D., and Anderson, R. A. (1998) *Cell Signal* 10(10), 699–711.
2. Vielhaber, E., and Virshup, D. M. (2001) *IUBMB Life* 51(2), 73–8.
3. Tobin, A. B., Totty, N. F., Sterlin, A. E., and Nahorski, S. R. (1997) *J Biol Chem* 272 (33), 20844–9.
4. Budd, D. C., McDonald, J. E., and Tobin, A. B. (2000) *J Biol Chem* 275(26), 19667–75.

5. Knippschild, U., Milne, D. M., Campbell, L. E., DeMaggio, A. J., Christenson, E., Hoekstra, M. F., and Meek, D. W. (1997) *Oncogene* 15(14), 1727–36.
6. Sakaguchi, K., Saito, S., Higashimoto, Y., Roy, S., Anderson, C. W., and Appella, E. (2000) *J Biol Chem* 275(13), 9278–83.
7. Sakanaka, C., Leong, P., Xu, L., Harrison, S. D., and Williams, L. T. (1999) *Proc Natl Acad Sci USA* 96(22), 12548–52.
8. Peters, J. M., McKay, R. M., McKay, J. P., and Graff, J. M. (1999) *Nature* 401(675 1), 345–50.
9. McKay, R. M., Peters, J. M., and Graff, J. M. (2001) *Dev Biol* 235(2), 388–96.
10. Gao, Z. H., Seeling, J. M., Hill, V., Yochum, A., and Virshup, D. M. (2002) *Proc Natl Acad Sci USA* 99(3), 1182–7.
11. Yanagawa Si, S., Matsuda, Y., Lee, J. S., Matsubayashi, H., Sese, S., Kadowaki, T., and Ishimoto, A. (2002) *Embo J* 21(7), 1733–1742.
12. Liu, C., Li, Y., Semenov, M., Han, C., Baeg, G. H., Tan, Y., Zhang, Z., Lin, X., and He, X. (2002) *Cell* 108(6), 837–47.
13. Eide, E. J., and Virshup, D. M. (2001) *Chronobiol Int* 18(3), 389–98.
14. Lowrey, P. L., Shimomura, K., Antoch, M. P., Yamazaki, S., Zemenides, P. D., Ralph, M. R., Menaker, M., and Takahashi, J. 5. (2000) *Science* 288(5465), 483–92.
15. Toh, K. L., Jones, C. R., He, Y., Eide, E. J., Hinz, W. A., Virshup, D. M., Ptacek, L. J., and Fu, Y. H. (2001) *Science* 291(5506), 1040–3.
16. Lee, C., Etchegaray, J. P., Cagampang, F. R., Loudon, A. S., and Reppert, S. M. (2001) *Cell* 107(7), 855–67.
17. Graves, P. R., and Roach, P. J. (1995) *J Biol Chem* 270(37), 21689–94.
18. Cegielska, A., Gietzen, K. F., Rivers, A., and Virshup, D. M. (1998) *J Biol Chem* 273(3), 1357–64.
19. Gietzen, K. F., and Virshup, D. M. (1999) *J Biol Chem* 274(45), 32063–70.
20. Liu, F., Ma, X. H., Ule, J., Bibb, J. A., Nishi, A., DeMaggio, A. J., Yan, Z., Nairn, A. C., and Greengard, P. (2001) *Proc Natl Acad Sci USA* 98(20), 11062–8.
21. Bibb, J. A., Snyder, G. L., Nishi, A., Yan, Z., Meijer, L., Fienberg, A. A., Tsai, L. H., Kwon, Y. T., Girault, J. A., Czernik, A. J., Huganir, R. L., Hemmings, H. C., Jr., Nairn, A. C., and Greengard, P. (1999) *Nature* 402(6762), 669–71.
22. Nishi, A., Snyder, G. L., and Greengard, P. (1997) *J Neurosci* 17(2 1), δ 147–55.
23. Nairn, A. C., and Greengard, P. (1987) *J Biol Chem* 262(15), 7273–81.
24. Conn, P. J., and Pin, J. P. (1997) *Annu Rev Pharmacol Toxicol* 37, 205–37
25. Paolillo, M., Montecucco, A., Zanassi, P., and Schinelli, 5. (1998) *Eur J Neurosci* 10(6), 1937–45.
26. Cartmell, J., Goepfert, F., Knoflach, F., Pink, J. R., Bleuel, Z., Richards, J. G., Schaffhauser, H., Kemp, J. A., Wichmann, J., and Mutel, V. (1998) *Brain Res* 791(1–2), 19 1–9.
27. Goto, S., Matsukado, Y., Mihara, Y., Inoue, N., and Miyamoto, E. (1986) *Brain Res* 397(1), 161–72.
28. Rivers, A., Gietzen, K. F., Vielhaber, E., and Virshup, D. M. (1998) *J Biol Chem* 273(26), 15980–4.
29. Graves, P. R., Haas, D. W., Hagedorn, C. H., DePaoli-Roach, A. A., and Roach, P. J. (1993) *J Biol Chem* 268(9), 6394–401.
30. Ghoshal, N., Smiley, J. F., DeMaggio, A. J., Hoekstra, M. F., Cochran, E. J., Binder, L. I., and Kuret, J. (1999) *Am J Pathol* 155(4), 1163–72.
31. Takano, A., Shimizu, K., Kani, S., Buijs, R. M., Okada, M., and Nagai, K. (2000) *FEBS Lett* 477(1–2), 106–12.
32. Hemmings, H. C., Jr., Nairn, A. C., Elliott, J. I., and Greengard, P. (1990) *J Biol Chem* 265(33), 20369–76.
33. Desdouits, F., Cohen, D., Nairn, A. C., Greengard, P., and Girault, J. A. (1995) *J Biol Chem* 270(15), 8772–8.
34. Desdouits, F., Siciliano, J. C., Greengard, P., and Girault, J. A. (1995) *Proc Natl Acad Sci USA* 92(7), 2682–5.
35. Kuret, J., Johnson, G. S., Cha, D., Christenson, E. R., DeMaggio, A. J., and Hoekstra, M. F. (1997) *J Neurochem* 69(6), 2506–15.
36. Schwab, C., DeMaggio, A. J., Ghoshal, N., Binder, L. I., Kuret, J., and McGeer, P. L. (2000) *Neurobiol Aging* 21(4), 503–10.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for modulating cyclin-dependent kinase 5 ("Cdk5") activity in a cell or tissue comprising
   (a) contacting the cell or tissue with an effective amount of a compound that alters the activity of phospholipase C-beta ("PLCβ"), wherein contact of the cell or tissue with the compound results in a modulation of Cdk5 activity; and
   (b) comparing the Cdk5 activity in the cell or tissue contacted with the compound that alters the activity of PLCβ to the Cdk5 activity in a control cell or control tissue not contacted with the compound that alters the activity of PLCβ.

2. The method of claim 1, wherein the compound that alters the activity of PLCβ is a PLCβ antagonist and wherein contact of the cell or tissue with the PLCβ antagonist decreases Cdk5 activity.

3. The method of claim 2, wherein the cell or tissue is contacted with the PLCβ antagonist in vivo.

4. The method of claim 2, wherein the cell or tissue is contacted with the PLCβ antagonist in vitro.

5. The method of claim 4 wherein in step (b), the decrease in Cdk5 activity in the cell or tissue contacted with the PLCβ antagonist is relative to the Cdk5 activity in the control cell or control tissue not contacted with the PLCβ antagonist.

6. The method of claim 5 further comprising contacting the cell or tissue contacted with the PLCβ antagonist and control cell or control tissue with a group I metabotropic glutamate receptor agonist prior to the the comparing the Cdk5 activities in the cell or tissue and in the control cell or control tissue contacted with the PLCβ antagonist.

7. The method of claim 5, wherein the Cdk5 activities are determined by detecting the amount of phosphorylation of threonine-75 in dopamine- and cyclic AMP-regulated phosphoprotein of 32 kilodaltons ("DARPP-32").

* * * * *